United States Patent
Saxon et al.

(10) Patent No.: US 11,518,818 B2
(45) Date of Patent: Dec. 6, 2022

(54) THERAPEUTIC ANTI-IGE ANTIBODIES AND METHODS AND COMPOSITIONS THEREOF

(71) Applicants: The Regents of the University of California, Oakland, CA (US); Sixal, Inc., Santa Monica, CA (US)

(72) Inventors: Andrew Saxon, Santa Monica, CA (US); Ke Zhang, Los Angeles, CA (US)

(73) Assignees: The Regents of the University of California, Oakland, CA (US); Sixal, Inc., Santa Monica, CA (US)

( * ) Notice: Subject to any disclaimer, the term of this patent is extended or adjusted under 35 U.S.C. 154(b) by 0 days.

(21) Appl. No.: 16/475,614

(22) PCT Filed: Jan. 5, 2018

(86) PCT No.: PCT/US2018/012479
§ 371 (c)(1),
(2) Date: Jul. 2, 2019

(87) PCT Pub. No.: WO2018/129248
PCT Pub. Date: Jul. 12, 2018

(65) Prior Publication Data
US 2019/0322766 A1    Oct. 24, 2019

Related U.S. Application Data

(60) Provisional application No. 62/443,547, filed on Jan. 6, 2017.

(51) Int. Cl.
*C07K 16/42*    (2006.01)
*A61P 37/08*    (2006.01)

(52) U.S. Cl.
CPC .......... *C07K 16/4291* (2013.01); *A61P 37/08* (2018.01); *C07K 2317/24* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 8,043,620 | B2 * | 10/2011 | Qian | ................... A61P 11/00 424/158.1 |
| 2001/0033842 | A1 | 10/2001 | Jardieu | |
| 2005/0169909 | A1 | 8/2005 | Singh | |
| 2009/0117124 | A1 | 5/2009 | Liu et al. | |
| 2013/0243750 | A1 | 9/2013 | Scheerens et al. | |

FOREIGN PATENT DOCUMENTS

| | | | | |
|---|---|---|---|---|
| EP | 1249456 | A1 | 10/2002 | |
| WO | 0209751 | A2 | 2/2002 | |
| WO | 2004070011 | | 8/2004 | |
| WO | 2006113909 | A2 | 10/2006 | |
| WO | 2008070593 | A2 | 6/2008 | |
| WO | WO 2012/069557 | * | 5/2012 | ............. C07K 16/22 |
| WO | 2013192594 | A2 | 12/2013 | |
| WO | 2015195631 | | 12/2015 | |
| WO | 2017186928 | A1 | 11/2017 | |
| WO | 2017189959 | A1 | 11/2017 | |
| WO | WO 2019/141268 | * | 7/2019 | ........... A61K 39/395 |

OTHER PUBLICATIONS

Mariuzza, R.A. etal. The Structural Basis of Antigen-Antibody Recognition1 Annu. Rev. Biophys. Biphys. Chem. 16:139-159, 1987.*
Rudikoff et al. 'Single amino acid substitution altering antigen binding specificity.' Proc. Natl. Acad. Sci 79:1979-1983, 1982.*
Rader et al. 'A phage display approach for rapid antibody humanization: Designed combinatorial V gene libraries.' Proc. Natl. Acad. Sci.95:8910-8915, 1998.*
MacCallum et al. "Antibody-antigen interactions: contact analysis and binding site topography", Journal of Molecular Biology, 1996. Vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Zhang et al. 'Blocking Allergic Reaction through Targeting Surface-Bound IgE with Low-Affinity Anti-IgE Antibodies.' J. Immunol. 198:3823-3834, 2017.*
Zhang et al. 'Inhibition of Allergic Reactivity through Targeting FcεRI-Bound IgE with Humanized Low-Affinity Antibodies.' J. Immunol. 203:2777-2790, 2019.*

(Continued)

*Primary Examiner* — Nora M Rooney
(74) *Attorney, Agent, or Firm* — Suzannah K. Sundby, Esq.; Canady + Lortz LLP

(57) ABSTRACT

Disclosed herein are anti-IgE antibodies having low binding affinity to human IgE and compositions and methods thereof. In some embodiments, the present invention provides a composition comprising one or more humanized low affinity anti-IgE antibodies (hLAAIGEs) and a pharmaceutically acceptable carrier. In some embodiments, the present invention provides a method of treating a subject for an IgE-mediated disorder, which comprises administering to the subject one or more hLAAIGEs or a composition thereof. In some embodiments, the IgE-mediated disorder is an allergic reaction.

20 Claims, 20 Drawing Sheets

Specification includes a Sequence Listing.

(56) References Cited

OTHER PUBLICATIONS

Sailer et al. 'Molecular ensembles make evolution unpreictable.' PNAS 114(45):11938-11943, 2017.*
International Search Report received in PCT/US2018/012479 dated May 31, 2018.
Written Opinion received in PCT/US2018/012479 dated May 31, 2018.
Extended European Search report received in EP 18736220.7, dated Nov. 12, 2020.
Kawakami & Blank, "From IgE to Omalizumab", Dec. 2016, pp. 4187-4192, vol. 197, No. 11, Publisher: J Immunol.
Kolbinger et al., "Humanization of a mouse anti-human IgE antibody: a potential therapeutic for IgE-mediated allergies", Nov. 1993, pp. 971-980, vol. 6, No. 8, Publisher: Protein Eng.
Presta, et al., "Humanization of an antibody directed against IgE", Sep. 1, 1993, pp. 2623-2632, vol. 151, No. 5, Publisher: The Journal of Immunology.

* cited by examiner

US 11,518,818 B2

THERAPEUTIC ANTI-IGE ANTIBODIES AND METHODS AND COMPOSITIONS THEREOF

ACKNOWLEDGEMENT OF GOVERNMENT SUPPORT

This invention was made with Government support under Grant Number AI102279 awarded by the National Institutes of Health. The Government has certain rights in the invention.

REFERENCE TO A SEQUENCE LISTING SUBMITTED VIA EFS-WEB

The content of the ASCII text file of the sequence listing named "20201016_034044_169 US1_subseq_ST25" which is 89.3 kb in size was created on Oct. 16, 2020 and electronically submitted via EFS-Web herewith the application is incorporated herein by reference in its entirety.

BACKGROUND OF THE INVENTION

1. Field of the Invention

The present invention generally relates to humanized antibodies having low affinity binding to IgE.

2. Description of the Related Art

Immunoglobulin E (IgE) constitutes one of the five major classes of antibodies in humans. IgE is a single four-chain unit consisting of two ε heavy chains and two κ light chains or two λ light chains. IgE is synthesized and secreted by B cells that have undergone heavy-chain class switching from μ to ε heavy chain production. Although IgE represents less than one percent of total Ig in blood, this immunoglobulin is a central player in the allergic response.

The immediate allergic response, immediate hypersensitivity or the type I allergic response, is mediated by a complex that includes IgE and FcεRI (the high-affinity receptor for IgE). This complex is formed upon binding of the Fc region of secreted IgE antibodies to FcεRI receptors on the surface of effector cells such as mast cells and basophils. The bound IgE antibodies then serve as effector cell-surface receptors for those antigens, termed allergens, which trigger a type I allergic response. When antigen (e.g., allergen) binds to FcεRI-bound IgE so as to cross-link neighboring IgE/FcεRI complexes, it signals the effector cell to release histamine and other biologically active mediators by exocytosis.

SUMMARY OF THE INVENTION

In some embodiments, the present invention provides a monoclonal antibody (an hLAAIGE) which comprises a VH chain that comprises DTAVYYCAR (SEQ ID NO:7), and a VL chain that comprises LQAED (SEQ ID NO:11) and at least one sequence selected from AAPSV (SEQ ID NO:12), GTKL (SEQ ID NO:13), and RFSGS (SEQ ID NO:14).

In some embodiments, the VH chain comprises WVRQAPG (SEQ ID NO:8), and GLEW (SEQ ID NO:9), and/or VTVSSA (SEQ ID NO:10). In some embodiments, the VH chain is $(X)_{0-1}$VQLXQSG$(X)_5$PGXS$(X)_3$SCXAS-GXTF$(X)_6$WVRQAPGXGLEW$(X)_3$I$(X)_4$G$(X)_3$Y$(X)_6$R$(X)_5$DXS$(X)_2$T$(X)_6$SL$(X)_3$DTAVYYCAR$(X)_{9-11}$WGXGTXVTVSSAS (SEQ ID NO:15). In some embodiments, the VH chain comprises any one or more of the following sequences VQLX1QSG (SEQ ID NO:17), PGX2SX3X4X5SCX6ASGX7TF (SEQ ID NO:18), WVRQAPGX8GLEW (SEQ ID NO:19), WGX9GTX10VTVSSA (SEQ ID NO:20), SLX11X12X13DTAVYYCAR (SEQ ID NO:21), and RX14X15X16X17X18DX19SX20X21T (SEQ ID NO:22), wherein X1 to X21 are each independently any amino acid. In some embodiments, the VH chain comprises any one or more of the following sequences VQLX1QSG (SEQ ID NO:17), PGX2SX3X4X5SCX6ASGX7TF (SEQ ID NO:18), WVRQAPGX8GLEW (SEQ ID NO:19), WGX9GTX10VTVSSA (SEQ ID NO:20), SLX11X12X13DTAVYYCAR (SEQ ID NO:21), and RX14X15X16X17X18DX19SX20X21T (SEQ ID NO:22), wherein X1 is V or G, preferably V, X2 is A or R, preferably A, X3 is L or V, preferably V, X4 is K or R, preferably K, X5 is L or V, preferably V, X6 is A or K, preferably K, X7 is F or Y, preferably Y, X8 is K or Q, preferably Q, X9 is R or Q, X10 is L or T, X11 is T, K, or R, X12 is A or S, X13 is E or D, X14 is F or V, X15 is T or V, X16 is I, F, or M, X17 is S or T, X18 is L, R, or T, X19 is N or T, preferably T, X20 is K, T, or V, and X21 is N or S, preferably S. In some embodiments, the VH chain comprises a sequence having a percent identity of about 75% to about 100%, preferably about 80% to about 100%, more preferably about 90% to 100%, even more preferably about 95% to about 100%, and most preferably about 99% to 100% to SEQ ID NO:2. In some embodiments, the VH chain comprises SEQ ID NO:68, SEQ ID NO:69, or SEQ ID NO:70. In some embodiments, the VH chain comprises a sequence having a percent identity of at least about 90% up to 100%, preferably about 91% up to 100%, more preferably about 95% up to 100%, even more preferably about 97% up to 100%, and most preferably about 99% up to 100% to SEQ ID NO:1. In some embodiments, the VH chain comprises at least 10, 20, 30, 40, or 50 consecutive amino acid residues of SEQ ID NO:23. In some embodiments, the VH chain comprises SEQ ID NO:23.

In some embodiments, the VL chain comprises LQAED (SEQ ID NO:11) plus (a) AAPSV (SEQ ID NO:12) or (b) RFSGS (SEQ ID NO:14) and GTKL (SEQ ID NO:13). In some embodiments, the VL chain comprises $(X)_4$TQ$(X)_{0-1}$PXS$(X)_3$SXG$(X)_3$TIXC$(X)_{2-3}$S$(X)$V$(X)_{9-11}$Q$(X)_2$PG$(X)_2$PKLXIY$(X)_{2-4}$S$(X)_3$S$(X)_{2-4}$RFSGSXSG$(X)_4$LTXSXLQAEDXAXYYC$(X)_{0-2}$Q$(X)_{6-8}$FGXGTKL$(X)_{3-7}$AAPSV$(X)_2$FPPSXE XL$(X)_4$A$(X)_2$VCL$(X)_3$FYP$(X)_4$VXWKXD$(X)_{5-6}$G$(X)_{1-3}$E$(X)_2$T$(X)_8$Y$(X)_2$SSXLXL$(X)_7$H$(X)_2$YXC XVTHXG$(X)_{0-2}$SXVXK$(X)_5$EC$(X)_{0-1}$ (SEQ ID NO:16), wherein each X is independently any amino acid. In some embodiments, the VL chain comprises any one or more of the following sequences RFSGSX22SG (SEQ ID NO:24), LTX23SX24LQAEDX254AX26YY (SEQ ID NO:25), FGX27GTKL (SEQ ID NO:26), AAPSVX28X29FPPSX30EX31L (SEQ ID NO:27), AX32X33VCLX34X35X36FYP (SEQ ID NO:28), HX37X38YX39CX40VTHX41G (SEQ ID NO:29), PX42SX43X44X45SX45GX47X48X49TIX50C (SEQ ID NO:30), QX51X52PGX53X54PKLX55IY (SEQ ID NO:31), wherein X22 to X55 are each independently any amino acid. In some embodiments, the VL chain comprises any one or more of the following sequences RFSGSX22SG (SEQ ID NO:24), LTX23SX24LQAEDX254AX26YY (SEQ ID NO:25), FGX27GTKL (SEQ ID NO:26), AAPSVX28X29FPPSX30EX31L (SEQ ID NO:27), AX32X33VCLX34X35X36FYP (SEQ ID NO:28), HX37X38YX39CX40VTHX41G (SEQ ID NO:29), PX42SX43X44X45SX45GX47X48X49TIX50C (SEQ ID NO:30), QX51X52PGX53X54PKLX55IY (SEQ ID NO:31), wherein X22 is G or K, X23 is I or V, X24 is G or S, X25 is E or V, X26 is D or V, X27 is G, S, or Q, X28 is F or T, X29 is I or L, X30 is D or S, X31 is E or Q, X32 is S or T, X33 is L or V, X34 is I or L, X35 is N or S, X36 is D or N, X37 is K or R, X38 is S or V, X39 is A or S, X40 is E or Q, X41 is E or Q, X42 is A, D, or P, X43 is A, L, or V, X44 is A or S, X45 is G or V, X46 is L or P, X47 is E or Q, X48 is R or S, X49 is A, I, or V, X50 is N or S, X51 is H or Q, preferably Q, X52 is H or K, X53 is K or Q, X54 is A or P, and X55 is L or M. In some embodiments, the VL chain comprises a sequence having a percent identity of at least about 65% up to 100% to SEQ ID NO:4. In some embodiments, the VL chain comprises a sequence selected from the group consisting of: SEQ ID NO:4, SEQ ID NO:5, and SEQ ID NO:6. In some embodiments, the VL chain comprises SEQ ID NO:32, SEQ ID NO:65, or SEQ ID NO:67.

In some embodiments, the hLAAIGE binds human IgE. In some embodiments, the hLAAIGE binds to human IgE when bound to human FcεRI or high affinity IgE receptor. In some embodiments, the IgE epitope recognized by the hLAAIGE comprises at least 10 consecutive amino acid residues of SEQ ID NO:33. In some embodiments, the IgE epitope recognized by the hLAAIGE comprises, consists essentially of, or consists of one or more of the following sequences: SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45. In some embodiments, the IgE epitope recognized by the hLAAIGE comprises at least one of the following sequences: SEQ ID NO:35, SEQ ID NO:39, SEQ ID NO:42, and SEQ ID NO:36.

In some embodiments, the hLAAIGE is a humanized antibody. In some embodiments, the hLAAIGE binds to human IgE with a binding affinity of about $1 \times 10^{-5}$ M to about $1 \times 10^{-9}$ M Kd, about $1 \times 10^{-6}$ M to about $1 \times 10^{-9}$ M Kd, or about $5 \times 10^{-5}$ to about $7 \times 10^{-8}$ M Kd. In some embodiments, the hLAAIGE E59, E14, E17, E23, S91, or H6.2 as disclosed herein.

In some embodiments, the present invention provides a composition comprising one or more hLAAIGEs. In some embodiments, the composition further comprises a pharmaceutically acceptable carrier.

In some embodiments, the present invention provides a method of treating a subject for an IgE-mediated disorder, which comprises administering to the subject one or more hLAAIGEs or a composition thereof. In some embodiments, the IgE-mediated disorder is an allergic reaction. In some embodiments, the allergic reaction is an acute IgE-mediated food allergic reaction. In some embodiments, the IgE-mediated disorder is a food allergy, asthma, allergic rhinitis, atopic dermatitis, urticaria, angioedema, or anaphylactic hypersensitivity. In some embodiments, the present invention provides a method of treating a subject for mastocytosis, which comprises administering to the subject one or more hLAAIGEs or a composition thereof. In some embodiments, the one or more hLAAIGEs or composition thereof is administered prior to the onset of an IgE-mediated allergic reaction. In some embodiments, one or more antibodies according to the present invention and a given allergen are co-administered to a subject to desensitize the subject to the allergen.

In some embodiments, the one or more hLAAIGEs or composition thereof is administered to a subject every 3 to 10 weeks. In some embodiments, the one or more hLAAIGEs or composition thereof is administered to a subject every 3 to 8 weeks. In some embodiments, the one or more hLAAIGEs or composition thereof is administered to a subject every 4 to 8 weeks. In some embodiments, the one or more hLAAIGEs or composition thereof is administered to a subject every 4 to 6 weeks. In some embodiments, the one or more hLAAIGEs or composition thereof is administered to a subject every 4 to 5 weeks. In some embodiments, the one or more hLAAIGEs or composition thereof is administered to a subject monthly. In some embodiments, a therapeutically effective amount of one or more hLAAIGEs according to the present invention are administered to a subject.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein:

FIG. 1 shows the flow cytometry profiles of the BAT. FIG. 2 is a graph summarizing the basophil activation test (BAT) from normal blood basophils showing that hLAAIGE E59 fails to activate human basophils. FIG. 3 is a graph summarizing the lack of histamine release triggering capacity of hLAAIGEs from blood basophils. FIG. 4 is a graph summarizing the lack of β-hexoaminidase-α release from culture skin mast cells by hLAAIGEs. FIG. 5 is a graph summarizing the lack of the β-hexoaminidase-α release from fresh lung mast cells by hLAAIGEs. FIG. 6 shows the results of Passive Cutaneous Anaphylaxis (PCA) in hFcεRIα Tg mouse model where hLAAIGEs fail to induce PCA. FIG. 7 is a graph summarizing the core temperature changes of systemic anaphylaxis in hFcεRIα Tg mice showing that hLAAIGE E59 fails to induce systemic anaphylaxis. FIG. 8 is a graph summarizing the clinical score of the systemic anaphylaxis in hFcεRIα Tg mice showing that hLAAIGE E59 fails to induce systemic anaphylaxis. HLAAIGEs, E4.15 and E7.12, and polyclonal anti-IgE (α-IgE) were used as the positive controls.

FIG. 9 shows that E59 is unable to trigger CD63 expression, an activation marker, on basophils.

FIG. 10 shows that E59 promotes low-level basophil CD203c expression, a marker of potentially protective piecemeal degranulation.

FIG. 11 and FIG. 12 summarize the results evidencing that hLAAIGEs blocked the peanut allergic subject's blood basophil BAT. FIG. 13 and FIG. 14 summarize the results evidencing that hLAAIGEs blocked the cat allergic subject's blood basophil BAT.

FIG. 15, FIG. 16, and FIG. 17 summarize the results evidencing that hLAAIGEs blocked the peanut allergic IgE mediated PCA. In FIG. 17, in the 4 sets of bars, the first bar of each set is Control. FIG. 18 and FIG. 19 summarize the results evidencing that hLAAIGEs attenuated dansyl-IgE mediated the systemic anaphylaxis in hFcεRIα mice. AER-37 is an anti-human FcεRIα mAb used as PCA control * P,0.05; ** P<0.01.

FIG. 20 show confocal images of surface FITC-IgE loaded bone marrow mast cells (BMMCs) that were treated with hIgG1 control (2 μg/ml) and E59 (2 μg/ml) for 24 hours (overlay view). FIG. 21 shows confocal sections of the E59 treated BMMC showing the intracellular-internalized IgE.

FIG. 22 is an electron micrograph showing the phenotype of the intact granules in resting skin mast cells. FIG. 23 is an electron micrograph showing the typical phenotype of piecemeal degranulation induced by E59 at 50 μg/ml for 30 minutes. FIG. 24 is an electron micrograph showing the phenotype of the anaphylactic degranulation induced by polyclonal anti-IgE.

DEFINITIONS

Figure 1:
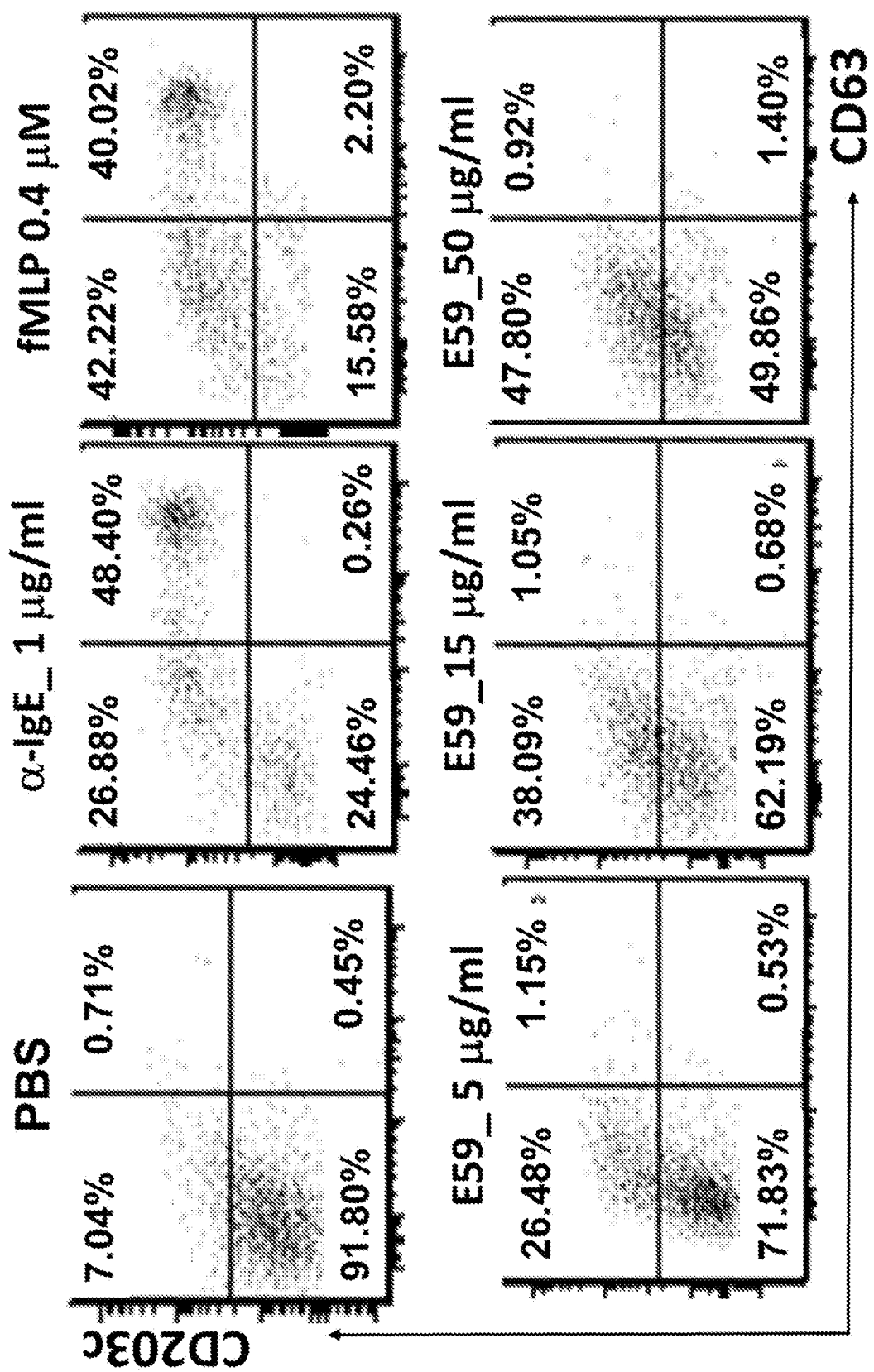
FIG. 1 to FIG. 10 show the safety profiles of some humanized low affinity anti-IgE antibodies (hLAAIGEs).

Unless indicated otherwise, all scientific and technical terms used herein have meanings commonly understood by those skilled in the art to which this invention belongs.

The terms "antibodies" and "immunoglobulin" include antibodies or immunoglobulins of any isotype, whole antibodies (e.g., antibodies composed of a tetramer which in turn is composed of two dimers of a heavy and light chain polypeptide); half antibodies; single chain antibodies; fragments of antibodies (e.g., fragments of whole, half, or single chain antibodies) which retain specific binding to IgE, including, but not limited to Fab, Fv, scFv, and diabodies; chimeric antibodies; humanized antibodies (e.g., humanized whole antibodies, humanized half antibodies, or humanized antibody fragments); and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')$_2$, and or other antibody fragments that retain specific binding to antigen, and monoclonal antibodies. An antibody may be monovalent (e.g., in the case of a half antibody) or bivalent.

"Antibody fragments" comprise a portion of an intact antibody, for example, the antigen binding or variable region of the intact antibody. Examples of antibody fragments include a Fab, Fab', F(ab')$_2$, and Fv fragments; diabodies; linear antibodies (Zapata, et al., Protein Eng. 8(10): 1057-1062 (1995)); and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

A "half antibody" refers to an antibody composed of a dimer of a heavy chain polypeptide and a light chain polypeptide, which heavy and light chains may be joined by noncovalent and/or covalent (e.g., disulfide) bonds. The half antibody may include a heavy chain that includes a human heavy chain constant region, and a light chain that includes a human light chain constant region. As opposed to a "full" or "complete" antibody that consists of two identical heavy chains and two identical light chains—and accordingly has two identical antigen binding sites—a half antibody has a single antigen binding site (i.e., is monovalent). As described in greater detail below, a half antibody may be generated by genetically modifying a nucleic acid that encodes the heavy chain of an anti-IgE antibody, e.g., by substituting one or more heavy chain amino acid residues (e.g., one, two, or more cysteines) that promote heavy chain dimerization for amino acids that do not promote (e.g., prevent) such dimerization, or post-translationally modifying one or more heavy chain amino acid residues (e.g., one, two, or more cysteines) that promote heavy chain dimerization such that the amino acid(s) are no longer capable of interacting with the residues of a different heavy chain.

"Monovalent" when used in the context of an antibody refers to an antibody that contains a single antigen-binding region. "Divalent" when used in the context of an antibody refers to an antibody that contains two antigen-binding regions.

"Fv" comprises the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins may be assigned to different classes. There are five major classes of immunoglobulins:

IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" antibody fragments comprise the $V_H$ and $V_L$ domains of an antibody, where these domains are present in a single polypeptide chain. In some embodiments, the Fv polypeptide further comprises a polypeptide linker between the $V_H$ and $V_L$ domains, which enables the sFv to form the desired structure for antigen binding.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. See, e.g., Hollinger, et al., PNAS USA, 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive", "preferentially binds", and "specifically binds" are used interchangeably herein with respect to antibodies and/or antigen-binding fragments. The term "binding" refers to a direct association between two molecules, due to, for example, covalent, electrostatic, hydrophobic, and ionic and/or hydrogen-bond interactions, including interactions such as salt bridges and water bridges. A subject anti-IgE binds specifically to an epitope within an IgE polypeptide.

By "CDR" or "complementarity determining region" is meant the non-contiguous antigen combining sites found within the variable region of both heavy and light chain polypeptides. CDRs have been described by Kabat, et al., J. Biol. Chem. 252:6609-6616 (1977); Kabat, et al., U.S. Dept. of Health and Human Services, "Sequences of proteins of immunological interest" (1991); by Chothia, et al., J. Mol. Biol. 196:901-917 (1987); and MacCallum, et al., J. Mol. Biol. 262:732-745 (1996), where the definitions include overlapping or subsets of amino acid residues when compared against each other.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In some embodiments, hLAAIGEs are purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or non-reducing conditions using Coomassie blue or silver stain. Isolated antibody includes the antibody in situ within recombinant cells since at least one component of the antibody's natural environment will not be present. In some embodiments, isolated antibodies are prepared by at least one purification step.

As used herein, the term "humanized antibody" refers to an antibody derived from a non-human species and having a protein sequence that has been modified to increase its similarity to human antibodies. Methods of making humanized antibodies are known in the art. See, e.g., U.S. Pat. No. 7,256,273. Humanized antibodies may comprise residues which are found neither in the recipient antibody nor in the imported CDR or framework sequences. See, Queen, et al., PNAS USA 86:10029 10033 (1989), U.S. Pat. Nos. 5,530, 101, 5,585,089, 5,693,761, WO 90/07861, and U.S. Pat. No. 5,225,539. Humanized antibodies can have sequences of naturally occurring human antibodies or can be consensus sequences of several human antibodies. See Kettleborough, et al., Protein Engineering 4:773 (1991); Kolbinger, et al., Protein Engineering 6:971 (1993).

As used herein, the term percent sequence "identity" refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov).

As used herein, the terms "individual", "subject", "host", and "patient", are used interchangeably to refer to humans and non-human animals. The term "non-human animal" includes all vertebrates, e.g., mammals and non-mammals, such as non-human primates, humans, canines, felines, ungulates (e.g., equines, bovines, ovines, porcines, and caprines), rodents, and other veterinary subjects and test animals.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and includes cells in culture, cell supernatants, cell lysates, serum, plasma, biological fluid, and tissue samples. In some cases, a biological sample will include mast cells, basophils, eosinophils, B cells, and the like.

The terms "type-I allergic reaction", "immediate hypersensitivity", "atopic allergy", "type-I hypersensitivity", and the like, as used herein, refer to the physiological response that occurs when an antigen entering the body encounters mast cells or basophils which have been sensitized by IgE attached to its high-affinity receptor, FcεRI on these cells. When an allergen reaches the sensitized mast cell or basophil, it cross-links surface-bound IgE, causing an increase in intracellular calcium ($Ca^{2+}$) that triggers the release of pre-formed mediators, such as histamine and proteases, and newly synthesized, lipid-derived mediators such as leukotrienes and prostaglandins. These autocoids produce the clinical symptoms of allergy. In addition, cytokines, e.g., IL-4, TNF-alpha, are released from degranulating basophils and mast cells, and serve to augment the inflammatory response that accompanies an IgE reaction (see, e.g., Immunology, Fifth Edition, Roitt, et al., eds., 1998, pp. 302-317). The specific manifestations of the hypersensitivity reaction in the sensitive or allergic subject depends on the site of the allergen exposure, the dose of allergen exposure, the reactivity of the organs in the subject (e.g., over-reactive lungs or nose) and the full panoply of the immune response to the allergen in that subject.

Symptoms and signs associated with type I hypersensitivity responses are extremely varied due to the wide range of tissues and organs that might be involved. These symptoms and signs can include: itching of the skin, eyes, and throat, swelling and rashes of the skin (angioedema and urticaria/hives), hoarseness and difficulty breathing due to swelling of the vocal cord area, a persistent bumpy red flaking rash that may occur anywhere on the body, shortness of breath and wheezing (from tightening of the muscles in the airways and plugging of the airways, i.e., bronchoconstriction) in addition to increased mucus and fluid production, chest tightness and pain due to construction of the airway muscles, nausea, vomiting diarrhea, dizziness and fainting from low blood pressure, a rapid or irregular heartbeat and even death as a result of airway and/or cardiac compromise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range.

As used in the specification and the appended claims, the singular forms "a", "an", and "the" include plural referents unless the context clearly dictates otherwise. Thus, for example, reference to "an antibody" or "a half antibody" includes a plurality of such antibodies or half antibodies and reference to "the CDR" includes reference to one or more CDRs and equivalents thereof known to those skilled in the art, and so forth. It is further noted that the claims may be drafted to exclude any optional element. As such, this statement is intended to serve as antecedent basis for use of such exclusive terminology as "solely", "only", and the like, relating to the recitation of claim elements, or use of a "negative" limitation.

The use of "or" includes "and/or" unless the context dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises, consists essentially of, or consists of" is used as a tool to avoid excess page and translation fees and means that in some embodiments the given thing at issue comprises something, and in some embodiments the given thing at issue consists of something. For example, the sentence "In some embodiments, the composition comprises, consists essentially of, or consists of A" is to be interpreted as if written as the following two separate sentences: "In some embodiments, the composition comprises A. In some embodiments, the composition consists essentially of A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

DETAILED DESCRIPTION OF THE INVENTION

The present invention provides humanized antibodies that exhibit a low binding affinity of about $1\times10^{-5}$ M to about $1\times10^{-9}$ M Kd, preferably about $1\times10^{-6}$ M to about $1\times10^{-9}$ M Kd, and more preferably about $1\times10^{-6}$ M to about $1\times10^{-8}$ M Kd (as measured by the "Biacore method", i.e., surface plasmon resonance using Biacore T2000 instrument with a CM5 sensor chip coupled with myeloma IgE (see Zhang, et al. J. Immunol. (2017) DOI: 10.4049/jimmunol.1602022, which is herein incorporated by reference in its entirety) to human IgE. The humanized low affinity anti-IgE antibodies according to the present invention are referred to herein as "hLAAIGEs".

Safety Profiles of hLAAIGEs

Figure 2:
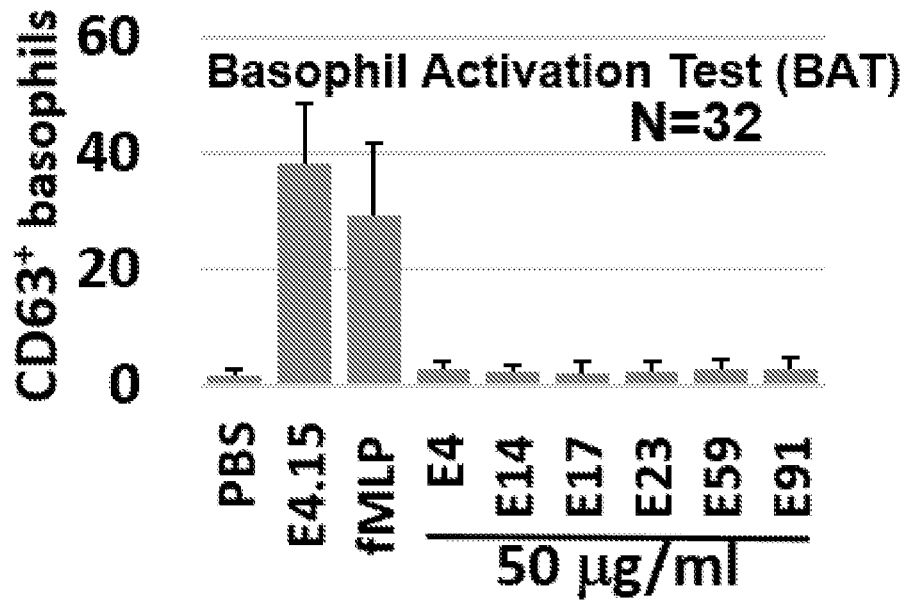
Figure 3:
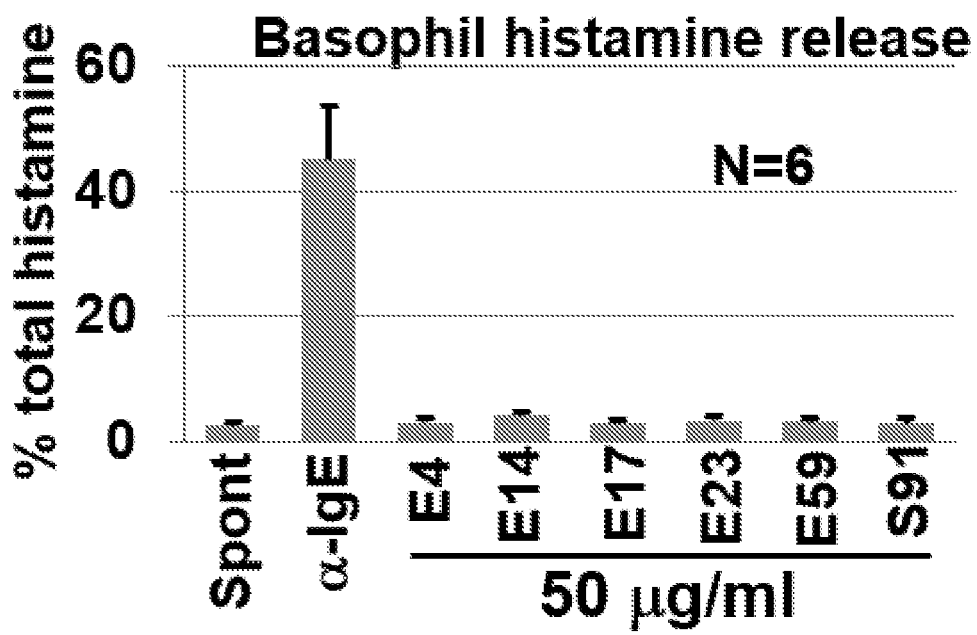
Figure 4:
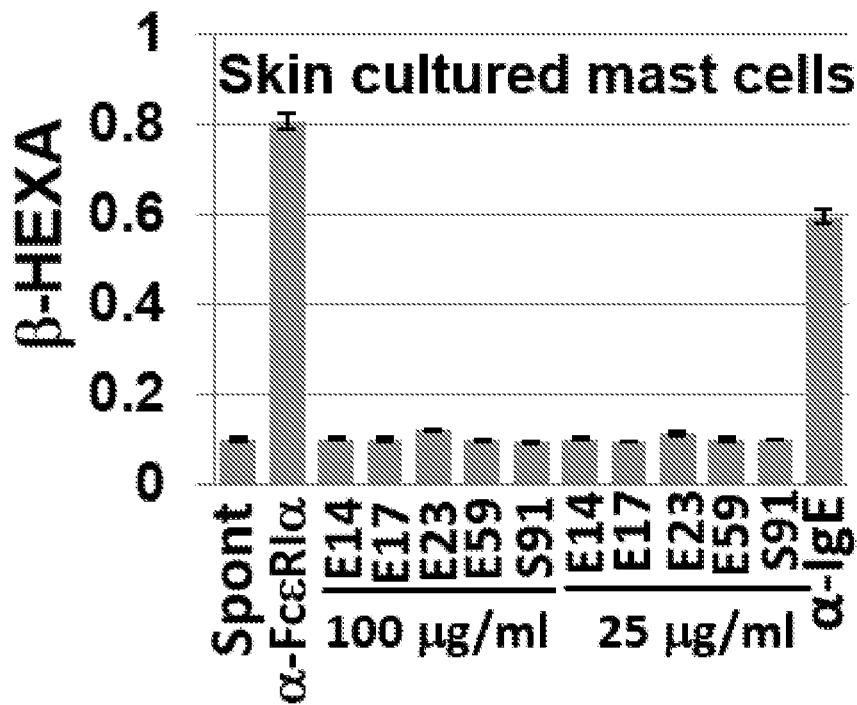
Figure 5:
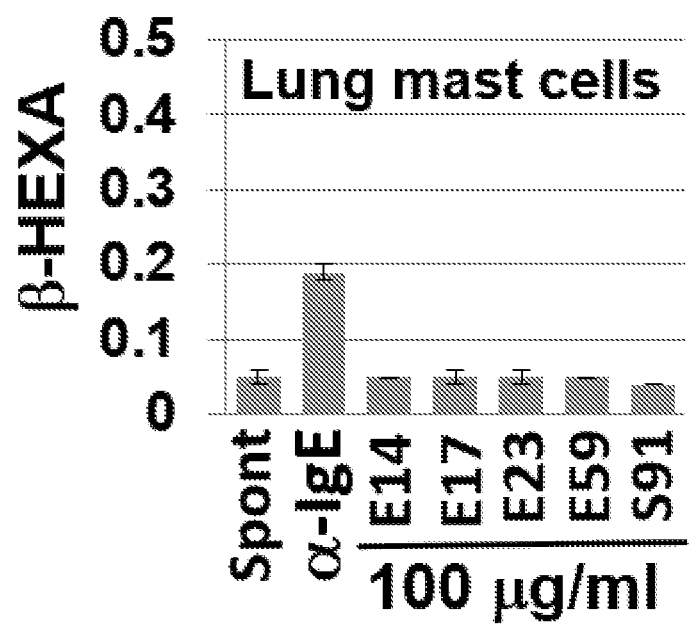
Figure 6:
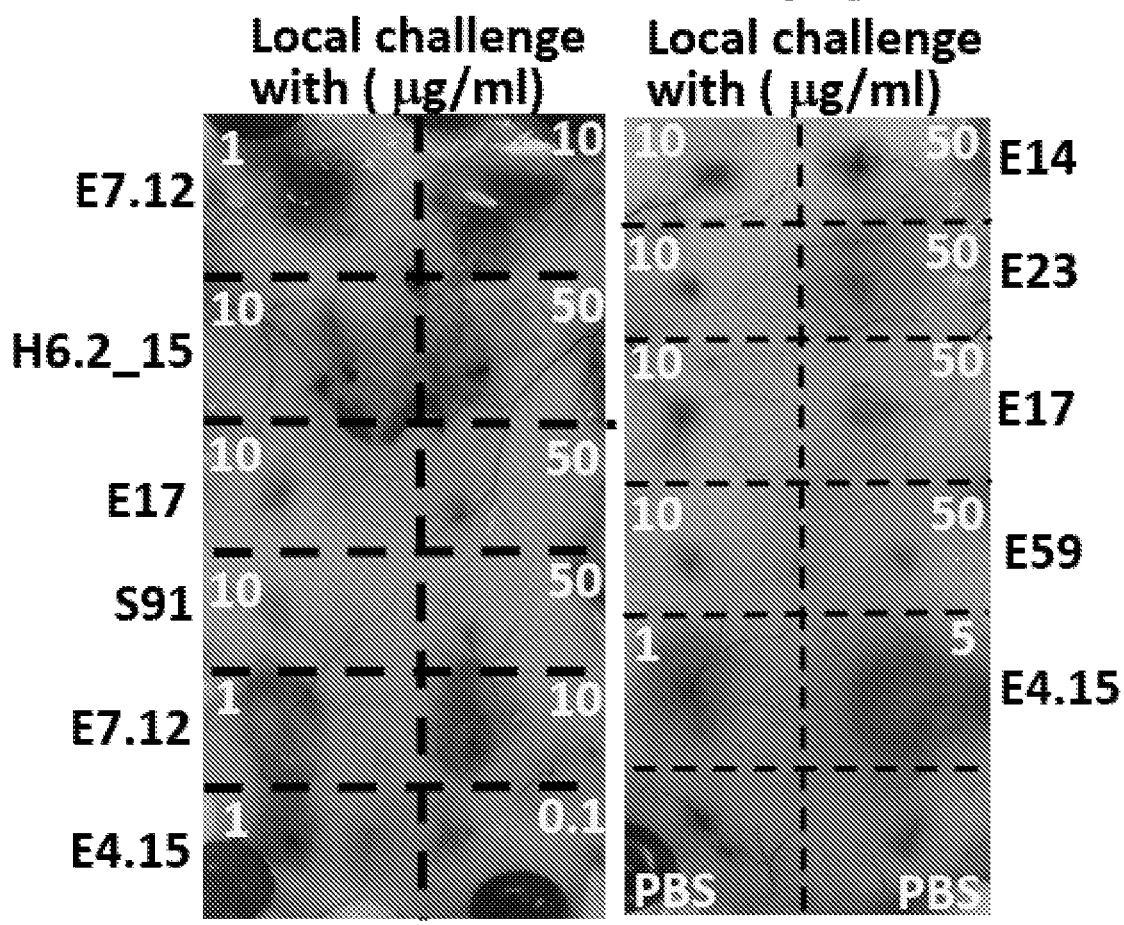
Figure 7:
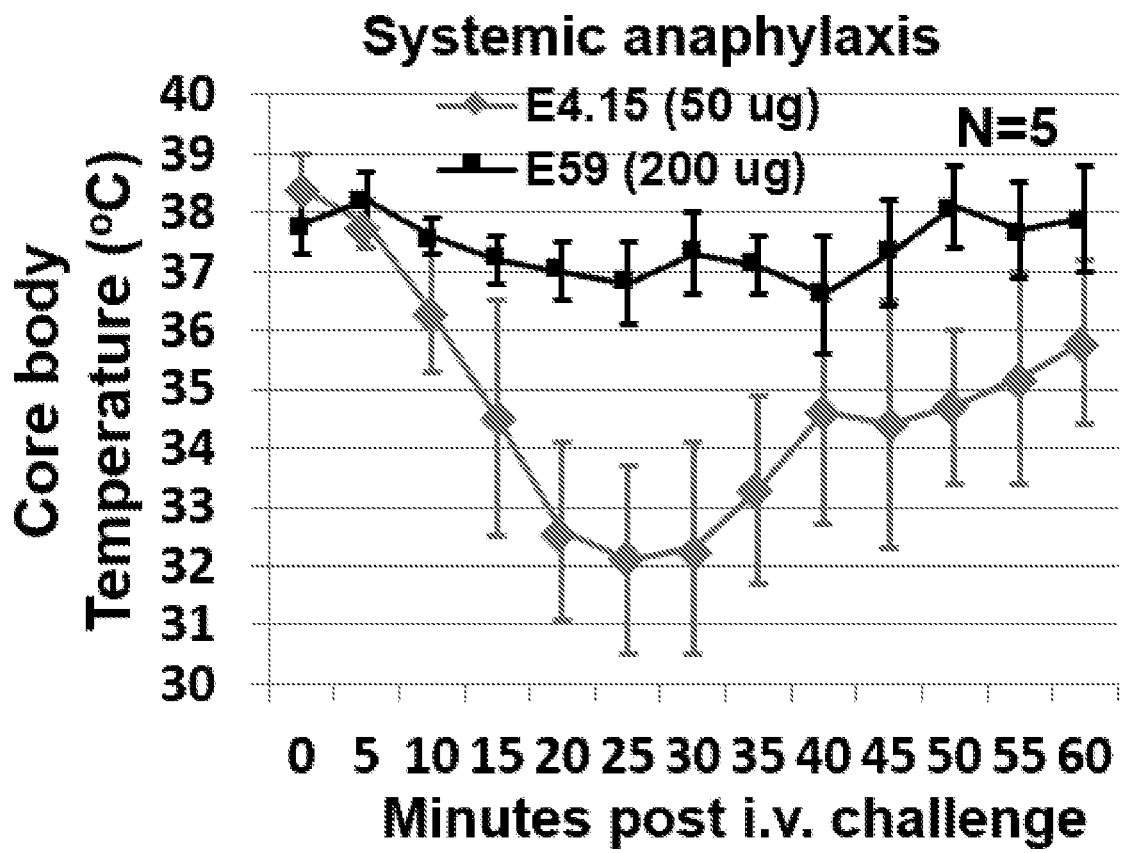
Figure 8:
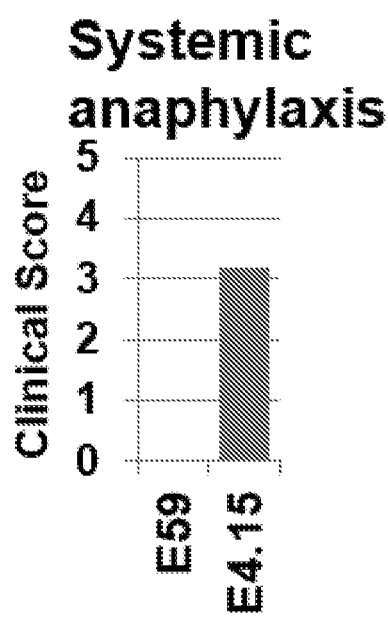

The safety profiles of hLAAIGEs exemplified herein were critically evaluated with multiple approaches and methods described previously and summarized in FIG. 1 to FIG. 8. With flow cytometry based basophil activation test (BAT), in contrast to the positive BAT control (E4.15, a high affinity anti-human IgE mAb, and fMLP, a basophil activator via non-IgE-FcεRI pathway) that induced strong CD63 expression of blood basophils as a marker of BAT activation, hLAAIGE clones E59 (FIG. 1), E14, E17, E23, and S91 (FIG. 2) neither induce basophil CD63 expression, nor trigger basophil histamine release with the concentration up to 50 µg/ml (FIG. 3). E14, E17, E23, and E59 were derived from Founder E17, S91 was derived from Founder F11, and H6.2 was derived from Founder P6.2. These hLAAIGEs at concentrations up to 100 µg/ml did not trigger degranulation (using β-hexoaminidase-α as the degranulation marker) of the cultured skin mast cells (FIG. 4) and freshly isolated lung mast cells (FIG. 5). With hFcεRIα Tg mouse model, the hLAAIGEs neither trigger local PCA reaction up to 50 µg/ml (FIG. 6), nor systemic anaphylaxis (data not shown, using the data from E59 as an example, FIG. 7 and FIG. 8). These comprehensive data demonstrated that the selected hLAAIGEs lack the capacity to trigger degranulation/mediator release from the allergic effector cells.

Figure 9:
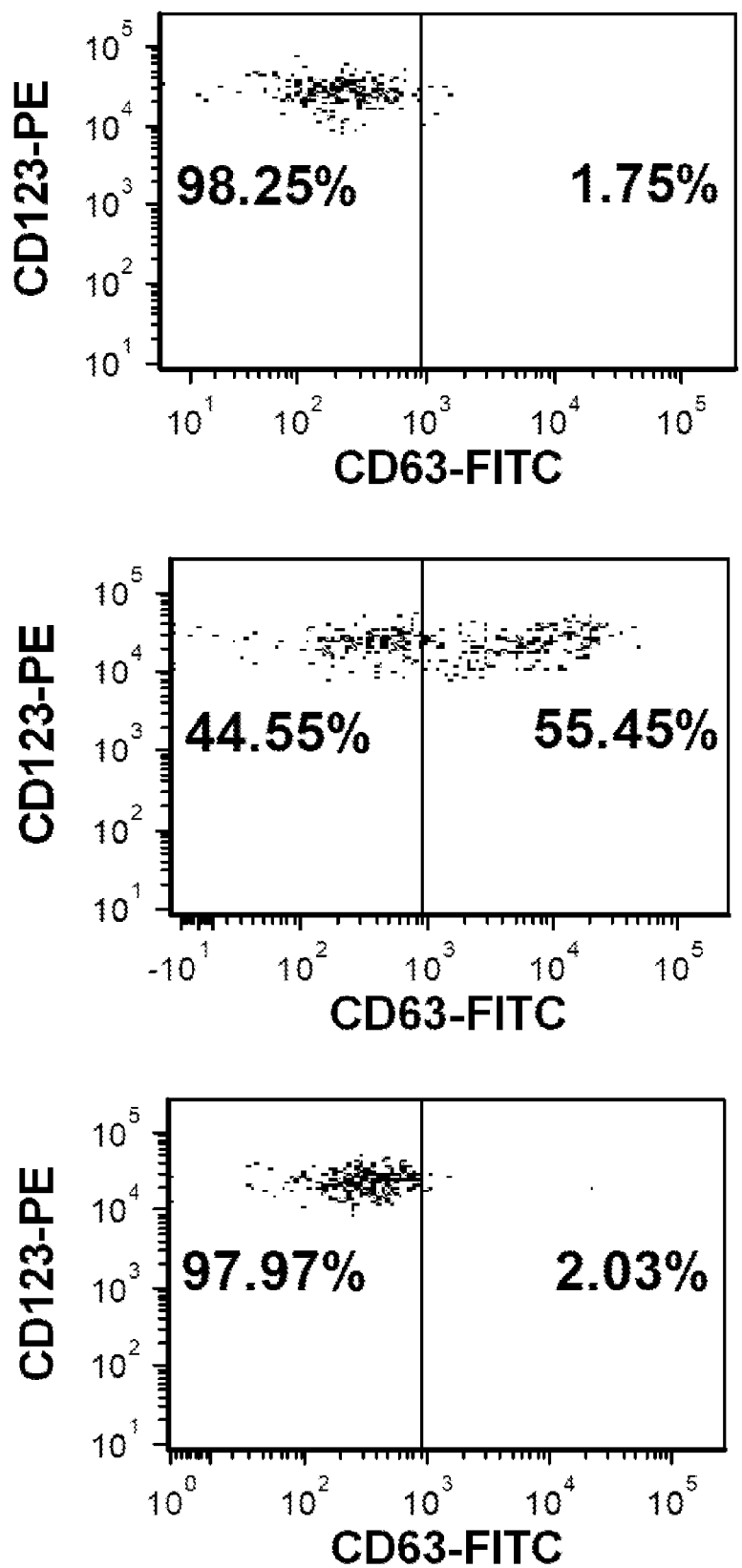
Figure 10:
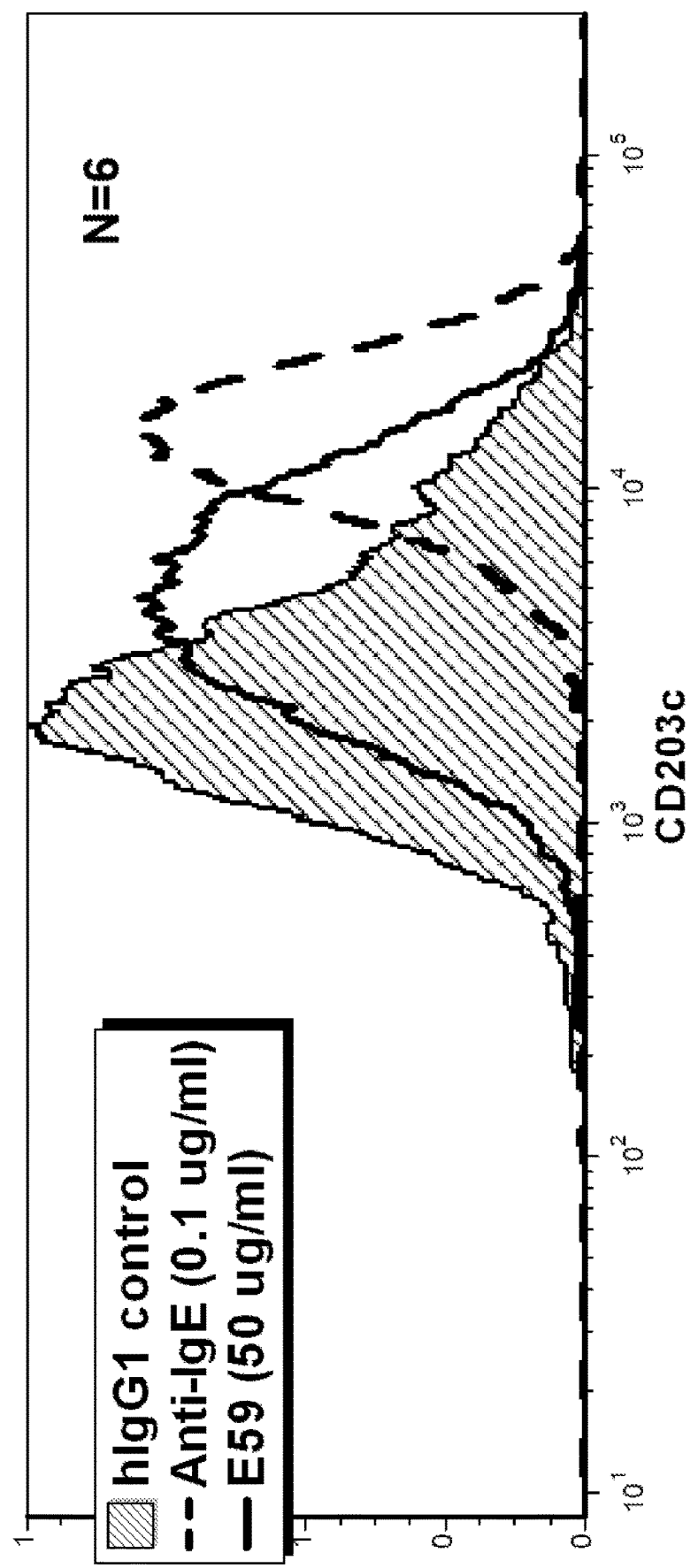
Figure 11:
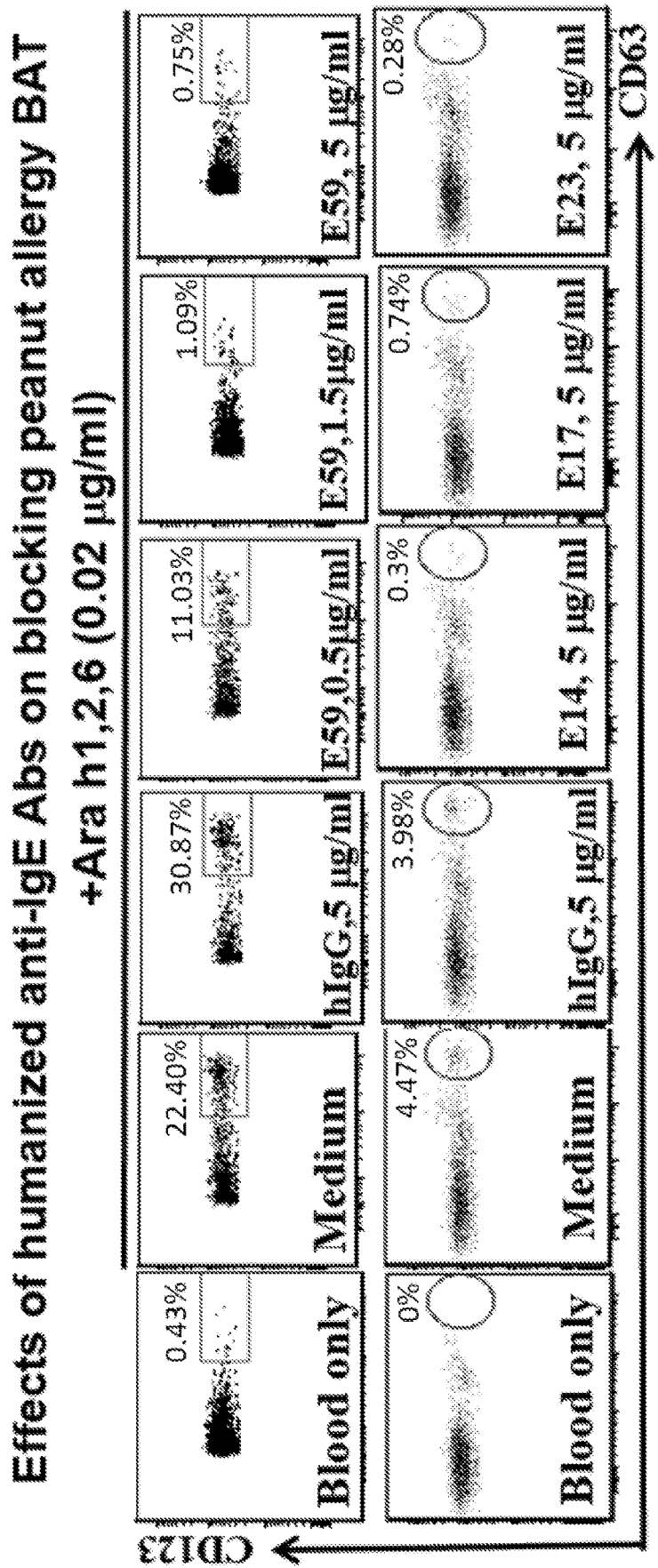
FIG. 11 to FIG. 14 show the therapeutic effects of hLAAIGEs on BAT.
Figure 12:
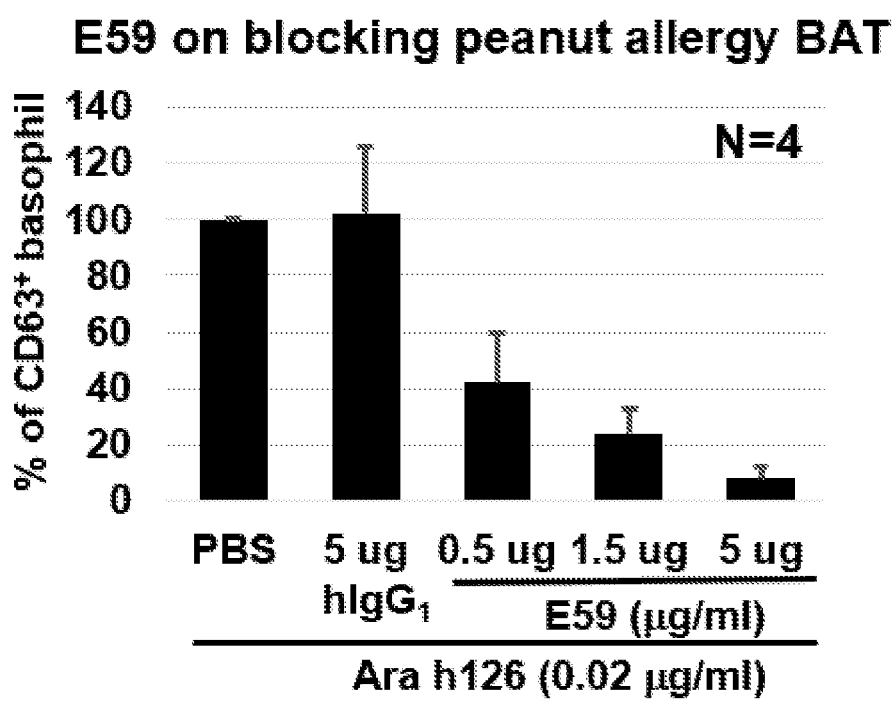
Figure 13:
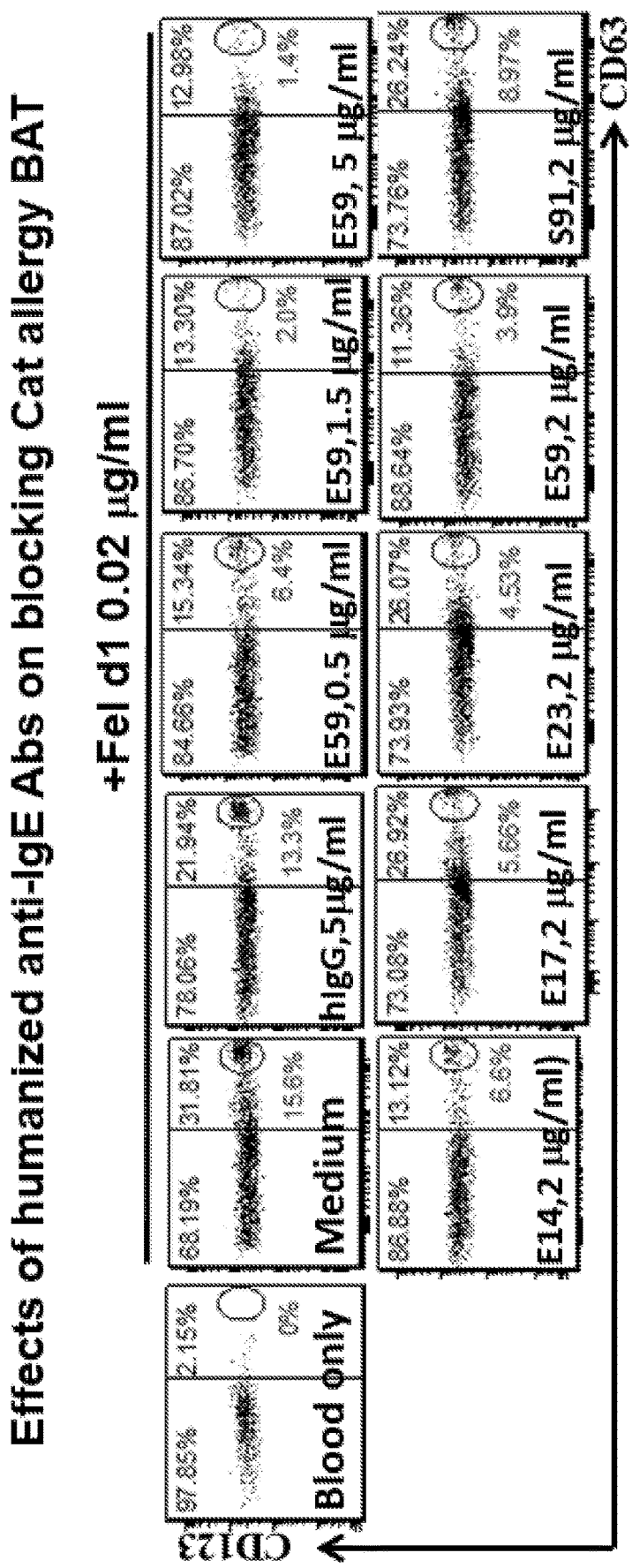
Figure 14:
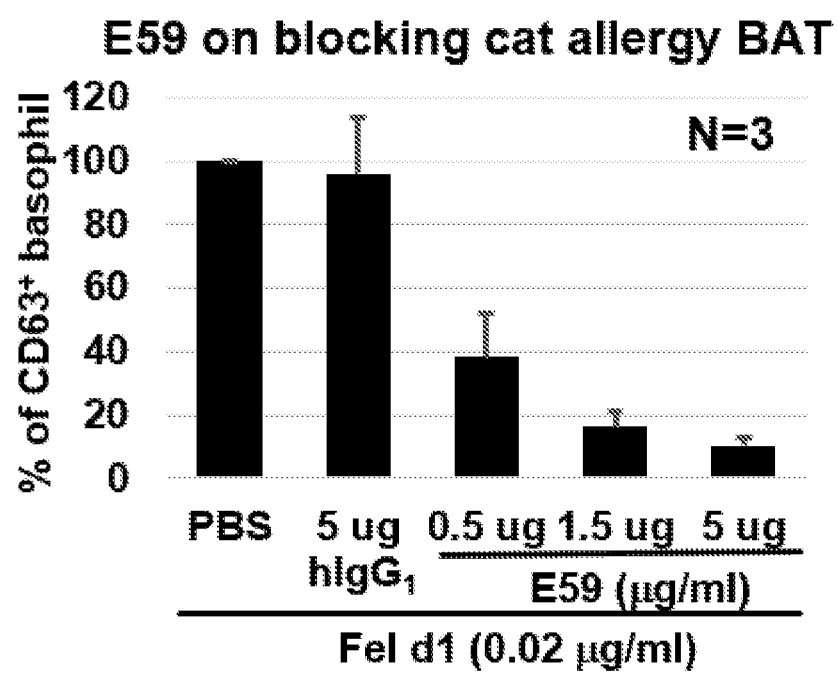

In contrast to polyclonal anti-IgE that induces basophil activation, E59 did not induce CD63 expression (FIG. 9). E59 also triggered weak CD203c expression (FIG. 10).

Therapeutic Effects of hLAAIGEs

Figure 15:
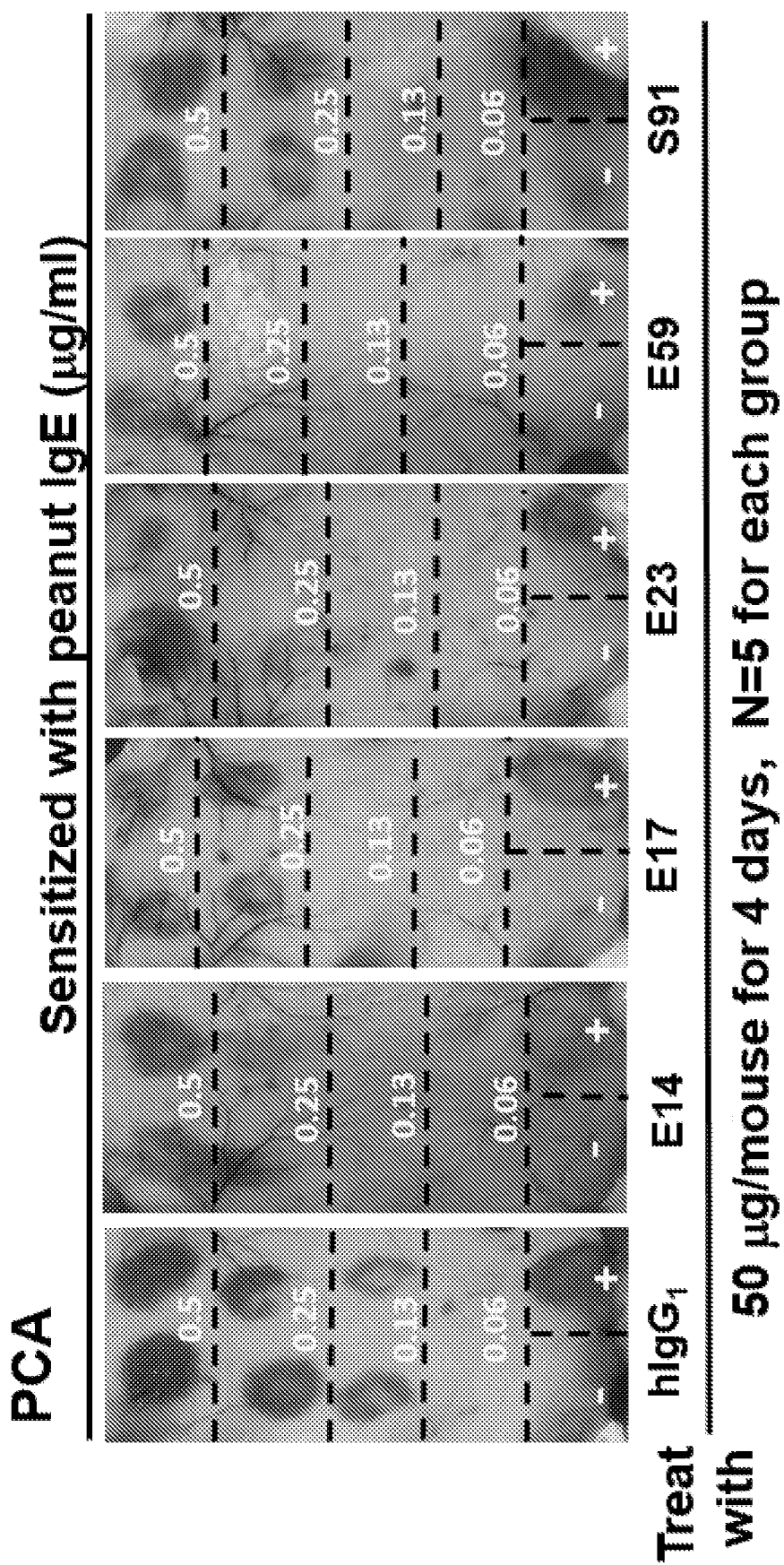
FIG. 15 to FIG. 19 show the therapeutic effects of hLAAIGEs in the hFcεRIα mouse model.
Figure 16:
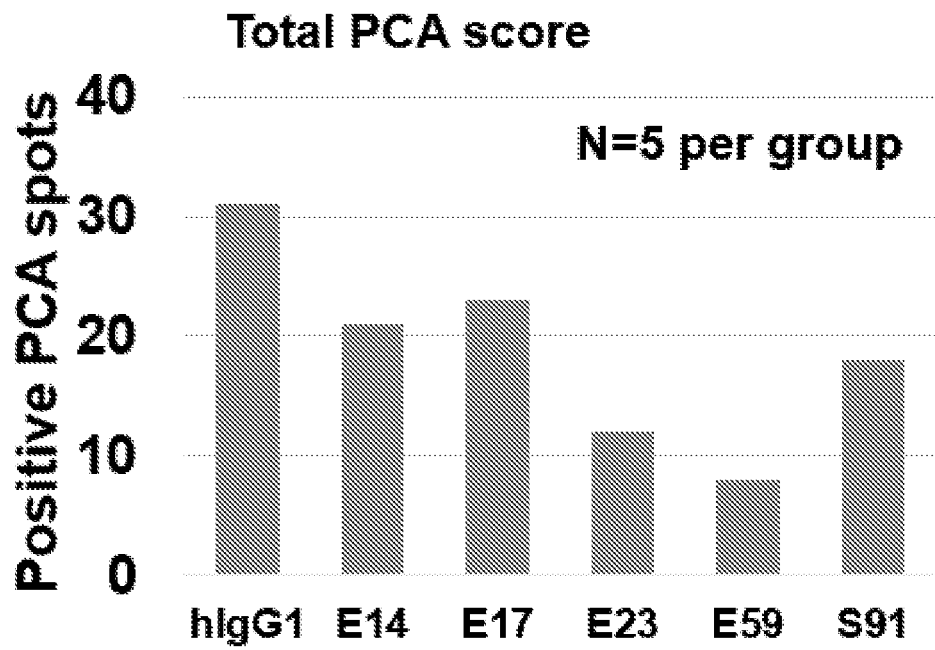
Figure 17:
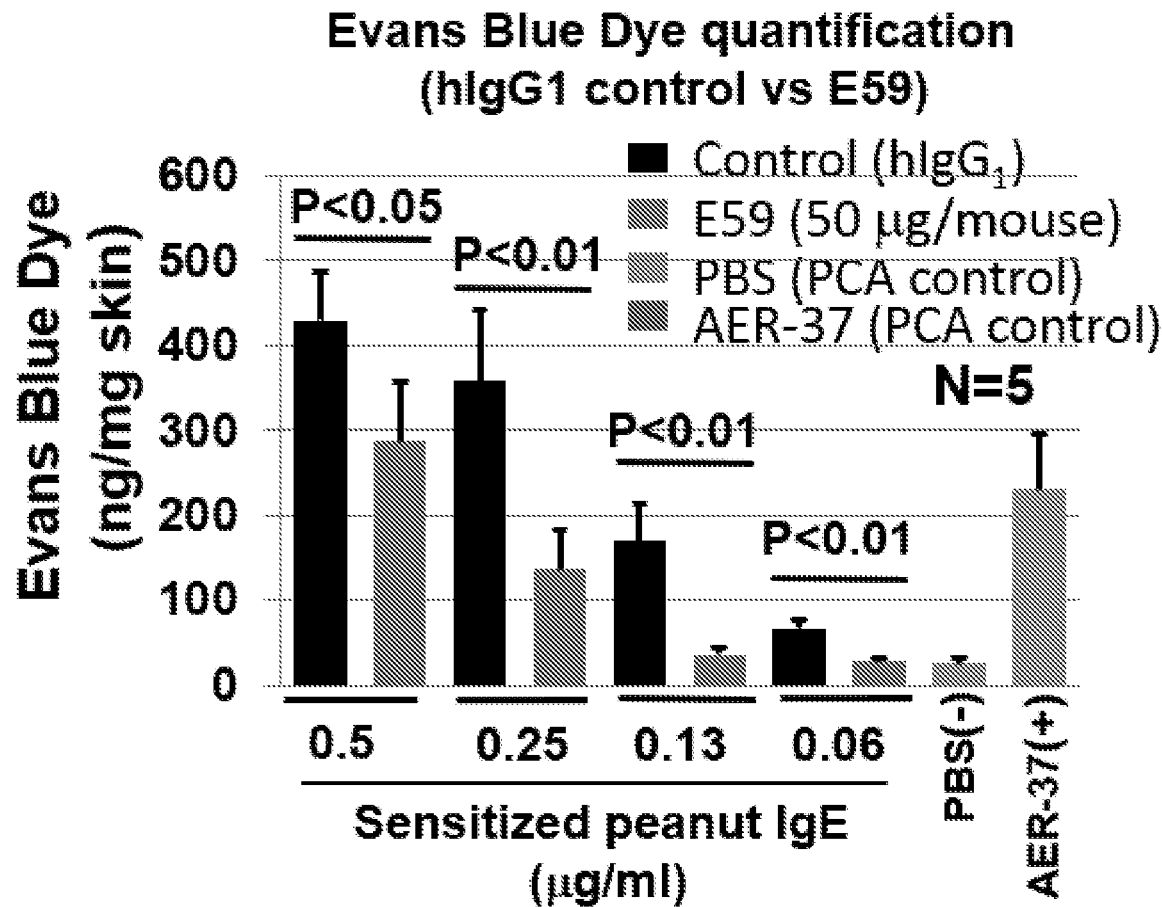
Figure 18:
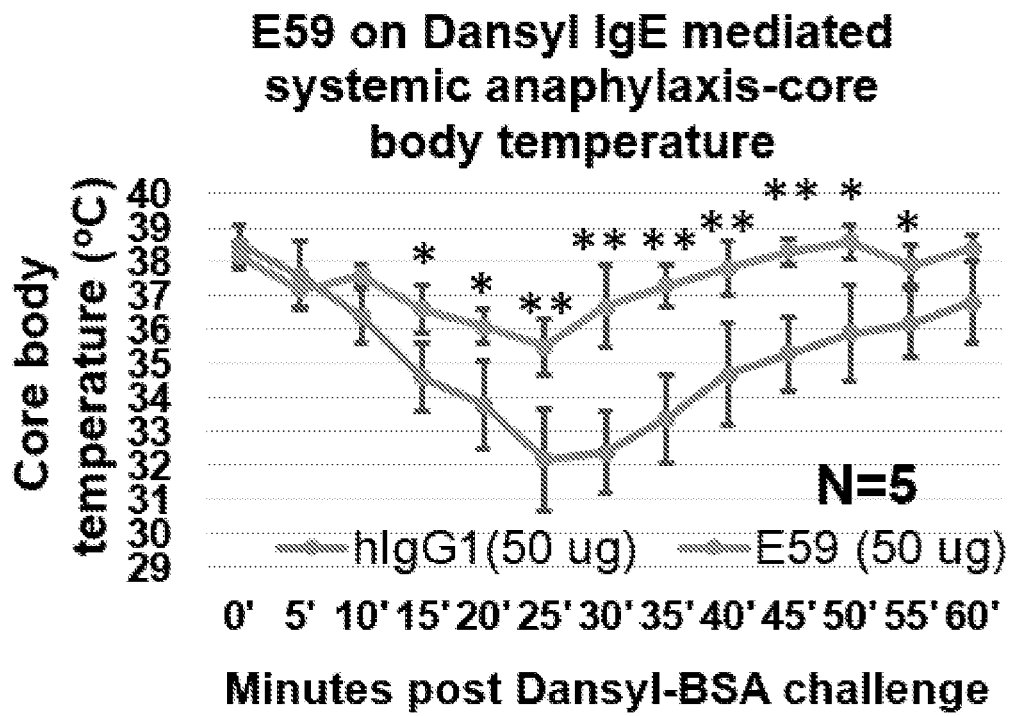
Figure 19:
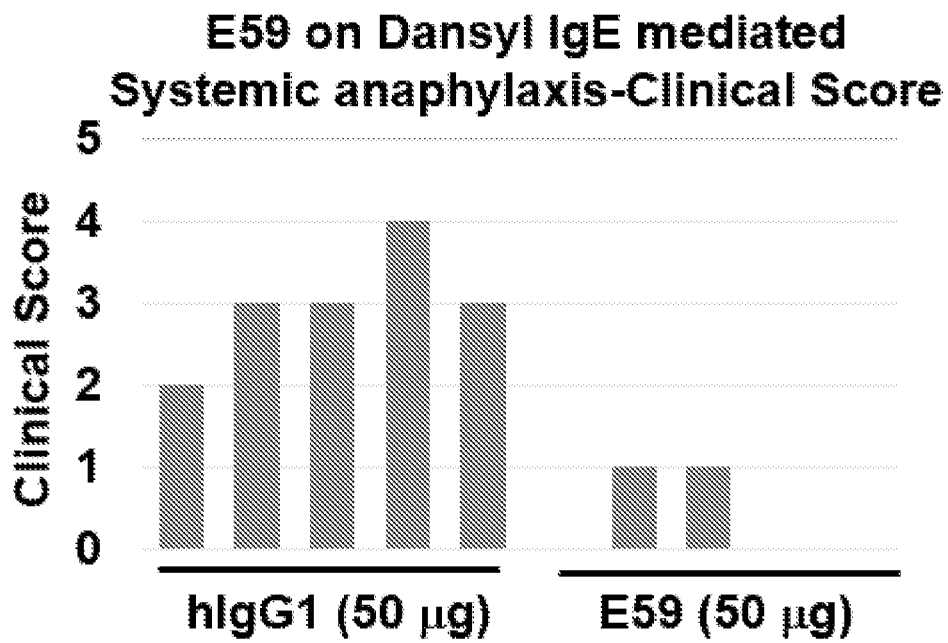

The peanut and cat allergic subjects' blood basophil activation test (BAT), the peanut allergic IgE mediated passive cutaneous anaphylaxis (PCA) and dansyl-IgE mediated systemic anaphylaxis in human FcεRIα transgenic mouse model were employed to assess the therapeutic effects of the hLAAIGEs. The BAT data presented in FIG. 11 to FIG. 14 showed that both peanut (FIG. 11 and FIG. 12) and cat (FIG. 13 and FIG. 14) allergic subjects BAT were profoundly suppressed by hLAAIGEs in a dose-dependent fashion, demonstrating that these selected hLAAIGEs exhibited profoundly blocking effects on both peanut and cat allergic BAT. In hFcεRIα Tg mouse model, the hLAAIGEs suppressed the peanut allergic IgE mediated PCA (FIG. 15 to FIG. 17) and dansyl-IgE mediated systemic anaphylaxis (FIG. 18 and FIG. 19).

Confirmation of the Mechanism of Action of hLAAIGEs

Figure 20:
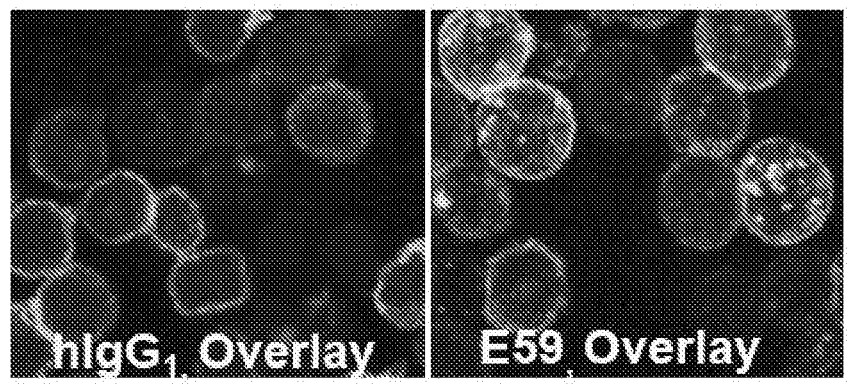
FIG. 20 and FIG. 21 show the internalization of E59 mediated surface IgE.
Figure 21:
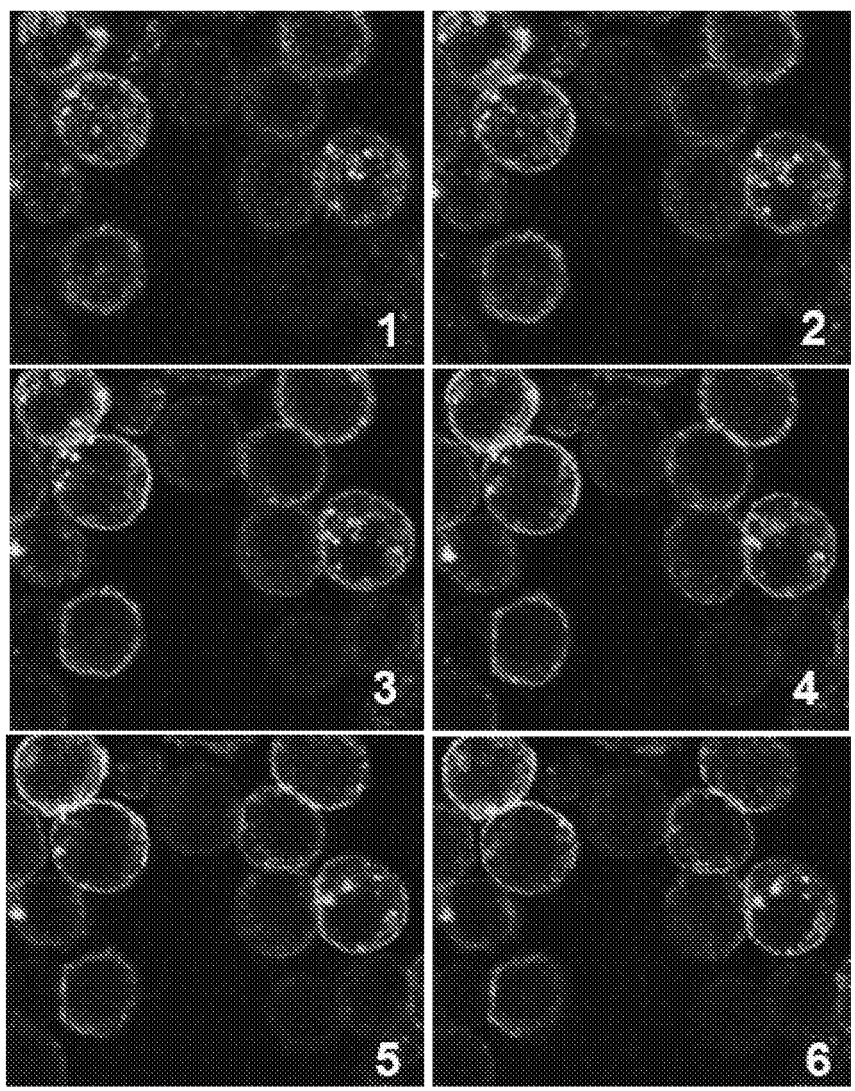

Because hLAAIGE clone E59 displayed an excellent safety profile and therapeutic effects, E59 was used to confirm the mechanism of action of the hLAAIGEs. With FITC-labeled human IgE sensitized hFcεRIα positive bone-marrow derived mast cells (BMMC), the IgE was mostly confined in the cell surface, with minimum intracellular green signal in the control hIgG1 treated BMMC. In contrast, the E59, but not the hIgG1 control, treated BMMC displayed significant intracellular IgE (green signal) that dispersed through all the levels in confocal sections (FIG. 20 and FIG. 21), demonstrating that E59, but not the control hIgG1, triggered the internalization of the surface IgE.

Figure 22:
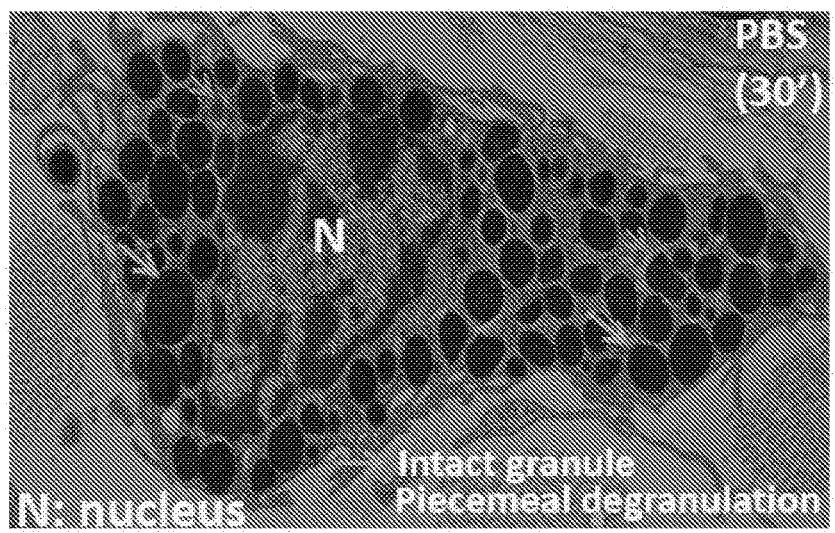
FIG. 22 to FIG. 24 show hLAAIGE induces piecemeal degranulation.
Figure 23:
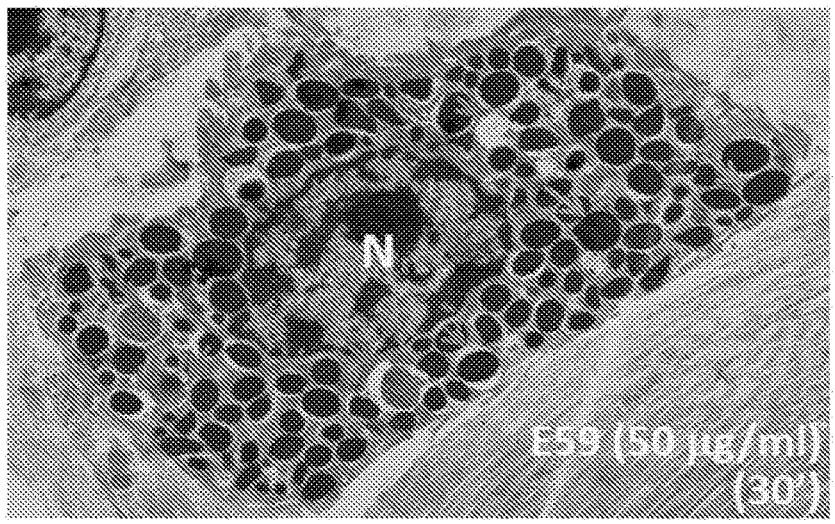
Figure 24:
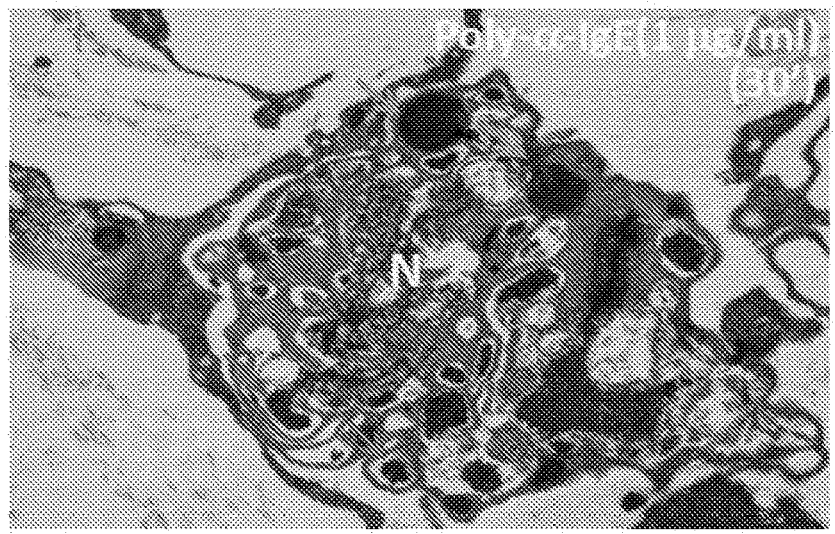

In electron microscopy examination of the phenotype of the granules of the skin mast cells, the PBS (as a control) treated skin mast cells mostly exhibited the intact electron-dense granules (green arrows) with minimal piecemeal degranulation (PD, red arrow) sign (FIG. 22), indicating that normal skin mast cells also underwent low level PD as the normal function of mast cell biology. The E59 treated mast cells (50 µg/ml for 30 minutes) displayed the apparently typical PD changes of the granules (FIG. 23), indicating that E59 induce PD-like change of the granules. As a positive control for anaphylactic degranulation, the skin mast cell treated with polyclonal anti-IgE antibody showed apparent anaphylactic degranulation that fused most of the intracellular granules, with residual amount of PD phenotype visible in electron microscopy (FIG. 24). Taken together, these data demonstrated that the hLAAIGE E59 triggers surface IgE internalization, and piecemeal degranulation.

Using BLAST sequence alignment tools and analysis was used to analyze the sequences of the humanized clones E59, E14, E17, E23, and S91. The lowest percent identity of the VH sequences (over the entire sequence) of the humanized clones is about 91%. Therefore, in some embodiments, hLAAIGEs according to the present invention have a VH sequence with a percent identity of at least about 90% up to 100%, preferably about 91% up to 100%, more preferably about 95% up to 100%, even more preferably about 97% up to 100%, and most preferably about 99% up to 100% to SEQ ID NO:1 as follows:

(SEQ ID NO: 1)
QVQLVQSGSELKKPGASVKVSCKASGYTFTNYGMNWVRQAPGQGLEW

MGWINTYTGEPTYADDFKGRFVFSLDTSVSTAYLQISSLKAEDTAVY

YCARGAASHTMDYWGQGTTVTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK

Between the humanized clones, the percent identity of portions of the VH sequences varied. For example, the percent identity of the humanized clones ranged from about 75% to 100% for the following portion of the VH sequence:

(SEQ ID NO: 2)
QVQLVQSGSELKKPGASVKVSCKASGYTFTNYGMNWVRQAPGQGLEW

MGWINTYTGEPTYADDFKGRFVFSLDTSVSTAYLQISSLKAEDTAVY

YCARGAASHTMDYWGQGTTVTVSSASTKGPSVFPLAPSSKSTSGGTA

ALGCLVKDYFPEPVTVSW

Therefore, in some embodiments, hLAAIGEs according to the present invention have a portion of a VH sequence having a percent identity of about 75% to about 100%, preferably about 80% to about 100%, more preferably about 90% to 100%, even more preferably about 95% to about 100%, and most preferably about 99% to 100% to SEQ ID NO:2.

Thus, in some embodiments, hLAAIGEs according to the present invention have a VH sequence having a percent identity of at least about 90% up to 100% to SEQ ID NO:1 and a portion of the VH sequence has a percent identity of about 75% to about 100%, preferably about 80% to about 100%, more preferably about 90% to 100%, even more preferably about 95% to about 100%, and most preferably about 99% to 100% to SEQ ID NO:2.

Four of five humanized clones have VL sequences (over the entire sequence) that have a percent identity of about 99% to:

(SEQ ID NO: 3)
DIVMTQSPDSLAVSLGERATINCRASQSVSTSSHSYMHWYQQKPGQP

PKLLIYYASNLESGVPDRFSGSGSGTDFTLTISSLQAEDVAVYYCQH

SWEIPWTFGQGTKLEIKRTVAAPSVFIFPPSDEQLKSGTASVVCLLN

NFYPREAKVQWKVDNALQSGNSQESVTEQDSKDSTYSLSSTLTLSKA

DYEKHKVYACEVTHQGLSSPVTKSFNRGEC

Therefore, in some embodiments, hLAAIGEs according to the present invention have a VL sequence with a percent identity of at least about 99% up to 100% to SEQ ID NO:3.

The fifth humanized clone, however, has a percent identity of about 65% to about 68% to the four humanized clones over a portion of the VL sequence, i.e., SEQ ID NO:4, as follows:

(SEQ ID NO: 4)
YMHWYQQKPGQPPKLLIYYASNLESGVPDRFSGS

Therefore, in some embodiments, hLAAIGEs according to the present invention have a portion of a VL sequence with a percent identity of at least about 65% up to 100% to SEQ ID NO:4. In some embodiments, hLAAIGEs according to the present invention have a portion of a VL sequence with a percent identity of about 65% to about 70% to SEQ ID NO:4. In some embodiments, hLAAIGEs according to the present invention have a portion of a VL sequence selected from the group consisting of:

(SEQ ID NO: 4)
YMHWYQQKPGQPPKLLIYYASNLESGVPDRFSGS (SEQ ID NO: 5)
YMHWYQQKPGQPPKLLIYYASNLKAGVPDRFSGS (SEQ ID NO: 6)
YVSWYQQHPGKAPKLMIYEVSKRPSGVPDRFSGS

In some embodiments, hLAAIGEs according to the present invention have a VL sequence with a percent identity of at least about 99% up to 100% to SEQ ID NO:3, and a VH sequence having a percent identity of about 75% to about 100%, preferably about 80% to about 100%, more preferably about 90% to 100%, even more preferably about 95% to about 100%, and most preferably about 99% to 100% to SEQ ID NO:2.

Further sequence analysis using BLAST alignments revealed that the hLAAIGEs according to the present invention comprise a VH chain that comprises DTAVYYCAR (SEQ ID NO:7), WVRQAPG (SEQ ID NO:8), GLEW (SEQ ID NO:9), and VTVSSA (SEQ ID NO:10), and a VL chain comprising LQAED (SEQ ID NO:11), AAPSV (SEQ ID NO:12), GTKL (SEQ ID NO:13), and RFSGS (SEQ ID NO:14).

In some embodiments, the hLAAIGEs according to the present invention comprise a VH chain having (X)$_{0-1}$VQLXQSG(X)$_5$PGXS(X)$_3$SCXASGXTF(X)$_6$ WVRQAPGXGLEW(X)$_3$I(X)$_4$G(X)$_3$Y(X)$_6$R(X)$_5$DXS(X)$_2$ T(X)$_6$SL(X)$_3$DTAVYYCAR(X)$_{9-11}$WGXGTXVTVSSAS (SEQ ID NO:15) and a VL chain having (X)$_4$TQ(X)$_{0-1}$PXS (X)$_3$SXG(X)$_3$TIXC(X)$_{2-3}$S(X)V(X)$_{9-11}$Q(X)$_2$PG(X)$_2$ PKLXIY(X)$_{2-4}$S(X)$_3$S(X)$_{2-4}$RFSGSXSG(X)$_4$ LTXSXLQAEDXAXYYC(X)$_{0-2}$Q(X)$_{6-8}$FGXGTKL(X)$_{3-7}$ AAPSV(X)$_2$FPPSXE XL(X)$_4$A(X)$_2$VCL(X)$_3$FYP(X)$_4$ VXWKXD(X)$_{5-6}$G(X)$_{1-3}$E(X)$_2$T(X)$_8$Y(X)$_2$SSXLXL(X)$_7$ H(X)$_2$YXC XVTHXG(X)$_{0-2}$SXVXK(X)$_5$EC(X)$_{0-1}$ (SEQ ID NO:16), wherein each X is independently any amino acid.

In some embodiments, the hLAAIGEs according to the present invention comprise a VH chain that comprises VQLX1QSG (SEQ ID NO:17), PGX2SX3X4X5SCX6ASGX7TF (SEQ ID NO:18), WVRQAPGX8GLEW (SEQ ID NO:19), WGX9GTX10VTVSSA (SEQ ID NO:20), SLX11X12X13DTAVYYCAR (SEQ ID NO:21), and RX14X15X16X17X18DX19SX20X21T (SEQ ID NO:22), wherein X1 to X21 are each independently any amino acid. In some embodiments, X1 is V or G, preferably V, X2 is A or R, preferably A, X3 is L or V, preferably V, X4 is K or R, preferably K, X5 is L or V, preferably V, X6 is A or K, preferably K, X7 is F or Y, preferably Y, X8 is K or Q, preferably Q, X9 is R or Q, X10 is L or T, X11 is T, K, or R, X12 is A or S, X13 is E or D, X14 is F or V, X15 is T or V, X16 is I, F, or M, X17 is S or T, X18 is L, R, or T, X19 is N or T, preferably T, X20 is K, T, or V, and X21 is N or S, preferably S. In some embodiments, the VH chain comprises at least 10, 20, 30, 40, or 50 consecutive amino acid residues of (SEQ ID NO: 23)
TKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLT

VLHQDWLNGKEYKCKVSNKALPAPIEKTISKAKGQPREPQVYTLPPS

RDELTKNQVSLTCLVKGFYPSDIAVEWESNGQPENNYKTTPPVLDSD

GSFFLYSKLTVDKSRWQQGNVFSCSVMHEALHNHYTQKSLSLSPGK.

In some embodiments, the hLAAIGEs according to the present invention comprise a VL chain that comprises RFSGSX22SG (SEQ ID NO:24), LTX23SX24LQAEDX254AX26YY (SEQ ID NO:25), FGX27GTKL (SEQ ID NO:26), AAPSVX28X29FPPSX30EX31L (SEQ ID NO:27), AX32X33VCLX34X35X36FYP (SEQ ID NO:28), HX37X38YX39CX40VTHX41G (SEQ ID NO:29), PX42SX43X44X45SX45GX47X48X49TIX50C (SEQ ID NO:30), QX51X52PGX53X54PKLX55 IY (SEQ ID NO:31), wherein X22 to X55 are each independently any amino acid. In some embodiments, X22 is G or K, X23 is I or V, X24 is G or S, X25 is E or V, X26 is D or V, X27 is G, S, or Q, X28 is F or T, X29 is I or L, X30 is D or S, X31 is E or Q, X32 is S or T, X33 is L or V, X34 is I or L, X35 is N or S, X36 is D or N, X37 is K or R, X38 is S or V, X39 is A or S, X40 is E or Q, X41 is E or Q, X42 is A, D, or P, X43 is A, L, or V, X44 is A or S, X45 is G or V, X46 is L or P, X47 is E or Q, X48 is R or S, X49 is A, I, or V, X50 is N or S, X51 is H or Q, preferably Q, X52 is H or K, X53 is K or Q, X54 is A or P, and X55 is L or M. In some embodiments, the VL chain comprises DIVMTQSPDSLAVSLGERATINCRASQSVSTSX56HSY MHWYQQKPGQPPKLLIYYASNLX 57X58GVPDRFSGSGSGTDFTLTISSLQAEDVAVYYCQ HSWEIPWTFGQGTKLEIKRTVAA PSVFIFPPSD-EQLKSGTASVVCLLNNFYPREAKVQWKVD-NALQSGNSQESVTEQDSKDST YSLSSTLTL-SKADYEKHKVYACEVTHQGLSSPVTKSFNRGEC (SEQ ID NO:32), wherein X56 is A or S, X57 is E or K, X58 is A or S.

In some embodiments, the hLAAIGEs according to the present invention bind human IgE with a low affinity of about $1 \times 10^{-5}$ M to about $1 \times 10^{-9}$ M Kd (as measured by the Biacore method). Specifically, the hLAAIGEs as exemplified herein, bind human IgE with an affinity of about $5 \times 10^{-5}$ M to about $7 \times 10^{-8}$ M Kd. In some embodiments, the IgE epitope recognized by the hLAAIGEs comprises at least 10 consecutive amino acid residues of NPRGVSAY-LSRPSPFDLFIRKSPTITCLVVD-LAPSKGTVNLTWSRASGKPVNHSTRKEEK QRNGTLTVTSTLPVGTRDWIEGETYQCRVTHPHL-PRALM (SEQ ID NO:33). In some embodiments, the IgE epitope recognized by the hLAAIGEs comprises, consists essentially of, or consists of one or more of the following sequences YQCRVTHPHLPR (SEQ ID NO:34), YQCRVTHPHLPRALM (SEQ ID NO:35), ETYQCRVTHPHLPR (SEQ ID NO:36), ETYQCRVTHPHLPRALM (SEQ ID NO:37), PRGVSAY-LSR (SEQ ID NO:38), NPRGVSAYLSR (SEQ ID NO:39), PSPFDLFIRK (SEQ ID NO:40), RPSPFDLFI (SEQ ID NO:41), RPSPFDLFIRK (SEQ ID NO:42), PRGVSAY-LSRPSPFDLFI (SEQ ID NO:43), PRGVSAYLSRPSPFDL-FIRK (SEQ ID NO:44), and NPRGVSAYLSRPSPFDL-FIRK (SEQ ID NO:45).

In some embodiments, hLAAIGEs according to the present invention inhibit activation (e.g., degranulation) of effector cells that express FcεRI, such as mast cells, basophils, eosinophils, and the like. In some embodiments, hLAAIGEs according to the present invention inhibit activation (e.g., degranulation) of an effector cell by binding to FcεRI-bound IgE. In some embodiments, hLAAIGEs according to the present invention—upon binding to receptor-bound IgE—do not themselves result in cell activation (e.g., do not result in crosslinking of neighboring IgE-FcεRI complexes). In some embodiments, hLAAIGEs according to the present invention specifically bind to circulating and receptor-bound IgE, binds to IgE with low affinity and inhibits activation of cells that express the high affinity IgE receptor (FcεRI). In some embodiments, hLAAIGEs according to the present invention reduce the amount of IgE bound to the surface of cells that express the high affinity IgE receptor (FcεRI). In some embodiments, hLAAIGEs according to the present invention reduce the amount of surface-bound IgE by triggering internalization of IgE (e.g., which may be present as an IgF-FcεRI complex) by the effector cell (e.g., a basophil, mast cell, eosinophil, and/or the like). In some embodiments, hLAAIGEs according to the present invention reduce the amount of high affinity IgE receptor (FcεRI) on the surface of cells (e.g., effector cells). Such hLAAIGEs may, for example, reduce the amount of surface FcεRI by triggering internalization of FcεRI (e.g., which may be present as an IgE-FcεRI complex) by the effector cell (e.g., a basophil, mast cell, eosinophil, and/or the like).

In some embodiments, hLAAIGEs according to the present invention activates piecemeal degranulation in effector cells (e.g., a basophil, mast cell, eosinophil, and/or the like). In "piecemeal degranulation", granule proteins are mobilized and released by a mechanism that: (i) does not involve the wholesale secretion of granule content like in exocytosis; (ii) leaves behind partially empty membrane-bound granule chambers; and (iii) depends on the trafficking of small vesicles. See, e.g., Bandeira-Melo & Weller (2005) Mem. Inst. Oswaldo Cruz 100 (Supp. I):73-81. Piecemeal degranulation is associated with allergic/effector cell desensitization, but not anaphylactic degranulation. In some embodiments, hLAAIGEs according to the present invention activate piecemeal degranulation, but not anaphylactic degranulation, in the effector cells (e.g., basophils, mast cells, eosinophils, and/or the like). Suitable approaches for determining whether an antibody activates piecemeal degranulation are known and include, e.g., assaying for upregulation of CD203c in cells exposed to the antibody. Specifically, the upregulation of CD203c on ex vivo basophils can serve as a biomarker for piecemeal degranulation. CD203c upregulation can also serve as a biomarker of therapeutic potential, whereas the inability to trigger CD63 expression of hLAAIGE from basophils could be used to monitor the safety of hLAAIGEs.

In some embodiments, hLAAIGEs according to the present invention that bind to circulating and receptor-bound IgE also bind to membrane IgE (or "mIgE"). IgE exists in a B cell membrane-anchored form (membrane IgE) and in several secreted forms. See Zhang, et al. (1994) J. Biol. Chem. 269:456-462. These distinct forms are splice variants. The main secreted form of IgE is generally a shorter form with the Fc region essentially terminating at the Cε4 domain, whereas membrane IgE includes additional C-terminal residues including the peptides encoded by the exons known as M1/M1' and M2. An anti-IgE hLAAIGE according to the present invention may bind to any epitope of mIgE that is also available for binding in circulating and receptor-bound IgE. For example, the anti-IgE antibody may bind to an epitope in any of the Cε1, Cε2, Cε3, or Cε4 domains available for binding in circulating, receptor-bound and membrane IgE. In binding to membrane IgE, the antibody may inhibit IgE production, e.g., by inhibiting the maturation of IgE-expressing B cells.

The epitope of hLAAIGEs according to the present invention may be present in any suitable region of IgE, so long as the epitope is accessible for binding when the IgE is receptor-bound (e.g., bound to FcεRI or FcεRII (CD23)). Details regarding the structure of IgE are found in Zheng, et al. (Biochemistry (1991) 30:9125-9132), Wan, et al. (Nature Immunology (2002) 3:681-686) and Gould and Sutton (Nature Reviews Immunology (2008) 8:205-217), the disclosures of which are incorporated herein by reference in their entireties for all purposes. The heavy ε-chain of IgE may be divided into five domains, which from C-terminus to N-terminus include: the Cε4 domain, the Cε3 domain, the Cε2 domain, the Cε1 domain, and the variable heavy chain region/domain (VH). An antibody according to the present disclosure may recognize an epitope, e.g., in the Cε4 domain, the Cε3 domain, the Cε2 domain, or the Cε1 domain of IgE. In some embodiments, hLAAIGEs according to the present invention do not recognize an epitope in the Cε3 domain of human IgE.

Two IgE-epitopes bound by five hLAAIGEs were mapped with CLIP technology (Pepscan Inc). The antibodies were tested using a Pepscan array containing linear and single loop epitope mimics. Linear epitope candidates were determined for E17, E59, and S91. The IgE epitope bound by H6.2 was unable to be determined. An HRP conjugate used for the detection was tested as a negative control and weakly bound to few peptides on the array. Antibodies E17 and E59 generally yielded very similar binding profiles with one dominant peak of relatively low intensity. Noteworthy, for both antibodies signal intensities recorded with single loop peptides containing sequence YQCRVTHPHLPRALM (SEQ ID NO:35) were generally higher than signal intensities recorded with their linear analogs. Antibody S91 repeatedly displayed binding profiles with multiple peaks of similar signal intensities. Such results indicate recognition of discontinuous epitopes, e.g., a conformational epitope. However, recorded data allowed proposing three epitope candidates, one of which partially overlaps with the epitope identified for E17 and E59.

In some embodiments, hLAAIGEs according to the present invention specifically bind to circulating and receptor-bound IgE and inhibits antigen-mediated (e.g., allergen-mediated) activation (e.g., degranulation) of effector cells that express the high affinity IgE receptor (FcεRI), such as basophils, mast cells, and/or eosinophils. For example, the antibody can inhibit effector cell activation by 5% or more, 10% or more, 15% or more, 20% or more, 25% or more, 30% or more, 40% or more, 50% or more, 60% or more, 70% or more, 80% or more, 90% or more, or 95% or more, compared to the degree of effector cell activation in the absence of the antibody. Effector cell activation may be determined using any convenient approach for the effector cell of interest, including the basophil activation test (BAT) and Passive Cutaneous Anaphylaxis (PCA) assay, described below in more detail in the Examples section. In some embodiments, hLAAIGEs according to the present invention block or reduce effector cell activation when present at concentrations of from 0.01-5 μg/ml, such as from 0.03-2.5 μg/ml, e.g., 0.05-1 μg/ml.

Figure 25:
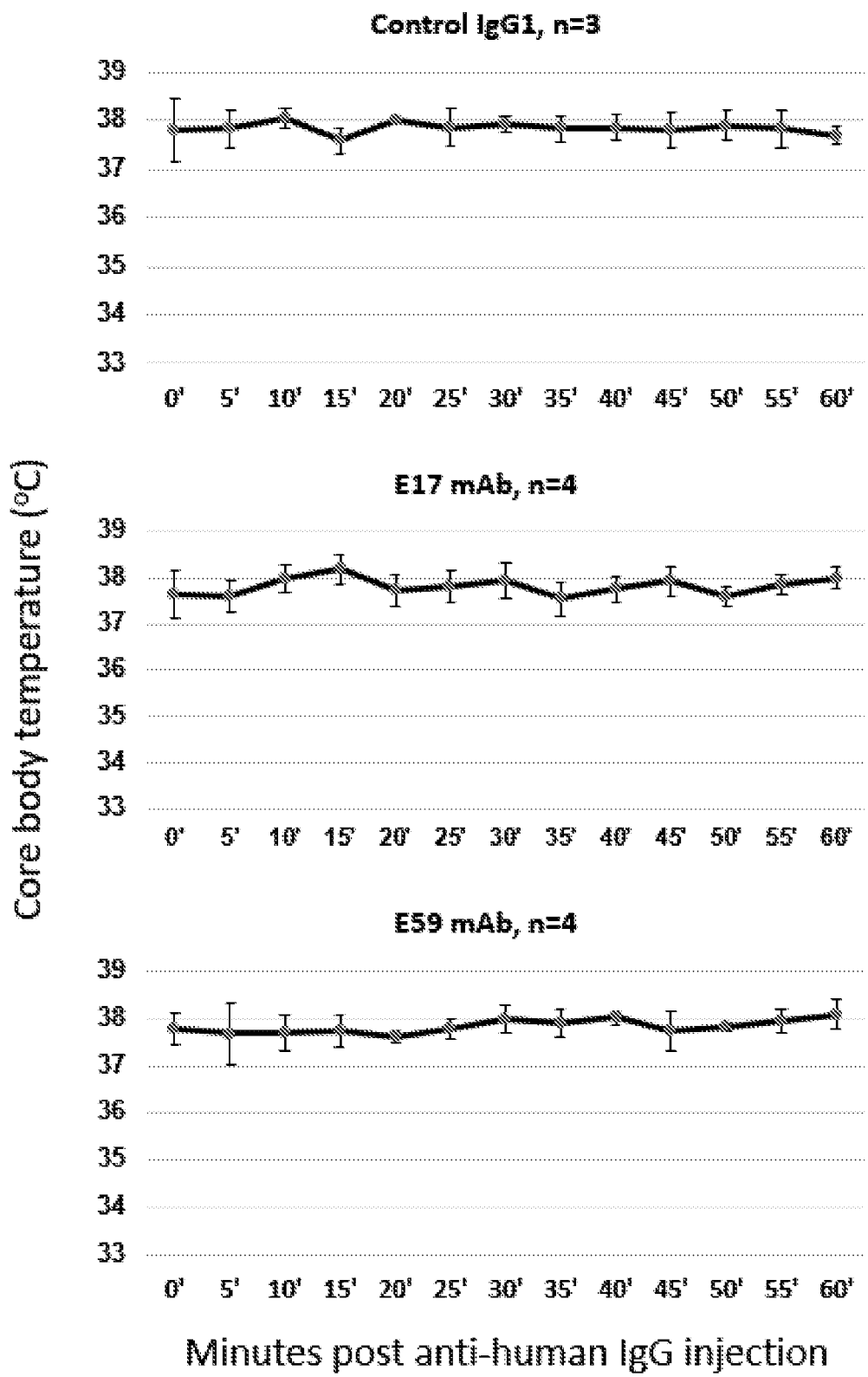
FIG. 25 are graphs showing that crosslinking of hLAAIGEs, e.g., E17 and E59, with anti-human IgG does not trigger systemic anaphylaxis, as measured by fall in core body temperature, in hFcεRIα Tg mice. hFcεRIα Tg mice were sensitized with 50 μg IgE i.p. for 16 hours followed by i.p. injection of 50 μg control human IgG, E17, or E59. Two hours later, the mice were i.v. challenged with 50 μg rabbit anti-human IgG, and their rectal temperatures were recorded at 5-minute intervals.

To test whether crosslinking, i.e., anti-hLAAIGE/hLAAIGE complexes, would induce activation/adverse reactions, hFcεRIα Tg mice were loaded systemically with human IgE and treated systemically with hLAAIGE (a human IgG1). The animals were then given polyclonal anti-human IgG to cross link the hLAAIGE. No systemic reactivity occurred (FIG. 25), i.e., crosslinking did not induce anaphylactic degranulation. Additionally, human mast cells were treated in vitro with hLAAIGE or hLAAIGE that had been incubated/crosslinked with anti-human IgG and no evidence of activation or mediator release was observed under either condition. This data demonstrates that the hLAAIGEs lack the capacity to trigger degranulation/mediator release from the allergic effector cells in vitro, ex vivo, and in vivo.

Therefore, in some embodiments, hLAAIGEs according to the present invention specifically bind to circulating and receptor-bound IgE, and reduces or eliminates antigen-mediated (e.g., allergen-mediated) crosslinking of neighboring IgE/FcεRI complexes on the surface of an effector cell, e.g., such as a basophil, mast cell or eosinophil. For example, the antibody may reduce crosslinking of neighboring IgE/FcεRI complexes by 5% or more, 10% or more, 15% or more, 20% or more, 25% or more, 30% or more, 40% or more, 50% or more, 60% or more, 70% or more, 80% or more, 90% or more, or 95% or more, compared to the degree of IgE/FcεRI complex crosslinking in the absence of the antibody.

In some embodiments, hLAAIGEs according to the present invention reduce the amount of IgE on the surface of cells that express FcεRI by 10% or more, 20% or more, 30% or more, 40% or more, 50% or more, 60% or more, 70% or more, 80% or more, 90% or more, or 95% or more, as compared to the amount of IgE bound to the surface of the cells in the absence of the antibody. In some embodiments, hLAAIGEs according to the present invention can reduce the amount of IgE bound to the surface of the cells when present at a concentration of from 0.01-10 μg/ml, such as 0.05-5 μg/ml, e.g., 0.1-2 μg/ml.

Figure 26:
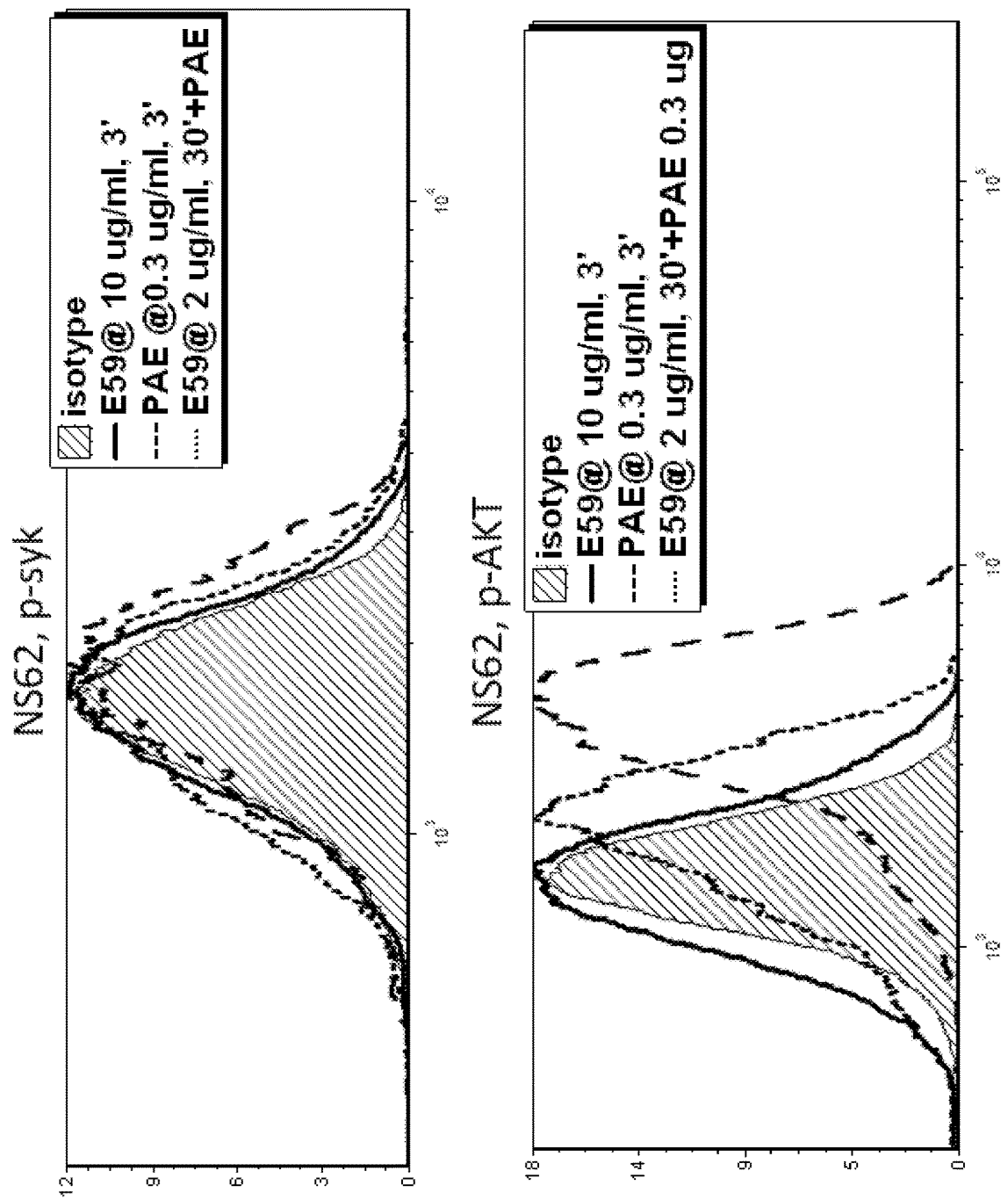
FIG. 26 are graphs showing that hLAAIGEs, e.g., E59, induces partial FcεRI signaling that attenuates full-FcεRI signaling.
Figure 26:
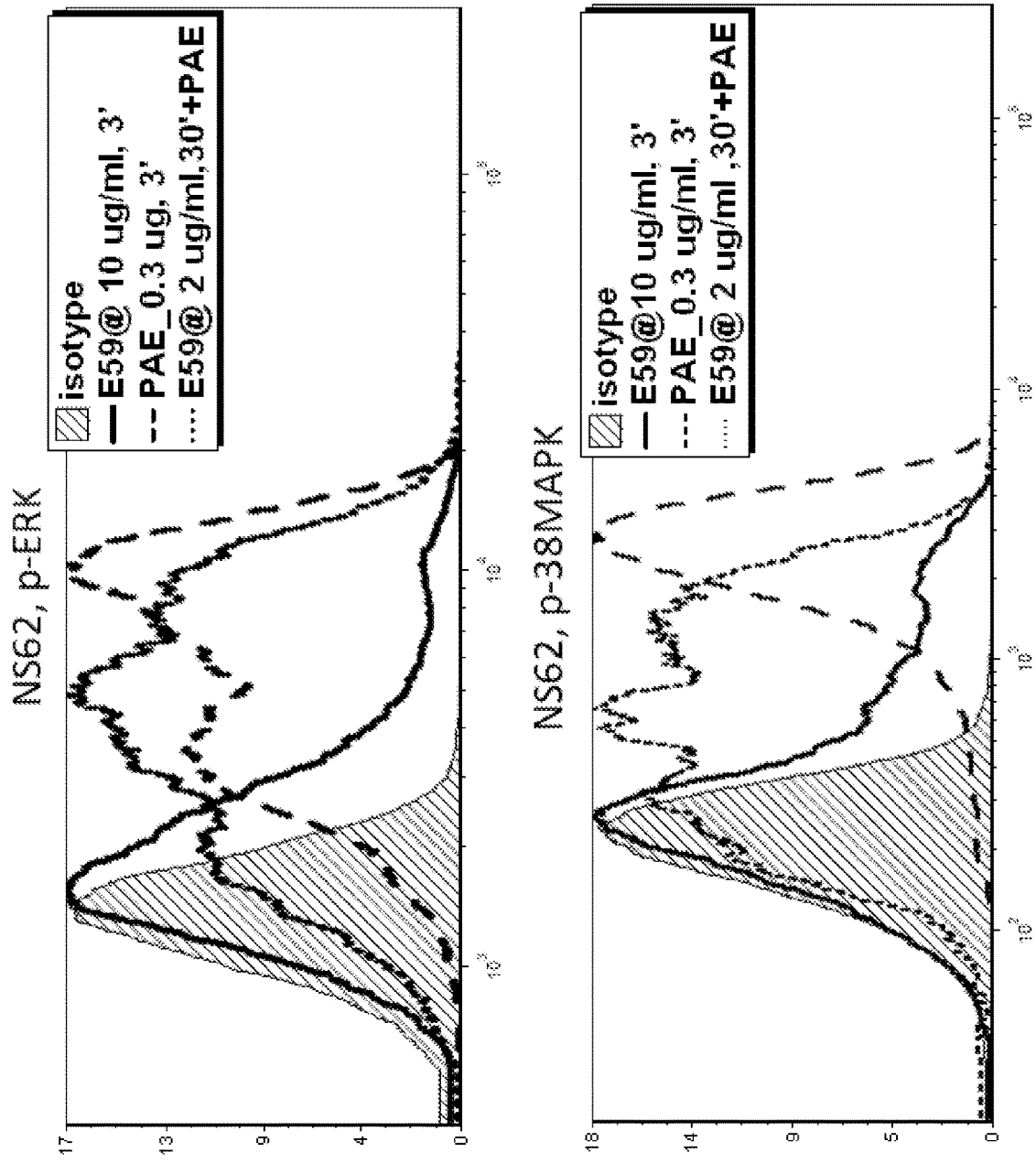

In some embodiments, hLAAIGEs according to the present invention induce partial FcεRI pathway signaling that functions as antagonist to attenuate full FcεRI activation signaling like that resulting from administration with a low dose of allergen. See, e.g., Rotiroti, et al. (2012) J Allergy Clin Immunol. 130:918. Proper phosphorylation of syk, ERK, p38-MAPK, and AKT is associated with FcεRI activation signaling leading to anaphylactic degranulation. E59 was found to induce partial FcεRI pathway signaling that attenuates FcεRI activation signaling. E59, at relatively high concentration (10-50 μg/ml), weakly induce phosphorylation of syk, ERK, p38-MAPK, and AKT, compared with that of polyclonal anti-IgE Ab induced phosphorylation (E59@10 μg/ml, FIG. 26). Human basophils, when pretreated with E59 for 30 minutes, show an attenuated phosphorylation of syk, ERK, p38-MAPK, and AKT (PAE vs E59@2 μg/ml, FIG. 26) when subsequently stimulated with the high-affinity polyclonal anti-IgE antibody. This attenuated phosphorylation was not observed when the basophils were concurrently stimulated with E59 and the high affinity polyclonal anti-IgE antibody. E59 induced partial activation of FcεRI signaling that rendered these allergy effector cells unresponsive to later full activation via FcεRI cross-linking.

Therefore, in some embodiments, one or more hLAAIGEs according to the present invention are administered to subjects to attenuate FcεRI activation signaling and/or anaphylactic degranulation. In some embodiments, one or more hLAAIGEs according to the present invention are administered to subjects to attenuate phosphorylation of syk, ERK, p38-MAPK, and/or AKT.

HLAAIGEs according to the present invention may include one or more (e.g., one or two) heavy chain variable regions ($V_H$) and/or one or more (e.g., one or two) light chain variable regions ($V_L$), or sub-fragments thereof capable of binding to an epitope. The $V_H$ and $V_L$ regions can be further subdivided into complementarity determining regions (CDRs), which are regions of hypervariability, interspersed with framework regions (FRs), which are regions that are more conserved than CDRs. The extent of the CDRs and FRs have been precisely defined (see, Kabat, et al. (1991) Sequences of Proteins of Immunological Interest, Fifth Edition, U.S. Department of Health and Human Services, NIH Publication No. 91-3242; Chothia, et al. (1987) J. Mol. Biol. 196: 901-917). A $V_H$ can comprise three CDRs and four FRs arranged from N-terminus to C-terminus in the following order: FR1, CDR1, FR2, CDR2, FR3, CDR3, FR4. Similarly, a $V_L$ can comprise three CDRs and four FRs arranged from N-terminus to C-terminus in the following order: FR1, CDR1, FR2, CDR2, FR3, CDR3, FR4.

The $V_H$ or $V_L$ chain of an antibody can further include all or part of a heavy or light chain constant region, to thereby form a heavy or light immunoglobulin chain, respectively. In some embodiments, hLAAIGEs are tetramers of two heavy and two light chains, wherein the heavy and light chains are interconnected by, for example, disulfide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. In some embodiments, hLAAIGEs according to the present invention are IgG (e.g., an IgG1) isotype antibodies.

The term "immunoglobulin" may refer to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon, and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g., gamma (encoding about 330 amino acids). In some embodiments, hLAAIGEs according to the present invention comprise a full-length immunoglobulin heavy chain and a full-length immunoglobulin light chain.

In some embodiments, hLAAIGEs according to the present invention do not comprise a full-length immunoglobulin heavy chain and a full-length immunoglobulin light chain, but instead comprise antigen-binding fragments of a full-length immunoglobulin heavy chain and/or a full-length immunoglobulin light chain. In some embodiments, the antigen-binding fragments are contained on separate polypeptide chains; in other embodiments, the antigen-binding fragments are contained within a single polypeptide chain. For example, in some embodiments, the IgE binding fragment specifically binds to circulating and receptor-bound IgE, binds to IgE with low affinity, and inhibits activation of cells that express the high affinity IgE receptor (FcεRI). According to some embodiments, the IgE binding fragment specifically binds to circulating and receptor-bound IgE, and inhibits activation of cells that express the high affinity IgE receptor (FcεRI).

Examples of antigen-binding fragments include (i) a Fab fragment (a monovalent fragment consisting of the $V_L$, $V_H$, CL and CH1 domains); (ii) a F(ab')$_2$ fragment (a bivalent fragment comprising two Fab fragments linked by a disulfide bridge at the hinge region); (iii) a Fd fragment (consisting of the $V_H$ and CH1 domains); (iv) a Fv fragment (consisting of the $V_H$ and $V_L$ domains of a single arm of an antibody); (v) a dAb fragment (consisting of the $V_H$ domain); (vi) an isolated CDR; (vii) a single chain Fv (scFv) (consisting of the $V_H$ and $V_L$ domains of a single arm of an antibody joined by a synthetic linker using recombinant means such that the $V_H$ and $V_L$ domains pair to form a monovalent molecule); (viii) diabodies (consisting of two scFvs in which the $V_H$ and $V_L$ domains are joined such that they do not pair to form a monovalent molecule; the $V_H$ of each one of the scFv pairs with the $V_L$ domain of the other scFv to form a bivalent molecule); (ix) bi-specific antibodies (consisting of at least two antigen binding regions, each region binding a different epitope). In some embodiments, the fragment is a Fab fragment or is a single-chain antibody (scFv).

In some embodiments, hLAAIGEs according to the present invention are recombinant or modified antibodies, e.g., chimeric, deimmunized, and/or in vitro generated antibodies. The term "recombinant" or "modified" as applied to antibodies and as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g., a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In some embodiments, hLAAIGEs according to the present invention comprise scFv multimers. In some embodiments, hLAAIGEs according to the present invention comprise a constant region of an immunoglobulin (e.g., an Fc region). In some embodiments, hLAAIGEs according to the present invention comprise a free thiol (—SH) group at the carboxyl terminus, where the free thiol group can be used to attach the antibody to a second polypeptide (e.g., another antibody, including a subject antibody), a scaffold, a carrier, etc. In some embodiments, hLAAIGEs according to the present invention include one or more non-naturally occurring amino acids. In some embodiments, hLAAIGEs according to the present invention have a moiety of interest, e.g., a detectable label, drug, toxin, half-life-extending moiety, and the like, attached thereto. In some embodiments, hLAAIGEs according to the present invention are glycosylated, e.g., the hLAAIGEs include a covalently linked carbohydrate or polysaccharide moiety. In some embodiments, hLAAIGEs according to the present invention are covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. In some embodiments, hLAAIGEs according to the present invention are immobilized on a solid support. In some embodiments, hLAAIGEs according to the present invention include a detectable label. In some embodiments, hLAAIGEs according to the present invention include a contrast agent or a radioisotope. In some embodiments, hLAAIGEs according to the present invention include a "radiopaque" label, e.g., a label that can be easily visualized using, for example, x-rays. In some embodiments, hLAAIGEs according to the present invention are linked to (e.g., covalently or non-covalently linked to) a fusion partner, e.g., a ligand; an epitope tag; a peptide; a protein other than an antibody; and the like. In some embodiments, hLAAIGEs according to the present invention are covalently linked to a carbohydrate moiety. In some embodiments, hLAAIGEs of the present invention are covalently linked to a lipid moiety. In some embodiments, hLAAIGEs of the present invention are incorporated into a liposome. These and other embodiments, as contemplated for the antibodies described in WO 2015/013668, are contemplated herein for the hLAAIGEs according to the present invention.

Methods of Producing an Antibody hLAAIGEs according to the present invention may be produced by any method in the art, e.g., protein synthesis, recombinant techniques, etc.

Recombinant techniques can be used for production of hLAAIGEs according to the present invention. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

In some embodiments, hLAAIGEs according to the present invention are single chain polypeptides, and can be synthesized using chemical peptide synthesis methods in the art. For example, techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart, et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A, et al. 2005 *Protein Pept Lett.* 12:723-8.

Once synthesized (either chemically or recombinantly), hLAAIGEs according to the present invention can be purified using methods in the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). As used herein, a "synthesized" antibody refers to an antibody or a binding fragment thereof that has been made using either chemical synthetic methods or recombinant methods known in the art.

Nucleic Acid Molecules

In some embodiments, the present invention is directed to nucleic acid molecules that encode one or more amino acid sequences of hLAAIGEs. Such nucleic acid molecules may be operably linked to one or more regulatory elements, such as a promoter and enhancer, that allow expression of the nucleotide sequence in the intended target cells (e.g., a cell that is genetically modified to synthesize the encoded antibody). Suitable promoters and enhancers are known in the art.

Vectors

In some embodiments, the nucleic acid molecules are present in an expression vector and/or a cloning vector. Where hLAAIGEs of the present invention comprise two separate polypeptides, nucleotide sequences encoding the two polypeptides can be cloned in the same or separate vectors. Suitable vectors are known in the art, and can include a selectable marker, an origin of replication, and other features that provide for replication and/or maintenance of the vector.

Cells

In some embodiments, host cells according to the present invention contain one or more nucleic acid molecules according to the present invention. In some embodiments, the host cells are capable of producing hLAAIGEs according to the present invention. In some embodiments, the host cells are hybridomas.

Compositions

In some embodiments, compositions according to the present invention comprise one or more hLAAIGEs. In some embodiments, the compositions comprise an effective amount of the one or more hLAAIGEs. In some embodiments, the compositions are substantially pure, e.g., at least about 80% to 85% pure, at least about 85% to 90% pure, at least about 90% to 95% pure, or 98% to 99%, or more, pure, e.g., free from contaminants, such as cell debris, by-products resulting from the synthesis of the one or more hLAAIGEs, and biomolecules other than the hLAAIGEs. In some embodiments, the compositions according to the present invention comprise one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

In some embodiments, compositions according to the present invention are pharmaceutical compositions. In some embodiments, the pharmaceutical compositions comprise a therapeutically effective amount of one or more hLAAIGEs. As used herein, a "pharmaceutical composition" refers to a composition suitable for pharmaceutical use in a subject. A pharmaceutical composition generally comprises an effective amount of an active agent and a pharmaceutically acceptable carrier, e.g., a buffer, adjuvant, and the like. As used herein, a "pharmaceutically acceptable carrier" refers to solvents, dispersion media, coatings, antibacterial and antifungal agents, isotonic and absorption delaying agents, and the like, that are compatible with the active ingredient and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., REMINGTON: THE SCIENCE AND PRACTICE OF PHARMACY. 20th ed. (2000) Lippincott Williams & Wilkins. Baltimore, Md.

As used herein, an "effective amount" refers to a dosage or amount sufficient to produce a desired result. The desired result may comprise an objective or subjective response in, for example, a treatment group as compared to a control group in, for example, an in vitro assay. In some embodiments, the effective amount is a "therapeutically effective amount". As used herein, a "therapeutically effective amount" refers to an amount sufficient to provide a beneficial or desired therapeutic (including preventative) result in a subject, such as a reduction in a symptom of an IgE-mediated disorder, as compared to a control or a baseline measurement of the symptom before treatment. A therapeutically effective amount may be administered as a single dose or as a series of several doses. The skilled artisan will appreciate that certain factors may influence the dosage required to effectively treat a subject, including the degree of symptoms, previous treatments, the general health and age of the subject, and the like. Nevertheless, effective amounts and therapeutically effective amounts may be readily determined using methods known in the art.

In some embodiments, the therapeutically effective amount of one or more hLAAIGEs is about 0.1 mg/kg to about 10 mg/kg body weight of the subject. In some embodiments, the therapeutically effective amount of one or more hLAAIGEs is about 0.2 mg/kg to about 10 mg/kg body weight of the subject. In some embodiments, the therapeutically effective amount of one or more hLAAIGEs is about 0.3 mg/kg to about 10 mg/kg body weight of the subject. In some embodiments, the therapeutically effective amount of one or more hLAAIGEs is about 0.4 mg/kg to about 7 mg/kg body weight of the subject. In some embodiments, the therapeutically effective amount of one or more hLAAIGEs is about 0.5 mg/kg to about 5 mg/kg body weight of the subject. In some embodiments, therapeutically effective amount of the one or more hLAAIGEs is about 0.5 mg/kg to about 3 mg/kg body weight of the subject. In some embodiments, the therapeutically effective amount of one or more hLAAIGEs is administered to the subject.

In some embodiments, the therapeutically effective amount of the one or more hLAAIGEs is administered to a subject every 3 to 10 weeks. In some embodiments, the therapeutically effective amount of the one or more hLAAIGEs is administered to a subject every 3 to 8 weeks. In some embodiments, the therapeutically effective amount of the one or more hLAAIGEs is administered to a subject every 4 to 8 weeks. In some embodiments, the therapeutically effective amount of the one or more hLAAIGEs is administered to a subject every 4 to 6 weeks. In some embodiments, the therapeutically effective amount of the one or more hLAAIGEs is administered to a subject every 4 to 5 weeks. In some embodiments, the therapeutically effective amount of the one or more hLAAIGEs is administered to a subject monthly.

In some embodiments, the compositions comprise one or more hLAAIGEs at a concentration of about 1 mg/ml to about 200 mg/ml, about 50 mg/ml to about 200 mg/ml, or about 150 mg/ml to about 200 mg/ml. In some embodiments, the compositions comprise one or more hLAAIGEs at a concentration of about 10 mg/ml to about 1000 mg/ml, e.g., about 25 mg/ml to about 500 mg/ml, about 50 mg/ml to about 250 mg/ml, about 75 mg/ml to about 200 mg/ml, or about 100 mg/ml to about 150 mg/ml (e.g., about 125 mg/ml).

Pharmaceutical compositions of the present invention may be formulated for the intended route of delivery, including intravenous, intramuscular, intra peritoneal, subcutaneous, intraocular, intrathecal, intraarticular, intrasynovial, cisternal, intrahepatic, intralesional injection, intracranial injection, infusion, and/or inhaled routes of administration using methods known in the art. Pharmaceutical compositions according to the present invention may include one or more of the following: pH buffered solutions, adjuvants (e.g., preservatives, wetting agents, emulsifying agents, and dispersing agents), liposomal formulations, nanoparticles, dispersions, suspensions or emulsions as well as sterile powders for reconstitution into sterile injectable solutions or dispersions. The compositions and formulations of the present invention may be optimized for increased stability and efficacy using methods known in the art.

Dosages and Regimen

Pharmaceutical compositions of the present invention may be provided in dosage unit forms. As used herein, "dosage unit form" refers to physically discrete units suited as unitary dosages for the subject to be treated; each unit containing a predetermined quantity of an active ingredient calculated to produce the desired therapeutic effect in association with the required pharmaceutically acceptable carrier. The specification for the dosage unit forms of the invention are dictated by the unique characteristics of the active ingredient and the particular therapeutic effect to be achieved, and the limitations inherent in the art of compounding such an active ingredient for the treatment of individuals.

Toxicity and therapeutic efficacy of the compositions according to the present invention can be determined by standard pharmaceutical procedures in cell cultures or experimental animals. For example, one may determine the lethal dose, $LC_{50}$ (the dose expressed as concentration x exposure time that is lethal to 50% of the population) or the $LD_{50}$ (the dose lethal to 50% of the population), and the $ED_{50}$ (the dose therapeutically effective in 50% of the population) by methods known in the art. The dose ratio between toxic and therapeutic effects is the therapeutic index and it can be expressed as the ratio $LD_{50}/ED_{50}$. Compositions that exhibit large therapeutic indices are preferred. While compositions that exhibit toxic side effects may be used, care should be taken to use a delivery system that targets such compositions to the site of affected tissue in order to reduce side effects.

The data obtained from the cell culture assays and animal studies can be used in formulating a range of dosages for various combinations of one or more hLAAIGEs for use in humans. The dosages are preferably within a range of circulating concentrations that include the $ED_{50}$ with little or no toxicity. The dosage may vary within this range depending upon the dosage form employed and the route of administration utilized. A therapeutically effective dose can be estimated from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured using methods known in the art.

Additionally, a suitable dosage for a given subject can be determined by a physician or another qualified medical professional, based on various clinical factors. As is well known in the medical arts, dosages for any one subject depend upon many factors, including the subject's size, body surface area, age, the particular compound to be administered, sex of the subject, time, and route of administration, general health, and other drugs being administered concurrently. One or more hLAAIGEs may be administered in amounts between 1 ng/kg body weight and 20 mg/kg body weight per dose, e.g., between 0.1 mg/kg body weight to 10 mg/kg body weight, between 0.5 mg/kg body weight to 8 mg/kg body weight, between 1 mg/kg body weight to 6 mg/kg body weight, e.g., between 2 mg/kg body weight to 5 mg/kg body weight; however, doses below or above these ranges are envisioned, especially considering the aforementioned factors. If the regimen is a continuous infusion, it can also be in the range of 1 μg to 10 mg per kilogram of body weight per minute. One or more hLAAIGEs may be administered as a single dose or in multiple doses. For example, one or more hLAAIGEs may be administered 2 times per day, 1 time per day, once every 2 days, once every 3 days, once per week, once every two weeks, once per month, once every two months, etc.

Those of skilled in the art will readily appreciate that dose levels can vary as a function of the specific antibody, the severity of the symptoms and the susceptibility of the subject to side effects. Nevertheless, preferred dosages may be readily determined by those of skill in the art.

Methods of Treating IgE-Mediated Disorders

In some embodiments, the present invention provides methods of treating a disease or disorder mediated by IgE. The methods generally involving administering to a subject a therapeutically effective amount of one or more hLAAIGEs, alone (e.g., in monotherapy) or in combination (e.g., in combination therapy) with one or more additional therapeutic agents. In some embodiments, the one or more antibodies are administered in the form of a pharmaceutical composition. By "treating", "treat", or "treatment" is meant alleviating or abrogating an IgE-mediated disorder and/or at least one of its attendant symptoms. As used herein, to "alleviate" a disease, disorder, or condition means reducing the severity and/or occurrence frequency of the symptoms of the disease, disorder, or condition. It will be understood that references herein to "treating", "treat", or "treatment"

include references to curative, palliative, and prophylactic treatment. In some embodiments, a therapeutically effective amount of the one or more hLAAIGEs is an amount that, when administered alone (e.g., in monotherapy) or in combination (e.g., in combination therapy) with one or more additional therapeutic agents, is an amount that reduces the symptoms of an IgE-mediated disorder in a subject by at least about 5%, at least about 10%, at least about 15%, at least about 20%, at least about 25%, at least about 30%, at least about 40%, at least about 50%, at least about 60%, at least about 70%, at least about 80%, at least about 90%, or more, as compared to a control or a baseline measurement taken before treatment.

As used herein, an "IgE-mediated disorder" is a disorder, condition, or disease characterized by signal transduction through an IgE receptor, including the high-affinity IgE receptor (FcεRI) and/or the low-affinity IgE receptor (FcεRII; CD23). IgE-mediated disorders include those in which a type-I allergic reaction or type-I hypersensitivity is the primary event, such as in allergic asthma, allergic rhinitis, food allergies, allergic conjunctivitis, atopic dermatitis, anaphylaxis or anaphylactic hypersensitivity, eosinophilic esophagitis/gastroenteritis, mastocytosis, bee sting reactions, drug reactions, idiopathic urticaria, angioedema, etc. IgE-mediated disorders also include those disorders in which the type-I allergic reaction or type-I hypersensitivity plays an important secondary role in pathogenesis, e.g., allergic pulmonary aspergillosis, allergic purpura, hyper IgE Immune Deficiency Syndrome (HIES or Job's syndrome), rheumatoid arthritis, IgE myeloma, inflammatory bowel disease (for example, Crohn's disease, ulcerative colitis, indeterminate colitis, and infectious colitis), psoriasis, bullous pemphigoid, etc.

In some embodiments, the methods the present invention are methods for treating a subject having asthma, which comprises administering to the subject a therapeutically effective amount of one or more hLAAIGEs. Asthma is a chronic inflammatory disorder of the airways causing recurrent episodes of wheezing, breathlessness, chest tightness, and/or coughing in susceptible individuals. Those skilled in the art distinguish various types of asthma, including: allergic asthma, which is thought to arise in subjects having developed a hypersensitivity to environmental allergens; drug-induced asthma, typically triggered by sensitivity to aspirin or other COX inhibitors; exercise-induced asthma; near-fatal and hyperacute asthma; nocturnal asthma; occupational asthma, generally caused by exposure to certain chemicals in the workplace. Thus, asthma can be triggered by various stimuli, including airborne allergens (such as dust-mites, pollens, animal dander, fungal spores, feathers), non-specific irritants, such as tobacco smoke, chemical fumes, pollution, sulphur dioxide, and the like.

In some embodiments, the methods of the present invention are methods for treating a subject having allergic rhinitis, which comprises administering to the subject a therapeutically effective amount of one or more hLAAIGEs. Allergic rhinitis typically involves a collection of symptoms, including inflammatory symptoms, predominantly in the nose, sinuses, and eyes, which occur after exposure to airborne particles. Symptoms include sneezing; nasal obstruction; runny nose (and occasionally nosebleeds); coughing; headache; itching nose, mouth, eyes, throat, skin, or any area exposed to the allergen; impaired smell (and thus sensitivity to flavors); stuffy nose (nasal congestion); conjunctivitis; watering eyes; sore throat; and wheezing. Allergic rhinitis may be perennial and/or seasonal. Perennial allergic rhinitis is allergic rhinitis that lasts throughout the year. It is typically caused by continuous exposure to allergens such as animal dander, indoor mould spores, or house dust mites. Seasonal allergic rhinitis is allergic rhinitis that occurs only during certain times of the year. It is commonly caused by allergies to tree, grass, and weed pollen that are produced seasonally.

In some embodiments, the methods of the present invention are methods for treating a subject with one or more IgE-mediated food allergies, which comprises administering to the subject a therapeutically effective amount of one or more hLAAIGEs. An IgE-mediated food allergy is an exaggerated immune response triggered by eggs, peanuts, milk, or some other specific food. Any food can cause an allergic reaction, but a few foods are the main culprits. In children, the most common food allergies are to eggs, peanuts, milk, soy, tree nuts, wheat, and shellfish (e.g., shrimp, crab, lobster, snails, and clams). In older children and adults, the most common food allergies are: peanuts, tree nuts, shellfish, and fish. The symptoms may be confined mainly to the stomach and intestines, or may involve many parts of the body after the food is digested or absorbed. Symptoms may include: scratchy throat, anaphylaxis (a severe, whole-body allergic reaction that can result in death); abdominal pain; diarrhea; nausea; vomiting; stomach cramps; itching of the mouth, throat, eyes, skin, or any area; hives; angioedema (swelling, especially of the eyelids, face, lips, and tongue); light-headedness or fainting; nasal congestion; runny nose; shortness of breath; wheezing; difficulty swallowing; oral allergy syndrome. The oral allergy syndrome typically comprises itching lips, tongue, and throat, and sometimes swollen lips.

In some embodiments, the treatment methods further include administering to the subject one or more additional therapeutic agents. Suitable additional therapeutic agents include a second anti-IgE antibody such as omalizumab, lumiliximab, and/or the antibody CIA-E-7.12 (ATCC Accession No. HB-236)), immunosuppressive agents, anti-inflammatory agents, and the like. In some embodiments, the additional therapeutic agent may be co-administered or co-formulated with the one or more hLAAIGEs. In some embodiments, the one or more hLAAIGEs are co-administered or co-formulated with one or more ingredients selected from the group consisting of steroids, including corticosteroids (inhaled, oral); bronchodilators (such as long-acting beta-2 agonists; short-acting beta-2 agonists); leukotriene antagonists/inhibitors; methylxanthines; antibodies directed against interleukins involved in airway inflammation, e.g., hLAAIGEs directed against IL-4 or IL-13 or TNF; cromolyns, such as cromolyn sodium; nedocromil sodium; and anticholerginics and PDE inhibitors. Combination treatments according to the present invention include simultaneous (concurrent) and consecutive administration in any order.

In some embodiments, a subject to be treated with one or more hLAAIGEs is a subject is in need thereof. Generally, a subject "in need of" treatment with hLAAIGE is a subject who has an IgE-mediated disorder. Subjects in need of treatment also include those likely to have or are susceptible to having an IgE-mediated disorder, and those in which the IgE-mediated disorder is to be prevented. A subject susceptible to having an IgE-mediated disorder may be identified by determining total and/or allergen-specific IgE, allergen skin test, clinical and/or family history, etc.

Figure 27:
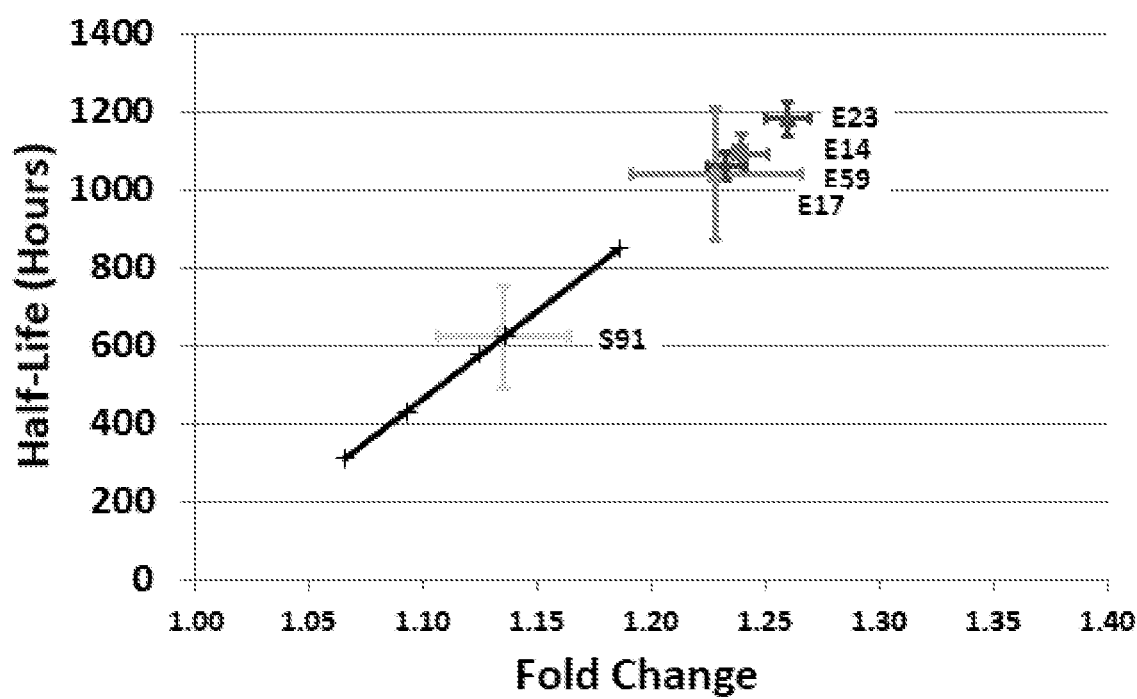
FIG. 27 is a graph showing the predicted in vivo half-lives of 5 hLAAIGEs according to the present invention as assessed by a validated in vitro model. See Soudersy et al. (2015) mAbs 7(5): 912-921).

The in vivo half-lives of E14, E17, E23, E59, and S91 were determined using an FcRn-based binding assay. E14, E17, E23, and E59 exhibit remarkably long half-lives of greater than about 40 days (greater than about 960 hours)

while the half-life of S91 was about 25 days (FIG. 27). Therefore, in some embodiments, subjects are dosed with a therapeutically effective amount of one or more hLAAIGEs according to the present invention at intervals of about 3 weeks to about 6 weeks. In some embodiments, subjects are dosed with a therapeutically effective amount of one or more hLAAIGEs according to the present invention at intervals of about 4 weeks to about 5 weeks. In some embodiments, subjects are dosed with a therapeutically effective amount of one or more hLAAIGEs according to the present invention at intervals of about one month.

The potential immunogenicity (B and T cell epitopes) of the hLAAIGEs disclosed herein was negative as determined in silico using the IEBD tool developed by the La Jolla Institute of Allergy and Immunology (tools.immuneepitope-.org).

Kits

In some embodiments, the invention is a kit (e.g., therapeutic kits) that includes one or more hLAAIGEs. Such kits are useful, e.g., in carrying out the methods according to the present invention.

In some embodiments, the kit may include one or more of: one or more hLAAIGEs, a nucleic acid molecule encoding the one or more antibodies, or a cell comprising the nucleic acid. In some embodiments, the one or more antibodies are provided as a pharmaceutical composition, e.g., in a single dose, two or more dosage unites, etc.

Kits according to the present invention may include instructions for using the components of the kit, e.g., to practice the treatment method according to the present invention. The instructions may be present in the kits as a package insert, in the labeling of the container of the kit or components thereof (e.g., associated with the packaging or subpackaging) etc. In some embodiments, the instructions are present as an electronic storage data file present on a suitable computer readable storage medium, e.g., compact disc-read only memory (CD-ROM), digital versatile disk (DVD), flash drive, etc. In some embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are intended to illustrate but not to limit the invention.

EXAMPLES

The following examples are put forth to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); ~, about, and the like, and amino acid one letter and three letter codes.

Commercially available reagents referred to in the Examples were used according to manufacturer's instructions unless otherwise indicated. Example methods and materials are described below although methods and materials similar or equivalent to those described herein can also be used in the practice or testing of the present invention. The materials, methods, and examples are illustrative only and not intended to be limiting in scope.

Example 1

Generation of Humanized Anti-Human IgE Antibodies

Hybridoma cell lines producing low affinity anti-human IgE (LAAIGE) founder mouse mAbs, i.e., Founder E17, Founder F11, and Founder P6.2 were made according to the methods disclosed in WO 2015/013668.

The cDNA and predicted protein sequences of Founder E17 are:

Founder E17 VH cDNA:
(SEQ ID NO: 46)
CAGTCTGGACCTGAGCTGAAGAAGCCTGGAGAGACAGTCAAGATCTC

CTGCAAGGCTTCCGGCTACACCTTCACAAACTATGGCATGAACTGGG

TGAAGCAGGCTCCAGGAAAGGGTTTAAAGTGGATGGGCTGGATCAAC

ACCTACACAGGCGAGCCCACATATGCTGATGACTTCAAGGGACGGTT

TGCCTTCTCTTTGGAAACCTCTGCCAGCACTGCCTATTTGCAGATCA

ACAACCTGAAAAATGAGGACACCGCTACATACTTCTGTGCTAGAGGA

GCTGCTTCCCACACAATGGATTATTGGGGCCAAGGCACCAC

Founder E17 VH protein:
(SEQ ID NO: 47)
QSGPELKKPGETVKISCKASGYTFTNYGMNWVKQAPGKGLKWMGWIN

TYTGEPTYADDFKGRFAFSLETSASTAYLQINNLKNEDTATYFCARG

AASHTMDYWGQGT

Founder E17 VL cDNA:
(SEQ ID NO: 48)
GACATTGTGCTAACACAGTCTCCTGCTTCCTTAGCTGTATCTCTGGG

GCAGAGAGCTACCATCTCATGCAGGGCTAGCCAGTCCGTGTCTACAA

GCTCCCACGCCTACATGCACTGGTATCAGCAGAAACCCGGACAGCCA

CCCAAGCTCCTGATCAAGTATGCTAGCAATCTGGAGTCTGGGGTGCC

TGCCAGGTTCAGCGGAAGTGGCTCTGGGACAGACTTCACCCTCAACA

TCGATCCTGTGGAGGAGGAGGACACTGCCACATACTATTGCCAGCAC

AGTTGGGAGATTCCTTGGACCTTCGGCCAGGGCACCAAGCTGGAAAT

CAA

Founder E17 VL protein:
(SEQ ID NO: 49)
DIVLTQSPASLAVSLGQRATISCRASQSVSTSSHAYMHWYQQKPGQP

PKLLIKYASNLESGVPARFSGSGSGTDFTLNIDPVEEEDTATYYCQH

SWEIPWTFGQGTKLEI

The cDNA and predicted protein sequences of Founder F11 are:

Founder F11 VH cDNA:
(SEQ ID NO: 50)
CAGGTTCAGCTGCAGCAGTCTGGAGCTGAGCTGGCGAGGCCTGGGGC

TTCAGTGAAGCTGTCCTGCAAGGCTTCTGGTTACACCTTTACCAGCT

ATGGTATAAGCTGGGTGAAGCAGAGAACTGGACAGGGCCTTGAGTGG

ATTGGAGAGATCAGCGCTTACAATGGTAACACATACTACAATGAGAA

GTTCAAGGGCAAGGCCACACTGACTGCAGACAAATCCTCCAGCACAG

CGTACATGGAGCTCCGCAGCCTGACATCTGAGGACTCTGCGGTCTAT

TTCTGTGCGAGAGTTAGCAGCTGGCCATACTGGTACTTCGATCTCTG

GGGC

Founder F11 VH protein:
(SEQ ID NO: 51)
QVQLQQSGAELARPGASVKLSCKASGYTFTSYGISWVKQRTGQGLEW

IGEISAYNGNTYYNEKFKGKATLTADKSSSTAYMELRSLTSEDSAVY

FCARVSSWPYWYFDLWG

Founder F11 VL cDNA:
(SEQ ID NO: 52)
ACGCAGCCGCCCTCCGCGTCCGGGTCTCCTGGACAGTCAGTCACCAT

CTCCTGCACTGGAACCAGCAGTGACGTTGGTGCGTATGACTATGTCT

CCTGGTACCAACAGCACCCAGGCAAAGCCCCCAAACTCATGATTTAT

GAGGTCAGTAAGCGGCCCTCAGGGGTCCCTGATCGCTTCTCTGGCTC

CATTGACAAGTCTGGCAACACGGCCTCCCTGACCGTCTCTGGGCTCC

AGGCTGAGGATAGCTCATATGCCGGCAGAGTTGATGTGTTCGGCGGA

GGGACCAAGCTGACCGTCCTA

Founder F11 VL protein:
(SEQ ID NO: 53)
TQPPSASGSPGQSVTISCTGTSSDVGAYDYVSWYQQHPGKAPKLMIY

EVSKRPSGVPDRFSGSIDKSGNTASLTVSGLQAEDSSYAGRVDVFGG

GTKLTVL

The cDNA and predicted protein sequences of Founder P6.2 are:

Founder P6.2 VH cDNA:
(SEQ ID NO: 54)
CAGGTCCAGCTGCAGCAGTCTGGAGCTGAGCTGGTAAGGCCTGGGAC

TTCAGTGAAGGTGTCCTGCAAGGCTTCTGGATACGCCTTCACTAATT

ACTTGATAGAGTGGGTAAAGCAGAGGCCTGGACAGGGCCTTGAGTGG

ATTGGAGTGATTAATCCTGGAAGTGGTTTTACAAAATACAATGAGAA

GTTCAAGGGCAAGGCAACACTGACTGCAGACAAATCCTCCAGCACTG

CCTACATGCACCTCAGCAGCCTGACATCTGATGACTCTGCGGTCTAT

TTCTGTGCAAGAGAAGATGTTTACTCCTGGTTTGCTTACTGGGGCCA

AGGGACTCTGGTCACTGTCTCTGCA

Founder P6.2 VH protein:
(SEQ ID NO: 55)
QVQLQQSGAELVRPGTSVKVSCKASGYAFTNYLIEWVKQRPGQGLEW

IGVINPGSGFTKYNEKFKGKATLTADKSSSTAYMHLSSLTSDDSAVY

FCAREDVYSWFAYWGQGTLVTVSA

Founder P6.2 VL cDNA:
(SEQ ID NO: 56)
GACATTGTGCTGACCCAATCTCCAGCTTCTTTGGCTGTGTCTCTAGG

GCAGAGGGCCACCATATCCTGCAGAGCCAGTGAAAGTGTTGATAGTT

ATGGCAATAGTTTTATGCACTGGTACCAGCAGAAACCAGGACAGCCA

CCCAAACTCCTCATCTATCGTACATCCAACCTAGAATCTGGGATCCC

TGCCAGGTTCAGTGGCAGTGGGTCTAGGACAGACTTCACCCTCACCA

TTAATCCTGTGGAGGCTGATGATGTTGCAACCTATTTCTGTCAGCAA

AGTTATGAGGATCCATTCACGTTCGGCTCGGGGACAAAGTTGGAAAT

AAAA

Founder P6.2 VL protein:
(SEQ ID NO: 57)
DIVLTQSPASLAVSLGQRATISCRASESVDSYGNSFMHWYQQKPGQP

PKLLIYRTSNLESGIPARFSGSGSRTDFTLTINPVEADDVATYFCQQ

SYEDPFTFGSGTKLEIK

Founder F11, Founder E17, and Founder P6.2 have binding affinities for human IgE of about $6.92 \times 10^{-7}$, $8.19 \times 10^{-8}$, and about $2.54 \times 10^{-6}$ M respectively. The complementary determining region (CDR) sequences and the specificity-determining residues (SDR) of each heavy chain variable (VH) and light chain variable (VL) regions were engrafted into the framework (FR) regions of the most homologous human germline sequences. All the recombinant mAbs were transiently expressed in 293 cells in small scale (50 ml transfection volume) and purified by protein A affinity column for downstream application. The humanized mAbs not expressing or expressing <1 µg/ml recombinant antibody were eliminated. The affinity of humanized LAAIGE (hLAAIGE) to α-IgE was determined by the surface plasmon resonance using Biacore T2000 instrument (Biacore AB, Uppsala, Sweden) with a CM5 sensor chip coupled with myeloma IgE by amine coupling. The purified hLAAIGEs were dissolved in HBS-EP assay buffer containing 0.15 M NaCl, 10 mM HEPES, pH 7.4, 3 mM EDTA, and 0.005% polysorbate 20. The solutions traversed the sensors at a flow rate of 50 µl/minute for binding analysis. Binding results were expressed in resonance units. Kinetic studies were analyzed with BIAevaluation Software Version 4.1. The clones with affinity to IgE lower than sensitivity limit of the Biacore T2000 (<$5 \times 10^{-5}$ M) were not further analyzed, and the antibodies with IgE affinity ranging from about $7 \times 10^{-5}$ M to about $7 \times 10^{-8}$ M were chosen for further evaluation of their therapeutic potency and safety profiles. The binding of the selected hLAAIGE to the cell surface-bound IgE was confirmed using the human FcεRIα expressing 3D10 cells sensitized with myeloma IgE.

The protein sequences of the hLAAIGEs are as follows:

E59 VH:
(SEQ ID NO: 1)
QVQLVQSGSELKKPGASVKVSCKASGYTFTNYGMNWVRQAPGQGLEWMGWINTYTGEPTY
ADDFKGRFVFSLDTSVSTAYLQISSLKAEDTAVYYCARGAASHTMDYWGQGTTVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

E59 VL:
(SEQ ID NO: 3)
DIVMTQSPDSLAVSLGERATINCRASQSVSTSSHSYMHWYQQKPGQPPKLLIYYASNLES
GVPDRFSGSGSGTDFTLTISSLQAEDVAVYYCQHSWEIPWTFGQGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

E14 VH:
(SEQ ID NO: 58)
QVQLVQSGSELKKPGASVKVSCKASGYTFTNYGMNWVRQAPGQGLEWMGWINTYTGEPTY
ADDFKGRFVFSLDTSVSTAYLQISSLKAEDTAVYYCARGAASHTMDYWGQGTTVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

E14 VL:
(SEQ ID NO: 59)
DIVMTQSPDSLAVSLGERATINCRASQSVSTSAHSYMHWYQQKPGQPPKLLIYYASNLES
GVPDRFSGSGSGTDFTLTISSLQAEDVAVYYCQHSWEIPWTFGQGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

E17 VH:
(SEQ ID NO: 60)
QVQLVQSGSELKKPGASVKVSCKASGYTFTNYGMNWVRQAPGQGLEWMGWINTYTGEPTY
ADDFKGRFVFSLDTSVSTAYLQISSLKAEDTAVYYCARGAASHTMDYWGQGTTVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

E17 VL:
(SEQ ID NO: 61)
DIVMTQSPDSLAVSLGERATINCRASQSVSTSSHAYMHWYQQKPGQPPKLLIYYASNLES
GVPDRFSGSGSGTDFTLTISSLQAEDVAVYYCQHSWEIPWTFGQGTKLEIKRTVAAPSVF

IFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC

E23 VH:
(SEQ ID NO: 62)
QVQLVQSGSELKKPGASVKVSCKASGYTFTNYGMNWVRQAPGQGLEWMGWINTYTGEPTY

ADDFKGRFVFSLDTSVSTAYLQISSLKAEDTAVYYCARGAASHTMDYWGQGTTVTVSSAS

TKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQ

GNVFSCSVMHEALHNHYTQKSLSLSPGK

E23 VL:
(SEQ ID NO: 63)
DIVMTQSPDSLAVSLGERATINCRASQSVSTSSYSYMHWYQQKPGQPPKLLIYYASNLKA

GVPDRFSGSGSGTDFTLTISSLQAEDVAVYYCQHSWEIPWTFGQGTKLEIKRTVAAPSVF

IFPPSDEQLKSGTASVVCLLNNFYPREAKVQWKVDNALQSGNSQESVTEQDKSDSTYSLS

STLTLSKADYEKHKVYACEVTHQGLSSPVTKSFNRGEC

S91 VH:
(SEQ ID NO: 64)
QVQLVQSGAEVKKPGASVKVSCKASGYTFTSYGISWVRQAPGQGLEWMGWISAYNGNTNY

AQKLQGRVTMTTDTSTSTAYMELRSLRSDDTAVYYCARVSSWPYWYFDLWGRGTLVTVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPG

S91 VL:
(SEQ ID NO: 65)
QSAVTQPPSASGSPGQSVTISCTGTSSDVGAYDYVSWYQQHPGKAPKLMIYEVSKRPSGV

PDRFSGSKSGNTASLTVSGLQAEDEADYYCSSYAGRVDVFGGGTKLTVLGQPKAAPSVTL

FPPSSEELQANKATLVCLISDFYPGAVTVAWKADSSPVKAGVETTTPSKQSNNKYAASSY

LSLTPEQWKSHRSYSCQVTHEGSTVEKTVAPTECS

H6.2 VH:
(SEQ ID NO: 66)
QVQLGQSGGGVVQPGRSLRLSCAASGFTFSNYLIEWVRQAPGKGLEWVAVINPGSGFTKY

NEKFKQRFTISRDNSKNTLYLQMNSLRAEDTAVYYCAREDVYSWFAYWGQGTLVTVSAVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

-continued

H6.2 VL:
(SEQ ID NO: 67)
QSALTQPASVSGSPGQGITISCTRASESVDSYGNSFMHQHHPGKAPKLMIYEVRTSNLES

SNRFSGSKSGNTASLTISGLQAEDEADYYCSSQQSYEDPFTFGSGTKLGQPKAAPSVTLF

PPSSEELQANKATLVCLISDFYPGAVKVAWKADGSPVNTGVETTTPSKQSNNKYAASSYL

SLTPEQWKSHRSYSCQVTHEGSTVEKTVAPAECS

The binding affinities of the hLAAIGEs to human IgE as measured by the Biacore method are: E23=1.09×10⁻⁷ M, E14=6.72×10⁻⁸ M, E59=1.64×10⁻⁷ M, E17=1.4×10⁻⁷ M, S91=7.41×10⁻⁶ M, and H6.2~5×10⁻⁵ M Kd.

Therefore, in some embodiments, the hLAAIGEs according to the present invention have a VH chain that comprises (SEQ ID NO: 68)
QVQLVQSGSELKKPGASVKVSCKASGYTFTNYGMNWVRQAPGQGLEW

MGWINTYTGEPTYADDFKGRFVFSLDTSVSTAYLQISSLKAEDTAVY

YCARGAASHTMDYWGQGTTVTVSSAS, (SEQ ID NO: 69)
QVQLVQSGAEVKKPGASVKVSCKASGYTFTSYGISWVRQAPGQGLEW

MGWISAYNGNTNYAQKLQGRVTMTTDTSTSTAYMELRSLRSDDTAVY

YCARVSSWPYWYFDLWGRGTLVTVSSAS,
or (SEQ ID NO: 70)
QVQLGQSGGGVVQPGRSLRLSCAASGFTFSNYLIEWVRQAPGKGLEW

VAVINPGSGFTKYNEKFKQRFTISRDNSKNTLYLQMNSLRAEDTAVY

YCAREDVYSWFAYWGQGTLVTVSAVTVSSAS.

Example 2

Activity and Efficacy Assays

The activity and therapeutic efficacy of given hLAAIGEs were determined by: 1) Inhibition of peanut and cat allergic subjects' blood basophil activation test (BAT); 2) Inhibition of the peanut allergic IgE mediated passive cutaneous anaphylaxis (PCA) in the hFcεRIα transgenic mouse model; and 3) Inhibition of dansyl-IgE mediated systemic anaphylaxis in the hFcεRIα transgenic mouse model.

1) Basophil Activation Test Assay

A Basophil Activation Test (BAT) assay was performed to determine the ability of each humanized mAb to induce basophil activation at various concentrations. To test whether a given hLAAIGE activates basophils, blood (100 µl) from cat or peanut allergic subjects were incubated with varying amounts ranging from 1-50 µg/ml of the given hLAAIGE for 20 minutes at 37° C. The activation reaction was stopped by EDTA and the cells were then stained for 20 minutes on ice with a cocktail of CD123-FITC/CD63-PE/HLA-Dr-PerCP. Followed by lysis of red blood cells, the stained cells were analyzed with flow cytometry. The basophil population was gated in the CD123 positive/HLA-Dr negative population. CD63 expression in the basophil population was calculated and analyzed.

For determination of whether a given humanized mAb would block allergen triggered basophil activation, the blood samples were incubated with humanized mAb for 24 hours and/or 48 hours at 37° C. with constant shaking, then cat allergen Fel d1 (0.02-0.2 µg/ml) or peanut allergen (Ara h1, 2 and 6 combined, 0.1-1.0 µg/ml) were added into the blood for a 15-minute incubation at 37° C. to activate the basophils.

2) Passive Cutaneous Anaphylaxis (PCA) Assay

Passive Cutaneous Anaphylaxis (PCA) assays were performed to investigate the ability of each humanized mAb to block peanut and cat allergic IgE-mediated PCA. The back skin of hFcεRIα Tg mice were intradermally injected with IgE (8-10 spots per mouse skin), purified from peanut allergic subject's plasma for local sensitization for overnight to four days. To test whether a given hLAAIGE would activate mast cells, the sensitized spots were got a local injection of various amounts of the given hLAAIGE (1-100 µg/ml range), with PBS negative control; and polyclonal rabbit anti-human IgE (0.1-1 µg/ml) as the positive control. Fifteen minutes later, 100 µl of 2% Evan's blue dye was intravenously injected to assess the local allergic reactivity.

To test whether a given hLAAIGE would block allergen-mediated PCA, hFcεRIα Tg mice were sensitized with the purified peanut allergic IgE and the recombinant dansyl specific IgE at 2, 1, 0.5, and 0.125 µg/ml through intradermal injection on the back skin for 2 hours, followed by injecting the mouse i.p. with the given hLAAIGE at 2 µg/gram body weight, with the same amount of human IgG₁ as an isotype control. Four or five days later, the animals were challenged i.v. with Ara h1, 2, and 6 combined or crude peanut extract (CPE, 10 µg), or Dansyl-BSA (100 µg) mixed with 100 µl 2% Evans blue dye (EBD) dissolved in saline. The mice were euthanized 30 minutes post allergen challenge for assessing PCA reaction by photography. The mouse skin was dried overnight, and the injected skin areas were cut out, weighted, and EBD was extracted with formamide at 55° C. overnight. The extravasated EBD was either quantified with a spectrophotometer at wavelength of 620 nm or 650 nm with a microtiter ELISA reader. The quantitative results from both methods fit well. EBD quantity from each PCA spot was normalized as per milligram skin tissue.

3) Systemic Anaphylaxis Assay

The FcεRIα Tg mice were sensitized with a total of 40 µg (20 µg twice at 16-hour interval) of recombinant dansyl-specific IgE overnight (about 24 hours), followed by injection with a given hLAAIGE or human IgG₁ isotype as a control at 2 µg/gram body weight. Four days later, the mice were intravenously challenged with Dansyl-BSA (100 µg/mouse) to induce systemic anaphylaxis. Core body temperature changes and the anaphylaxis clinical index (scores) were measured as indicators of systemic allergic reactivity. The core body temperature changes were monitored every five minutes for the first hour after Dansyl-BSA challenge. The temperature changes were plotted for comparison and statistical analysis to determine the effect of the given hLAAIGE and control IgG₁ on systemic anaphylaxis.

Example 3

Bone Marrow Derived Mast Cells (BMMC) from hFcεRIα Tg Mouse

The bone marrow was flushed out from the femurs and tibias of the hFcεRIα Tg mouse with 0.22 μm filtered flushing medium (DMEM supplemented with 10% fetal bovine serum, 2 mM L-glutamine, 50 U/ml penicillin and 50 μg/ml streptomycin, $5\times10^{-5}$ M β-mercaptoethanol). The collected bone marrow cells were cultured in two T75 flasks with 10 ml culture medium (flushing medium plus 10 ng/ml recombinant mouse IL-3) each. Three days later, the suspended cells from each flask were transferred and expanded into two flasks with fresh culture medium. One week later, the suspended cells from each flask were expanded into 2 to 3 flasks, maintaining the cell density in about $1\times10^{6}$ cells/ml. Half of the culture medium was replaced with fresh medium every 3 to 4 days, and the suspended cells were transferred to new flasks until no adhere cells were observed. Six weeks later, the suspended cells were stained with anti-mouse CD117-FITC and anti-human hFcεRIα-PE to assess the maturity of the cultured BMMC.

Example 4

Confocal Microscopy

BMMCs were centrifuged at 1500 RPM for 3 minutes, and the supernatant was carefully aspirated, and the cell pellets were washed with PBSX2, followed by blocking with 10% of normal mouse serum and incubated for 30 minutes on ice, then added diluted FITC-labeled myeloma IgE (PS IgE) at 5 μg/ml for sensitization for 2 hours. After washing, the FITC-IgE sensitized BMMCs ($1\times10^{6}$ cell/ml) were incubated with the control mIgG$_1$ and hLAAIGE at 2 μg/ml respectively for 24 or 48 hours at 37° C. The BMMCs were fixed with 0.5 ml of 2% formaldehyde for 30 minutes. After completing the above staining procedure, the tube(s) were kept at room temperature (dark) for 20 minutes. The cells were washed with PBS for 2 times following by adding 50 μl of permeabilization medium, along with the Alexa 647-labelled anti-hFcεRIα for incubation at room temperature for 30 minutes. The washed cells were then fixed with 0.5 ml of 2% formaldehyde, and span to the poly-lysine coated glass slide using cytospin at 500 rpm for 5 minutes. The cells on the slides were stained with a drop of prolong gold anti-Fade reagent with DAPI. The slides were examined with Leica SP2-1P-FCS confocal microscope.

Additional Embodiments

Embodiment 1. An antibody comprising a VH sequence having a percent identity of at least about 90% up to 100%, preferably about 91% up to 100%, more preferably about 95% up to 100%, even more preferably about 97% up to 100%, and most preferably about 99% up to 100% to SEQ ID NO:1.

Embodiment 2. The antibody according to Embodiment 1, wherein a portion of the VH sequence has a percent identity of about 75% to about 100%, preferably about 80% to about 100%, more preferably about 90% to 100%, even more preferably about 95% to about 100%, and most preferably about 99% to 100% to SEQ ID NO:2.

Embodiment 3. The antibody according to Embodiment 1 or Embodiment 2, and further comprising a portion of a VL sequence having a percent identity of at least about 65% up to 100% to SEQ ID NO:4.

Embodiment 4. The antibody according to Embodiment 1 or Embodiment 2, wherein the sequence identity of the portion of the VL sequence is about 65% to about 70% of SEQ ID NO:4.

Embodiment 5. The antibody according to Embodiment 4, wherein the sequence of the portion of the VL sequence is selected from the group consisting of: SEQ ID NO:4, SEQ ID NO:5, and SEQ ID NO:6.

Embodiment 6. The antibody according to any one of Embodiments 1 to 5, wherein the antibody is a monoclonal antibody.

Embodiment 7. The antibody according to Embodiment 6, wherein the antibody is a humanized antibody.

Embodiment 8. The antibody according to Embodiment 7, wherein the antibody binds to human IgE with a binding affinity of about $1\times10^{-5}$ M to about $1\times10^{-9}$ M Kd, about $1\times10^{-6}$ M to about $1\times10^{-9}$ M Kd, or about $5\times10^{-5}$ M to about $7\times10^{-8}$ M.

Embodiment 9. The antibody of according to Embodiment 1, wherein the antibody is E59, E14, E17, E23, or S91.

Embodiment 10. A composition comprising one or more antibodies according to any one of Embodiments 1 to 9.

Embodiment 11. A pharmaceutical composition comprising one or more antibodies according to any one of Embodiments 1 to 9, and a pharmaceutically acceptable carrier.

Embodiment 12. A method of treating a subject for an IgE-mediated disorder, which comprises administering to the subject one or more antibodies according to any one of Embodiments 1 to 9, a composition according to Embodiment 10, or a pharmaceutical composition according to Embodiment 11.

Embodiment 13. The method according to Embodiment 12, wherein the IgE-mediated disorder is asthma, allergic rhinitis, atopic dermatitis, urticaria, angioedema, or anaphylactic hypersensitivity.

Embodiment 14. A method for treating or inhibiting an allergic reaction in a subject, which comprises administering to the subject one or more antibodies according to any one of Embodiments 1 to 9, a composition according to Embodiment 10, or a pharmaceutical composition according to Embodiment 11.

Embodiment 15. The method according to any one of Embodiments 12 to 14, wherein the one or more antibodies are administered to the subject in a therapeutically effective amount.

Embodiment 16. A monoclonal antibody which comprises a VH chain that comprises a VH chain that comprises DTAVYYCAR (SEQ ID NO:7), and a VL chain that comprises LQAED (SEQ ID NO:11) and at least one sequence selected from AAPSV (SEQ ID NO:12), GTKL (SEQ ID NO:13), and RFSGS (SEQ ID NO:14), preferably the VL sequence comprises LQAED (SEQ ID NO:11) plus (a) AAPSV (SEQ ID NO:12) or (b) RFSGS (SEQ ID NO:14) and GTKL (SEQ ID NO:13).

Embodiment 17. The monoclonal antibody according to Embodiment 16, wherein the VH chain is (X)$_{0-1}$VQLXQSG (X)$_5$PGXS(X)$_3$SCXASGXTF(X)$_6$WVRQAPGXGLEW (X)$_3$I(X)$_4$G(X)$_3$Y(X)$_6$R(X)$_5$DXS(X)$_2$T(X)$_6$SL(X)$_3$ DTAVYYCAR(X)$_{9-11}$WGXGTXVTVSSAS (SEQ ID NO:15) and/or the VL chain is (X)$_4$TQ(X)$_{0-1}$PXS(X)$_3$SXG (X)$_3$TIXC(X)$_{2-3}$S(X)V(X)$_{9-11}$Q(X)$_2$PG(X)$_2$PKLXIY(X)$_{2-4}$ S(X)$_3$S(X)$_{2-4}$RFSGSXSG(X)$_4$LTXSXLQAEDXAXYYC (X)$_{0-2}$Q(X)$_{6-8}$FGXGTKL(X)$_{3-7}$AAPSV(X)$_2$FPPSXE XL(X)$_4$A(X)$_2$VCL(X)$_3$FYP(X)$_4$VXWKXD(X)$_{5-6}$G(X)$_{1-3}$E (X)$_2$T(X)$_8$Y(X)$_2$SSXLXL(X)$_7$H(X)$_2$YXC XVTHXG(X)$_{0-2}$ SXVXK(X)$_5$EC(X)$_{0-1}$ (SEQ ID NO:16), wherein each X is independently any amino acid.

Embodiment 18. The monoclonal antibody according to Embodiment 16, wherein the VL chain comprises any one or more of the following sequences RFSGSX22SG (SEQ ID NO:24), LTX23SX24LQAEDX254AX26YY (SEQ ID NO:25), FGX27GTKL (SEQ ID NO:26), AAPSVX28X29FPPSX30EX31L (SEQ ID NO:27), AX32X33VCLX34X35X36FYP (SEQ ID NO:28), HX37X38YX39CX40VTHX41G (SEQ ID NO:29), PX42SX43X44X45SX45GX47X48X49TIX50C (SEQ ID NO:30), QX51X52PGX53X54PKLX55IY (SEQ ID NO:31), wherein X22 to X55 are each independently any amino acid.

Embodiment 19. The monoclonal antibody according to Embodiment 16, wherein the VL chain comprises any one or more of the following sequences RFSGSX22SG (SEQ ID NO:24), LTX23SX24LQAEDX254AX26YY (SEQ ID NO:25), FGX27GTKL (SEQ ID NO:26), AAPSVX28X29FPPSX30EX31L (SEQ ID NO:27), AX32X33VCLX34X35X36FYP (SEQ ID NO:28), HX37X38YX39CX40VTHX41G (SEQ ID NO:29), PX42SX43X44X45SX45GX47X48X49TIX50C (SEQ ID NO:30), QX51X52PGX53X54PKLX55 Y (SEQ ID NO:31), wherein X22 is G or K, X23 is I or V, X24 is G or S, X25 is E or V, X26 is D or V, X27 is G, S, or Q, X28 is F or T, X29 is I or L, X30 is D or S, X31 is E or Q, X32 is S or T, X33 is L or V, X34 is I or L, X35 is N or S, X36 is D or N, X37 is K or R, X38 is S or V, X39 is A or S, X40 is E or Q, X41 is E or Q, X42 is A, D, or P, X43 is A, L, or V, X44 is A or S, X45 is G or V, X46 is L or P, X47 is E or Q, X48 is R or S, X49 is A, I, or V, X50 is N or S, X51 is H or Q, preferably Q, X52 is H or K, X53 is K or Q, X54 is A or P, and X55 is L or M.

Embodiment 20. The monoclonal antibody according to Embodiment 16, wherein the VL chain comprises a sequence having a percent identity of at least about 65% up to 100% to SEQ ID NO:4.

Embodiment 21. The monoclonal antibody according to Embodiment 16, wherein the VL chain comprises a sequence selected from the group consisting of: SEQ ID NO:4, SEQ ID NO:5, and SEQ ID NO:6.

Embodiment 22. The monoclonal antibody according to Embodiment 16, wherein the VL chain comprises SEQ ID NO:32, SEQ ID NO:65, or SEQ ID NO:67.

Embodiment 23. The monoclonal antibody according to any one of Embodiments 16 to 22, wherein the VH chain comprises WVRQAPG (SEQ ID NO:8), GLEW (SEQ ID NO:9), and/or VTVSSA (SEQ ID NO:10).

Embodiment 24. The monoclonal antibody according to any one of Embodiments 16 to 22, wherein the VH chain any one or more of the following sequences VQLX1QSG (SEQ ID NO:17), PGX2SX3X4X5SCX6ASGX7TF (SEQ ID NO:18), WVRQAPGX8GLEW (SEQ ID NO:19), WGX9GTX10VTVSSA (SEQ ID NO:20), SLX11X12X13DTAVYYCAR (SEQ ID NO:21), and RX14X15X16X17X18DX19SX20X21T (SEQ ID NO:22), wherein X1 to X21 are each independently any amino acid.

Embodiment 25. The monoclonal antibody according to any one of Embodiments 16 to 22, wherein the VH chain comprises any one or more of the following sequences VQLX1QSG (SEQ ID NO:17), PGX2SX3X4X5SCX6ASGX7TF (SEQ ID NO:18), WVRQAPGX8GLEW (SEQ ID NO:19), WGX9GTX10VTVSSA (SEQ ID NO:20), SLX11X12X13DTAVYYCAR (SEQ ID NO:21), and RX14X15X16X17X18DX19SX20X21T (SEQ ID NO:22), wherein X1 is V or G, preferably V, X2 is A or R, preferably A, X3 is L or V, preferably V, X4 is K or R, preferably K, X5 is L or V, preferably V, X6 is A or K, preferably K, X7 is F or Y, preferably Y, X8 is K or Q, preferably Q, X9 is R or Q, X10 is L or T, X11 is T, K, or R, X12 is A or S, X13 is E or D, X14 is F or V, X15 is T or V, X16 is I, F, or M, X17 is S or T, X18 is L, R, or T, X19 is N or T, preferably T, X20 is K, T, or V, and X21 is N or S, preferably S.

Embodiment 26. The monoclonal antibody according to any one of Embodiments 16 to 22, wherein the VH chain comprises a sequence having a percent identity of about 75% to about 100%, preferably about 80% to about 100%, more preferably about 90% to 100%, even more preferably about 95% to about 100%, and most preferably about 99% to 100% to SEQ ID NO:2.

Embodiment 27. The monoclonal antibody according to any one of Embodiments 16 to 22, wherein the VH chain comprises SEQ ID NO:68, SEQ ID NO:69, or SEQ ID NO:70.

Embodiment 28. The monoclonal antibody according to any one of Embodiments 16 to 22, wherein the VH chain comprises a sequence having a percent identity of at least about 90% up to 100%, preferably about 91% up to 100%, more preferably about 95% up to 100%, even more preferably about 97% up to 100%, and most preferably about 99% up to 100% to SEQ ID NO:1.

Embodiment 29. The monoclonal antibody according to any one of Embodiments 16 to 28, wherein the VH chain comprises at least 10, 20, 30, 40, or 50 consecutive amino acid residues of SEQ ID NO:23.

Embodiment 30. The monoclonal antibody according to any one of Embodiments 16 to 28, wherein the VH chain comprises SEQ ID NO:23.

Embodiment 31. The monoclonal antibody according to any one of Embodiments 16 to 30, wherein the IgE epitope recognized by the monoclonal antibody comprises at least 10 consecutive amino acid residues of SEQ ID NO:33.

Embodiment 32. The monoclonal antibody according to any one of Embodiments 16 to 30, wherein the IgE epitope recognized by the monoclonal antibody comprises, consists essentially of, or consists of one or more of the following sequences: SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

Embodiment 33. The monoclonal antibody according to any one of Embodiments 16 to 30, wherein the IgE epitope recognized by the monoclonal antibody comprises at least one of the following sequences: SEQ ID NO:35, SEQ ID NO:39, SEQ ID NO:42, and SEQ ID NO:36.

Embodiment 34. The monoclonal antibody according to any one of Embodiments 16 to 33, wherein the antibody is a humanized antibody.

Embodiment 35. The monoclonal antibody according to any one of Embodiments 16 to 34, wherein the monoclonal antibody binds to human IgE when bound to human FcɛRI or a high affinity IgE receptor.

Embodiment 36. The monoclonal antibody according to any one of Embodiments 16 to 34, wherein the antibody binds to human IgE with a binding affinity of about $1\times10^{-5}$ M to about $1\times10^{-9}$ M Kd, about $1\times10^{-6}$ M to about $1\times10^{-9}$ M Kd, or about $5\times10^{-5}$ to about $7\times10^{-8}$ M Kd.

Embodiment 37. The monoclonal antibody according to any one of Embodiments 16 to 36, wherein the antibody is E59, E14, E17, E23, S91, or H6.2.

Embodiment 38. A composition comprising one or more hLAAIGEs according to any one of Embodiments 16 to 37.

Embodiment 39. The composition according to Embodiment 38, and further comprising a pharmaceutically acceptable carrier.

Embodiment 40. A method of treating a subject for an IgF-mediated disorder, which comprises administering to the subject one or more hLAAIGEs according to any one of Embodiments 16 to 37 or a composition according to Embodiment 38 or Embodiment 39.

Embodiment 41. The method according to Embodiment 40, wherein the IgE-mediated disorder is asthma, allergic rhinitis, atopic dermatitis, urticaria, angioedema, or anaphylactic hypersensitivity.

Embodiment 42. A method for treating or inhibiting an allergic reaction in a subject, which comprises administering to the subject one or more hLAAIGEs according to any one of Embodiments 16 to 37 or a composition according to Embodiment 38 or Embodiment 39.

Embodiment 43. The method according to any one of Embodiments 40 to 42, wherein the one or more antibodies are administered to the subject in a therapeutically effective amount.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An antibody selected from the group consisting of: a) an antibody comprising SEQ ID NO: 1 and SEQ ID NO: 3; b) an antibody comprising SEQ ID NO: 58 and SEQ ID NO: 59; c) an antibody comprising SEQ ID NO: 60 and SEQ ID NO: 61; d) an antibody comprising SEQ ID NO: 62 and SEQ ID NO: 63; e) an antibody comprising SEQ ID NO: 64 and SEQ ID NO: 65; and f) an antibody comprising SEQ ID NO: 66 and SEQ ID NO: 67.

2. A composition comprising one or more antibodies according to claim 1.

3. A method for treating or inhibiting an allergic reaction in a subject, which comprises administering to the subject one or more antibodies according to claim 1.

4. A method for treating or inhibiting a food allergy in a subject, which comprises administering to the subject one or more antibodies according to claim 1.

5. A method for treating or inhibiting asthma in a subject, which comprises administering to the subject one or more antibodies according to claim 1.

6. A method for treating or inhibiting allergic rhinitis in a subject, which comprises administering to the subject one or more antibodies according to claim 1.

7. A method for treating or inhibiting atopic dermatitis in a subject, which comprises administering to the subject one or more antibodies according to claim 1.

8. A method for treating or inhibiting urticaria in a subject, which comprises administering to the subject one or more antibodies according to claim 1.

9. A method for treating or inhibiting angioedema in a subject, which comprises administering to the subject one or more antibodies according to claim 1.

10. A method for treating or inhibiting anaphylactic hypersensitivity in a subject, which comprises administering to the subject one or more antibodies according to claim 1.

11. An antibody comprising SEQ ID NO: 1 and SEQ ID NO: 3.

12. A composition comprising the antibody according to claim 11.

13. A method for treating or inhibiting an allergic reaction in a subject, which comprises administering to the subject the antibody according to claim 11.

14. A method for treating or inhibiting a food allergy in a subject, which comprises administering to the subject the antibody according to claim 11.

15. A method for treating or inhibiting asthma in a subject, which comprises administering to the subject the antibody according to claim 11.

16. A method for treating or inhibiting allergic rhinitis in a subject, which comprises administering to the subject the antibody according to claim 11.

17. A method for treating or inhibiting atopic dermatitis in a subject, which comprises administering to the subject the antibody according to claim 11.

18. A method for treating or inhibiting urticaria in a subject, which comprises administering to the subject the antibody according to claim 11.

19. A method for treating or inhibiting angioedema in a subject, which comprises administering to the subject the antibody according to claim 11.

20. A method for treating or inhibiting anaphylactic hypersensitivity in a subject, which comprises administering to the subject the antibody according to claim 11.

* * * * *

SEQUENCE LISTING

```
<160> NUMBER OF SEQ ID NOS: 84

<210> SEQ ID NO 1
<211> LENGTH: 448
<212> TYPE: PRT
<213> ORGANISM: Artificial Sequence
<220> FEATURE:
<223> OTHER INFORMATION: Monoclonal anti-IgE antibody clone E59 VH chain

<400> SEQUENCE: 1

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Ala Ala Ser His Thr Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 2
<211> LENGTH: 159
<212> TYPE: PRT
<213> ORGANISM: Artificial Sequence
<220> FEATURE:
<223> OTHER INFORMATION: Monoclonal anti-IgE antibody VH chain

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Ala Ala Ser His Thr Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp
145                 150                 155
```

```
<210> SEQ ID NO 3
<211> LENGTH: 218
<212> TYPE: PRT
<213> ORGANISM: Artificial Sequence
<220> FEATURE:
<223> OTHER INFORMATION: Monoclonal anti-IgE antibody VL chain

<400> SEQUENCE: 3

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Ser His Ser Tyr Met His Trp Tyr Gln Gln Lys Pro Gly Gln Pro Pro
        35                  40                  45

Lys Leu Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 34
<212> TYPE: PRT
<213> ORGANISM: Artificial Sequence
<220> FEATURE:
<223> OTHER INFORMATION: Monoclonal anti-IgE antibody VL chain

<400> SEQUENCE: 4

Tyr Met His Trp Tyr Gln Gln Lys Pro Gly Gln Pro Pro Lys Leu Leu
1               5                   10                  15

Ile Tyr Tyr Ala Ser Asn Leu Glu Ser Gly Val Pro Asp Arg Phe Ser
            20                  25                  30

Gly Ser

<210> SEQ ID NO 5
<211> LENGTH: 34
<212> TYPE: PRT
<213> ORGANISM: Artificial Sequence
<220> FEATURE:
<223> OTHER INFORMATION: Monoclonal anti-IgE antibody VL chain

<400> SEQUENCE: 5
```

Tyr Met His Trp Tyr Gln Gln Lys Pro Gly Gln Pro Pro Lys Leu Leu
1               5                   10                  15

Ile Tyr Tyr Ala Ser Asn Leu Lys Ala Gly Val Pro Asp Arg Phe Ser
            20                  25                  30

Gly Ser

<210> SEQ ID NO 6
<211> LENGTH: 34
<212> TYPE: PRT
<213> ORGANISM: Artificial Sequence
<220> FEATURE:
<223> OTHER INFORMATION: Monoclonal anti-IgE antibody VL chain

<400> SEQUENCE: 6

Tyr Val Ser Trp Tyr Gln Gln His Pro Gly Lys Ala Pro Lys Leu Met
1               5                   10                  15

Ile Tyr Glu Val Ser Lys Arg Pro Ser Gly Val Pro Asp Arg Phe Ser
            20                  25                  30

Gly Ser

<210> SEQ ID NO 7
<211> LENGTH: 9
<212> TYPE: PRT
<213> ORGANISM: Artificial Sequence
<220> FEATURE:
<223> OTHER INFORMATION: Monoclonal anti-IgE antibody VH chain

<400> SEQUENCE: 7

Asp Thr Ala Val Tyr Tyr Cys Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Monoclonal anti-IgE antibody VH chain

<400> SEQUENCE: 8

Trp Val Arg Gln Ala Pro Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Monoclonal anti-IgE antibody VH chain

<400> SEQUENCE: 9

Gly Leu Glu Trp
1

<210> SEQ ID NO 10
<211> LENGTH: 6
<212> TYPE: PRT
<213> ORGANISM: Artificial Sequence
<220> FEATURE:
<223> OTHER INFORMATION: Monoclonal anti-IgE antibody VH chain

<400> SEQUENCE: 10

Val Thr Val Ser Ser Ala
1               5

```
<210> SEQ ID NO 11
<211> LENGTH: 5
<212> TYPE: PRT
<213> ORGANISM: Artificial Sequence
<220> FEATURE:
<223> OTHER INFORMATION: Monoclonal anti-IgE antibody VL chain

<400> SEQUENCE: 11

Leu Gln Ala Glu Asp
1               5

<210> SEQ ID NO 12
<211> LENGTH: 5
<212> TYPE: PRT
<213> ORGANISM: Artificial Sequence
<220> FEATURE:
<223> OTHER INFORMATION: Monoclonal anti-IgE antibody VL chain

<400> SEQUENCE: 12

Ala Ala Pro Ser Val
1               5

<210> SEQ ID NO 13
<211> LENGTH: 4
<212> TYPE: PRT
<213> ORGANISM: Artificial Sequence
<220> FEATURE:
<223> OTHER INFORMATION: Monoclonal anti-IgE antibody VL chain

<400> SEQUENCE: 13

Gly Thr Lys Leu
1

<210> SEQ ID NO 14
<211> LENGTH: 5
<212> TYPE: PRT
<213> ORGANISM: Artificial Sequence
<220> FEATURE:
<223> OTHER INFORMATION: Monoclonal anti-IgE antibody VL chain

<400> SEQUENCE: 14

Arg Phe Ser Gly Ser
1               5

<210> SEQ ID NO 15
<211> LENGTH: 122
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (1)..(1)
<223> OTHER INFORMATION: Xaa may be present or absent, and if present,
      Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(20)
```

```
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (48)..(50)
<223> OTHER INFORMATION: Xaa can be any naturally occurring amino acid
<220> FEATURE:
<221> NAME/KEY: misc_feature
<222> LOCATION: (52)..(55)
<223> OTHER INFORMATION: Xaa can be any naturally occurring amino acid
<220> FEATURE:
<221> NAME/KEY: misc_feature
<222> LOCATION: (57)..(59)
<223> OTHER INFORMATION: Xaa can be any naturally occurring amino acid
<220> FEATURE:
<221> NAME/KEY: misc_feature
<222> LOCATION: (61)..(66)
<223> OTHER INFORMATION: Xaa can be any naturally occurring amino acid
<220> FEATURE:
<221> NAME/KEY: misc_feature
<222> LOCATION: (68)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (79)..(84)
<223> OTHER INFORMATION: Xaa can be any naturally occurring amino acid
<220> FEATURE:
<221> NAME/KEY: misc_feature
<222> LOCATION: (87)..(89)
<223> OTHER INFORMATION: Xaa can be any naturally occurring amino acid
<220> FEATURE:
<221> NAME/KEY: MISC_FEATURE
<222> LOCATION: (99)..(109)
<223> OTHER INFORMATION: Xaa can be any naturally occurring amino acid
      and up to two Xaa may be absent
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 15

Xaa Val Gln Leu Xaa Gln Ser Gly Xaa Xaa Xaa Xaa Pro Gly Xaa
1               5                   10                  15

Ser Xaa Xaa Xaa Ser Cys Xaa Ala Ser Gly Xaa Thr Phe Xaa Xaa Xaa
            20                  25                  30

Xaa Xaa Xaa Trp Val Arg Gln Ala Pro Gly Xaa Gly Leu Glu Trp Xaa
        35                  40                  45

Xaa Xaa Ile Xaa Xaa Xaa Xaa Gly Xaa Xaa Xaa Tyr Xaa Xaa Xaa Xaa
```

50                  55                  60
Xaa Xaa Arg Xaa Xaa Xaa Xaa Asp Xaa Ser Xaa Xaa Thr Xaa Xaa
65                  70                  75                  80

Xaa Xaa Xaa Xaa Ser Leu Xaa Xaa Xaa Asp Thr Ala Val Tyr Tyr Cys
                85                  90                  95

Ala Arg Xaa Xaa Xaa Xaa Xaa Xaa Xaa Xaa Xaa Trp Gly Xaa
            100                 105                 110

Gly Thr Xaa Val Thr Val Ser Ser Ala Ser
        115                 120

<210> SEQ ID NO 16
<211> LENGTH: 226
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is present or absent, and if present, Xaa
      can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (24)..(26)
<223> OTHER INFORMATION: Xaa can be any naturally occurring amino acid
      and up to one Xaa can be absent
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: MISC_FEATURE
<222> LOCATION: (31)..(41)
<223> OTHER INFORMATION: Xaa can be any naturally occurring amino acid
      and up to two Xaa can be absent
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (47)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: MISC_FEATURE
<222> LOCATION: (55)..(58)

```
<223> OTHER INFORMATION: Xaa can be any naturally occurring amino acid
      and up to two Xaa can be absent
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: MISC_FEATURE
<222> LOCATION: (64)..(67)
<223> OTHER INFORMATION: Xaa can be any naturally occurring amino acid
      and up to two Xaa can be absent
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: MISC_FEATURE
<222> LOCATION: (96)..(97)
<223> OTHER INFORMATION: Xaa can be any naturally occurring amino acid
      and up to two Xaa can be absent
<220> FEATURE:
<221> NAME/KEY: MISC_FEATURE
<222> LOCATION: (99)..(106)
<223> OTHER INFORMATION: Xaa can be any naturally occurring amino acid
      and up to two Xaa can be absent
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: MISC_FEATURE
<222> LOCATION: (114)..(120)
<223> OTHER INFORMATION: Xaa can be any naturally occurring amino acid
      and up to four Xaa can be absent
<220> FEATURE:
<221> NAME/KEY: misc_feature
<222> LOCATION: (126)..(127)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (136)..(139)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid
<220> FEATURE:
<221> NAME/KEY: misc_feature
<222> LOCATION: (146)..(148)
<223> OTHER INFORMATION: Xaa can be any naturally occurring amino acid
<220> FEATURE:
```

```
<221> NAME/KEY: misc_feature
<222> LOCATION: (152)..(155)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: MISC_FEATURE
<222> LOCATION: (162)..(167)
<223> OTHER INFORMATION: Xaa can be any naturally occurring amino acid
      and up to one Xaa can be absent
<220> FEATURE:
<221> NAME/KEY: MISC_FEATURE
<222> LOCATION: (169)..(171)
<223> OTHER INFORMATION: Xaa can be any naturally occurring amino acid
      and up to two Xaa can be absent
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (176)..(183)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (193)..(199)
<223> OTHER INFORMATION: Xaa can be any naturally occurring amino acid
<220> FEATURE:
<221> NAME/KEY: misc_feature
<222> LOCATION: (201)..(202)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: MISC_FEATURE
<222> LOCATION: (212)..(213)
<223> OTHER INFORMATION: Xaa can be any naturally occurring amino acid
      and up to two Xaa can be absent
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (219)..(223)
<223> OTHER INFORMATION: Xaa can be any naturally occurring amino acid
<220> FEATURE:
```

<221> NAME/KEY: MISC_FEATURE
<222> LOCATION: (226)..(226)
<223> OTHER INFORMATION: Xaa is present or absent, and if present, Xaa
      can be any naturally occurring amino acid

<400> SEQUENCE: 16

Xaa Xaa Xaa Xaa Thr Gln Xaa Pro Xaa Ser Xaa Xaa Xaa Ser Xaa Gly
1               5                   10                  15

Xaa Xaa Xaa Thr Ile Xaa Cys Xaa Xaa Xaa Ser Xaa Xaa Val Xaa Xaa
            20                  25                  30

Xaa Xaa Xaa Xaa Xaa Xaa Xaa Xaa Gln Xaa Xaa Pro Gly Xaa Xaa
        35                  40                  45

Pro Lys Leu Xaa Ile Tyr Xaa Xaa Xaa Ser Xaa Xaa Xaa Ser Xaa
    50                  55                  60

Xaa Xaa Xaa Arg Phe Ser Gly Ser Xaa Ser Gly Xaa Xaa Xaa Leu
65              70                  75                  80

Thr Xaa Ser Xaa Leu Gln Ala Glu Asp Xaa Ala Xaa Tyr Tyr Cys Xaa
        85                  90                  95

Xaa Gln Xaa Xaa Xaa Xaa Xaa Xaa Phe Gly Xaa Gly Thr Lys
            100                 105                 110

Leu Xaa Xaa Xaa Xaa Xaa Xaa Ala Ala Pro Ser Val Xaa Xaa Phe
        115                 120                 125

Pro Pro Ser Xaa Glu Xaa Leu Xaa Xaa Xaa Ala Xaa Xaa Val Cys
130                 135                 140

Leu Xaa Xaa Xaa Phe Tyr Pro Xaa Xaa Xaa Val Xaa Trp Lys Xaa
145                 150                 155                 160

Asp Xaa Xaa Xaa Xaa Xaa Gly Xaa Xaa Xaa Glu Xaa Xaa Thr Xaa
                165                 170                 175

Xaa Xaa Xaa Xaa Xaa Xaa Xaa Tyr Xaa Xaa Ser Ser Xaa Leu Xaa Leu
            180                 185                 190

Xaa Xaa Xaa Xaa Xaa Xaa Xaa His Xaa Xaa Tyr Xaa Cys Xaa Val Thr
        195                 200                 205

His Xaa Gly Xaa Xaa Ser Xaa Val Xaa Lys Xaa Xaa Xaa Xaa Xaa Glu
210                 215                 220

Cys Xaa
225

<210> SEQ ID NO 17
<211> LENGTH: 7
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (4)..(4)
<223> OTHER INFORMATION: Xaa is any amino acid, preferably Xaa is Val or
      Gly, preferably Xaa is Val

<400> SEQUENCE: 17

Val Gln Leu Xaa Gln Ser Gly
1               5

<210> SEQ ID NO 18
<211> LENGTH: 16
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE

```
<222> LOCATION: (3)..(3)
<223> OTHER INFORMATION: Xaa is any amino acid, preferably Xaa is Ala or
      Arg, more preferably Xaa is Ala
<220> FEATURE:
<221> NAME/KEY: MISC_FEATURE
<222> LOCATION: (5)..(5)
<223> OTHER INFORMATION: Xaa is any amino acid, preferably Xaa is Leu or
      Val, more preferably Xaa is Val
<220> FEATURE:
<221> NAME/KEY: MISC_FEATURE
<222> LOCATION: (6)..(6)
<223> OTHER INFORMATION: Xaa is any amino acid, preferably Xaa is Lys or
      Arg, more preferably Xaa is Lys
<220> FEATURE:
<221> NAME/KEY: MISC_FEATURE
<222> LOCATION: (7)..(7)
<223> OTHER INFORMATION: Xaa is any amino acid, preferably Xaa is Leu or
      Val, more preferably Xaa is Val
<220> FEATURE:
<221> NAME/KEY: MISC_FEATURE
<222> LOCATION: (10)..(10)
<223> OTHER INFORMATION: Xaa is any amino acid, preferably Xaa is Ala or
      Lys, more preferably Xaa is Lys
<220> FEATURE:
<221> NAME/KEY: MISC_FEATURE
<222> LOCATION: (14)..(14)
<223> OTHER INFORMATION: Xaa is any amino acid, preferably Xaa is Phe or
      Tyr, more preferably Xaa is Tyr

<400> SEQUENCE: 18

Pro Gly Xaa Ser Xaa Xaa Xaa Ser Cys Xaa Ala Ser Gly Xaa Thr Phe
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (8)..(8)
<223> OTHER INFORMATION: Xaa is any amino acid, preferably Xaa is Lys or
      Gln, preferably Gln

<400> SEQUENCE: 19

Trp Val Arg Gln Ala Pro Gly Xaa Gly Leu Glu Trp
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (3)..(3)
<223> OTHER INFORMATION: Xaa is any amino acid, preferably Xaa is Arg or
      Gln
<220> FEATURE:
<221> NAME/KEY: MISC_FEATURE
<222> LOCATION: (6)..(6)
<223> OTHER INFORMATION: Xaa is any amino acid, preferably Xaa is Leu or
      Thr

<400> SEQUENCE: 20

Trp Gly Xaa Gly Thr Xaa Val Thr Val Ser Ser Ala
1               5                   10

<210> SEQ ID NO 21
<211> LENGTH: 14
<212> TYPE: PRT
```

```
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (3)..(3)
<223> OTHER INFORMATION: Xaa is any amino acid, preferably Xaa is Thr,
      Lys, or Arg
<220> FEATURE:
<221> NAME/KEY: MISC_FEATURE
<222> LOCATION: (4)..(4)
<223> OTHER INFORMATION: Xaa is any amino acid, preferably Xaa is Ala or
      Ser
<220> FEATURE:
<221> NAME/KEY: MISC_FEATURE
<222> LOCATION: (5)..(5)
<223> OTHER INFORMATION: Xaa is any amino acid, preferably Xaa is Glu or
      Asp

<400> SEQUENCE: 21

Ser Leu Xaa Xaa Xaa Asp Thr Ala Val Tyr Tyr Cys Ala Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (2)..(2)
<223> OTHER INFORMATION: Xaa is any amino acid, preferably Xaa is Phe or
      Val
<220> FEATURE:
<221> NAME/KEY: MISC_FEATURE
<222> LOCATION: (3)..(3)
<223> OTHER INFORMATION: Xaa is any amino acid, preferably Xaa is Thr or
      Val
<220> FEATURE:
<221> NAME/KEY: MISC_FEATURE
<222> LOCATION: (4)..(4)
<223> OTHER INFORMATION: Xaa is any amino acid, preferably Xaa is Ile,
      Phe, or Met
<220> FEATURE:
<221> NAME/KEY: MISC_FEATURE
<222> LOCATION: (5)..(5)
<223> OTHER INFORMATION: Xaa is any amino acid, preferably Xaa is Ser or
      Thr
<220> FEATURE:
<221> NAME/KEY: MISC_FEATURE
<222> LOCATION: (6)..(6)
<223> OTHER INFORMATION: Xaa is any amino acid, preferably Xaa is Leu,
      Arg, or Thr
<220> FEATURE:
<221> NAME/KEY: MISC_FEATURE
<222> LOCATION: (8)..(8)
<223> OTHER INFORMATION: Xaa is any amino acid, preferably Xaa is Asn or
      Thr, more preferably Xaa is Thr
<220> FEATURE:
<221> NAME/KEY: MISC_FEATURE
<222> LOCATION: (10)..(10)
<223> OTHER INFORMATION: Xaa is any amino acid, preferably Xaa is Lys,
      Thr, or Val
<220> FEATURE:
<221> NAME/KEY: MISC_FEATURE
<222> LOCATION: (11)..(11)
<223> OTHER INFORMATION: Xaa is any amino acid, preferably Xaa is Asn or
      Ser, more preferably Xaa is Ser

<400> SEQUENCE: 22

Arg Xaa Xaa Xaa Xaa Xaa Asp Xaa Ser Xaa Xaa Thr
1               5                   10

<210> SEQ ID NO 23
```

<211> LENGTH: 328
<212> TYPE: PRT
<213> ORGANISM: Artificial Sequence
<220> FEATURE:
<223> OTHER INFORMATION: Monoclonal anti-IgE antibody VH chain

<400> SEQUENCE: 23

```
Thr Lys Gly Pro Ser Val Phe Pro Leu Ala Pro Ser Ser Lys Ser Thr
  1               5                  10                  15
Ser Gly Gly Thr Ala Ala Leu Gly Cys Leu Val Lys Asp Tyr Phe Pro
                 20                  25                  30
Glu Pro Val Thr Val Ser Trp Asn Ser Gly Ala Leu Thr Ser Gly Val
             35                  40                  45
His Thr Phe Pro Ala Val Leu Gln Ser Ser Gly Leu Tyr Ser Leu Ser
         50                  55                  60
Ser Val Val Thr Val Pro Ser Ser Ser Leu Gly Thr Gln Thr Tyr Ile
 65                  70                  75                  80
Cys Asn Val Asn His Lys Pro Ser Asn Thr Lys Val Asp Lys Lys Val
                 85                  90                  95
Glu Pro Lys Ser Cys Asp Lys Thr His Thr Cys Pro Pro Cys Pro Ala
            100                 105                 110
Pro Glu Leu Leu Gly Gly Pro Ser Val Phe Leu Phe Pro Pro Lys Pro
            115                 120                 125
Lys Asp Thr Leu Met Ile Ser Arg Thr Pro Glu Val Thr Cys Val Val
130                 135                 140
Val Asp Val Ser His Glu Asp Pro Glu Val Lys Phe Asn Trp Tyr Val
145                 150                 155                 160
Asp Gly Val Glu Val His Asn Ala Lys Thr Lys Pro Arg Glu Glu Gln
                165                 170                 175
Tyr Asn Ser Thr Tyr Arg Val Val Ser Val Leu Thr Val Leu His Gln
            180                 185                 190
Asp Trp Leu Asn Gly Lys Glu Tyr Lys Cys Lys Val Ser Asn Lys Ala
            195                 200                 205
Leu Pro Ala Pro Ile Glu Lys Thr Ile Ser Lys Ala Lys Gly Gln Pro
        210                 215                 220
Arg Glu Pro Gln Val Tyr Thr Leu Pro Pro Ser Arg Asp Glu Leu Thr
225                 230                 235                 240
Lys Asn Gln Val Ser Leu Thr Cys Leu Val Lys Gly Phe Tyr Pro Ser
                245                 250                 255
Asp Ile Ala Val Glu Trp Glu Ser Asn Gly Gln Pro Glu Asn Asn Tyr
            260                 265                 270
Lys Thr Thr Pro Pro Val Leu Asp Ser Asp Gly Ser Phe Phe Leu Tyr
        275                 280                 285
Ser Lys Leu Thr Val Asp Lys Ser Arg Trp Gln Gln Gly Asn Val Phe
    290                 295                 300
Ser Cys Ser Val Met His Glu Ala Leu His Asn His Tyr Thr Gln Lys
305                 310                 315                 320
Ser Leu Ser Leu Ser Pro Gly Lys
                325
```

<210> SEQ ID NO 24
<211> LENGTH: 8
<212> TYPE: PRT
<213> ORGANISM: Artificial Sequence
<220> FEATURE:
<223> OTHER INFORMATION: Monoclonal anti-IgE antibody VL chain
<220> FEATURE:

```
<221> NAME/KEY: MISC_FEATURE
<222> LOCATION: (6)..(6)
<223> OTHER INFORMATION: Xaa is any amino acid, preferably Xaa is Gly or
      Lys

<400> SEQUENCE: 24

Arg Phe Ser Gly Ser Xaa Ser Gly
1               5

<210> SEQ ID NO 25
<211> LENGTH: 15
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (3)..(3)
<223> OTHER INFORMATION: Xaa is any amino acid, preferably Xaa is Ile or
      Val
<220> FEATURE:
<221> NAME/KEY: MISC_FEATURE
<222> LOCATION: (5)..(5)
<223> OTHER INFORMATION: Xaa is any amino acid, preferably Xaa is Gly or
      Ser
<220> FEATURE:
<221> NAME/KEY: MISC_FEATURE
<222> LOCATION: (11)..(11)
<223> OTHER INFORMATION: Xaa is any amino acid, preferably Xaa is Glu or
      Val
<220> FEATURE:
<221> NAME/KEY: MISC_FEATURE
<222> LOCATION: (13)..(13)
<223> OTHER INFORMATION: Xaa is any amino acid, preferably Xaa is Asp or
      Val

<400> SEQUENCE: 25

Leu Thr Xaa Ser Xaa Leu Gln Ala Glu Asp Xaa Ala Xaa Tyr Tyr
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (3)..(3)
<223> OTHER INFORMATION: Xaa is any amino acid, preferably Xaa is Gly,
      Ser, or Gln

<400> SEQUENCE: 26

Phe Gly Xaa Gly Thr Lys Leu
1               5

<210> SEQ ID NO 27
<211> LENGTH: 15
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (6)..(6)
<223> OTHER INFORMATION: Xaa is any amino acid, preferably Xaa is Phe or
      Thr
<220> FEATURE:
<221> NAME/KEY: MISC_FEATURE
<222> LOCATION: (7)..(7)
<223> OTHER INFORMATION: Xaa is any amino acid, preferably Xaa is Ile or
      Leu
<220> FEATURE:
```

```
<221> NAME/KEY: MISC_FEATURE
<222> LOCATION: (12)..(12)
<223> OTHER INFORMATION: Xaa is any amino acid, preferably Xaa is Asp or
      Ser
<220> FEATURE:
<221> NAME/KEY: MISC_FEATURE
<222> LOCATION: (14)..(14)
<223> OTHER INFORMATION: Xaa is any amino acid, preferably Xaa is Glu or
      Gln

<400> SEQUENCE: 27

Ala Ala Pro Ser Val Xaa Xaa Phe Pro Pro Ser Xaa Glu Xaa Leu
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is any amino acid, preferably Xaa is Ser or
      Thr
<220> FEATURE:
<221> NAME/KEY: MISC_FEATURE
<222> LOCATION: (3)..(3)
<223> OTHER INFORMATION: Xaa is any amino acid, preferably Xaa is Leu or
      Val
<220> FEATURE:
<221> NAME/KEY: MISC_FEATURE
<222> LOCATION: (7)..(7)
<223> OTHER INFORMATION: Xaa is any amino acid, preferably Xaa is Ile or
      Leu
<220> FEATURE:
<221> NAME/KEY: MISC_FEATURE
<222> LOCATION: (8)..(8)
<223> OTHER INFORMATION: Xaa is any amino acid, preferably Xaa is Asn or
      Ser
<220> FEATURE:
<221> NAME/KEY: MISC_FEATURE
<222> LOCATION: (9)..(9)
<223> OTHER INFORMATION: Xaa is any amino acid, preferably Xaa is Asp or
      Asn

<400> SEQUENCE: 28

Ala Xaa Xaa Val Cys Leu Xaa Xaa Xaa Phe Tyr Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is any amino acid, preferably Xaa is Lys or
      Arg
<220> FEATURE:
<221> NAME/KEY: MISC_FEATURE
<222> LOCATION: (3)..(3)
<223> OTHER INFORMATION: Xaa is any amino acid, preferably Xaa is Ser or
      Val
<220> FEATURE:
<221> NAME/KEY: MISC_FEATURE
<222> LOCATION: (5)..(5)
<223> OTHER INFORMATION: Xaa is any amino acid, preferably Xaa is Ala or
      Ser
<220> FEATURE:
<221> NAME/KEY: MISC_FEATURE
<222> LOCATION: (7)..(7)
<223> OTHER INFORMATION: Xaa is any amino acid, preferably Xaa is Glu or
```

```
            Gln
<220> FEATURE:
<221> NAME/KEY: MISC_FEATURE
<222> LOCATION: (11)..(11)
<223> OTHER INFORMATION: Xaa is any amino acid, preferably Xaa is Glu or
      Gln

<400> SEQUENCE: 29

His Xaa Xaa Tyr Xaa Cys Xaa Val Thr His Xaa Gly
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is any amino acid, preferably Xaa is Ala,
      Asp, or Pro
<220> FEATURE:
<221> NAME/KEY: MISC_FEATURE
<222> LOCATION: (4)..(4)
<223> OTHER INFORMATION: Xaa is any amino acid, preferably Xaa is Ala,
      Leu, or Val
<220> FEATURE:
<221> NAME/KEY: MISC_FEATURE
<222> LOCATION: (5)..(5)
<223> OTHER INFORMATION: Xaa is any amino acid, preferably Xaa is Ala or
      Ser
<220> FEATURE:
<221> NAME/KEY: MISC_FEATURE
<222> LOCATION: (6)..(6)
<223> OTHER INFORMATION: Xaa is any amino acid, preferably Xaa is Gly or
      Val
<220> FEATURE:
<221> NAME/KEY: MISC_FEATURE
<222> LOCATION: (8)..(8)
<223> OTHER INFORMATION: Xaa is any amino acid, preferably Xaa is Leu or
      Pro
<220> FEATURE:
<221> NAME/KEY: MISC_FEATURE
<222> LOCATION: (10)..(10)
<223> OTHER INFORMATION: Xaa is any amino acid, preferably Xaa is Glu or
      Gln
<220> FEATURE:
<221> NAME/KEY: MISC_FEATURE
<222> LOCATION: (11)..(11)
<223> OTHER INFORMATION: Xaa is any amino acid, preferably Xaa is Arg or
      Ser
<220> FEATURE:
<221> NAME/KEY: MISC_FEATURE
<222> LOCATION: (12)..(12)
<223> OTHER INFORMATION: Xaa is any amino acid, preferably Xaa is Ala,
      Ile, or Val
<220> FEATURE:
<221> NAME/KEY: MISC_FEATURE
<222> LOCATION: (15)..(15)
<223> OTHER INFORMATION: Xaa is any amino acid, preferably Xaa is Asn or
      Ser

<400> SEQUENCE: 30

Pro Xaa Ser Xaa Xaa Xaa Ser Xaa Gly Xaa Xaa Xaa Thr Ile Xaa Cys
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
```

```
<222> LOCATION: (2)..(2)
<223> OTHER INFORMATION: Xaa is any amino acid, preferably Xaa is His or
      Gln, more preferably Xaa is Gln
<220> FEATURE:
<221> NAME/KEY: MISC_FEATURE
<222> LOCATION: (3)..(3)
<223> OTHER INFORMATION: Xaa is any amino acid, preferably Xaa is His or
      Lys
<220> FEATURE:
<221> NAME/KEY: MISC_FEATURE
<222> LOCATION: (6)..(6)
<223> OTHER INFORMATION: Xaa is any amino acid, preferably Xaa is Lys or
      Gln
<220> FEATURE:
<221> NAME/KEY: MISC_FEATURE
<222> LOCATION: (7)..(7)
<223> OTHER INFORMATION: Xaa is any amino acid, preferably Xaa is Ala or
      Pro
<220> FEATURE:
<221> NAME/KEY: MISC_FEATURE
<222> LOCATION: (11)..(11)
<223> OTHER INFORMATION: Xaa is any amino acid, preferably Xaa is Leu or
      Met

<400> SEQUENCE: 31

Gln Xaa Xaa Pro Gly Xaa Xaa Pro Lys Leu Xaa Ile Tyr
1               5                   10

<210> SEQ ID NO 32
<211> LENGTH: 218
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (33)..(33)
<223> OTHER INFORMATION: Xaa is any amino acid, preferably Xaa is Ser or
      Ala
<220> FEATURE:
<221> NAME/KEY: MISC_FEATURE
<222> LOCATION: (59)..(59)
<223> OTHER INFORMATION: Xaa is any amino acid, preferably Xaa is Glu or
      Lys
<220> FEATURE:
<221> NAME/KEY: MISC_FEATURE
<222> LOCATION: (60)..(60)
<223> OTHER INFORMATION: Xaa is any amino acid, preferably Xaa is Ala or
      Ser

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Xaa His Ser Tyr Met His Trp Tyr Gln Gln Lys Pro Gly Gln Pro Pro
        35                  40                  45

Lys Leu Leu Ile Tyr Tyr Ala Ser Asn Leu Xaa Xaa Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

```
                130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 33
<211> LENGTH: 99
<212> TYPE: PRT
<213> ORGANISM: Artificial Sequence
<220> FEATURE:
<223> OTHER INFORMATION: Portion of human IgE sequence

<400> SEQUENCE: 33

```
Asn Pro Arg Gly Val Ser Ala Tyr Leu Ser Arg Pro Ser Pro Phe Asp
1               5                   10                  15

Leu Phe Ile Arg Lys Ser Pro Thr Ile Thr Cys Leu Val Val Asp Leu
            20                  25                  30

Ala Pro Ser Lys Gly Thr Val Asn Leu Thr Trp Ser Arg Ala Ser Gly
        35                  40                  45

Lys Pro Val Asn His Ser Thr Arg Lys Glu Lys Gln Arg Asn Gly
    50                  55                  60

Thr Leu Thr Val Thr Ser Thr Leu Pro Val Gly Thr Arg Asp Trp Ile
65                  70                  75                  80

Glu Gly Glu Thr Tyr Gln Cys Arg Val Thr His Pro His Leu Pro Arg
                85                  90                  95

Ala Leu Met
```

<210> SEQ ID NO 34
<211> LENGTH: 12
<212> TYPE: PRT
<213> ORGANISM: Artificial Sequence
<220> FEATURE:
<223> OTHER INFORMATION: Portion of human IgE sequence

<400> SEQUENCE: 34

```
Tyr Gln Cys Arg Val Thr His Pro His Leu Pro Arg
1               5                   10
```

<210> SEQ ID NO 35
<211> LENGTH: 15
<212> TYPE: PRT
<213> ORGANISM: Artificial Sequence
<220> FEATURE:
<223> OTHER INFORMATION: Portion of human IgE sequence

<400> SEQUENCE: 35

```
Tyr Gln Cys Arg Val Thr His Pro His Leu Pro Arg Ala Leu Met
1               5                   10                  15
```

<210> SEQ ID NO 36
<211> LENGTH: 14
<212> TYPE: PRT
<213> ORGANISM: Artificial Sequence
<220> FEATURE:

<223> OTHER INFORMATION: Portion of human IgE sequence

<400> SEQUENCE: 36

Glu Thr Tyr Gln Cys Arg Val Thr His Pro His Leu Pro Arg
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Portion of human IgE sequence

<400> SEQUENCE: 37

Glu Thr Tyr Gln Cys Arg Val Thr His Pro His Leu Pro Arg Ala Leu
1               5                   10                  15

Met

<210> SEQ ID NO 38
<211> LENGTH: 10
<212> TYPE: PRT
<213> ORGANISM: Artificial Sequence
<220> FEATURE:
<223> OTHER INFORMATION: Portion of human IgE sequence

<400> SEQUENCE: 38

Pro Arg Gly Val Ser Ala Tyr Leu Ser Arg
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Portion of human IgE sequence

<400> SEQUENCE: 39

Asn Pro Arg Gly Val Ser Ala Tyr Leu Ser Arg
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Portion of human IgE sequence

<400> SEQUENCE: 40

Pro Ser Pro Phe Asp Leu Phe Ile Arg Lys
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Portion of human IgE sequence

<400> SEQUENCE: 41

Arg Pro Ser Pro Phe Asp Leu Phe Ile
1               5

<210> SEQ ID NO 42
<211> LENGTH: 11
<212> TYPE: PRT
<213> ORGANISM: Artificial Sequence

```
<220> FEATURE:
<223> OTHER INFORMATION: Portion of human IgE sequence

<400> SEQUENCE: 42

Arg Pro Ser Pro Phe Asp Leu Phe Ile Arg Lys
1               5                   10

<210> SEQ ID NO 43
<211> LENGTH: 18
<212> TYPE: PRT
<213> ORGANISM: Artificial Sequence
<220> FEATURE:
<223> OTHER INFORMATION: Portion of human IgE sequence

<400> SEQUENCE: 43

Pro Arg Gly Val Ser Ala Tyr Leu Ser Arg Pro Ser Pro Phe Asp Leu
1               5                   10                  15

Phe Ile

<210> SEQ ID NO 44
<211> LENGTH: 20
<212> TYPE: PRT
<213> ORGANISM: Artificial Sequence
<220> FEATURE:
<223> OTHER INFORMATION: Portion of human IgE sequence

<400> SEQUENCE: 44

Pro Arg Gly Val Ser Ala Tyr Leu Ser Arg Pro Ser Pro Phe Asp Leu
1               5                   10                  15

Phe Ile Arg Lys
            20

<210> SEQ ID NO 45
<211> LENGTH: 21
<212> TYPE: PRT
<213> ORGANISM: Artificial Sequence
<220> FEATURE:
<223> OTHER INFORMATION: Portion of human IgE sequence

<400> SEQUENCE: 45

Asn Pro Arg Gly Val Ser Ala Tyr Leu Ser Arg Pro Ser Pro Phe Asp
1               5                   10                  15

Leu Phe Ile Arg Lys
            20

<210> SEQ ID NO 46
<211> LENGTH: 323
<212> TYPE: DNA
<213> ORGANISM: Artificial Sequence
<220> FEATURE:
<223> OTHER INFORMATION: Founder E17 VH sequence

<400> SEQUENCE: 46
cagtctggac ctgagctgaa gaagcctgga gagacagtca agatctcctg caaggcttcc      60
ggctacacct tcacaaacta tggcatgaac tgggtgaagc aggctccagg aaagggttta    120
aagtggatgg gctggatcaa cacctacaca ggcgagccca catatgctga tgacttcaag    180
ggacggtttg ccttctcttt ggaaacctct gccagcactg cctatttgca gatcaacaac    240
ctgaaaaatg aggacaccgc tacatacttc tgtgctagag gagctgcttc ccacacaatg    300
gattattggg gccaaggcac cac                                             323

<210> SEQ ID NO 47
```

<211> LENGTH: 107
<212> TYPE: PRT
<213> ORGANISM: Artificial Sequence
<220> FEATURE:
<223> OTHER INFORMATION: Founder E17 VH sequence

<400> SEQUENCE: 47

```
Gln Ser Gly Pro Glu Leu Lys Lys Pro Gly Glu Thr Val Lys Ile Ser
1               5                   10                  15

Cys Lys Ala Ser Gly Tyr Thr Phe Thr Asn Tyr Gly Met Asn Trp Val
            20                  25                  30

Lys Gln Ala Pro Gly Lys Gly Leu Lys Trp Met Gly Trp Ile Asn Thr
        35                  40                  45

Tyr Thr Gly Glu Pro Thr Tyr Ala Asp Asp Phe Lys Gly Arg Phe Ala
50                  55                  60

Phe Ser Leu Glu Thr Ser Ala Ser Thr Ala Tyr Leu Gln Ile Asn Asn
65                  70                  75                  80

Leu Lys Asn Glu Asp Thr Ala Thr Tyr Phe Cys Ala Arg Gly Ala Ala
                85                  90                  95

Ser His Thr Met Asp Tyr Trp Gly Gln Gly Thr
            100                 105
```

<210> SEQ ID NO 48
<211> LENGTH: 332
<212> TYPE: DNA
<213> ORGANISM: Artificial Sequence
<220> FEATURE:
<223> OTHER INFORMATION: Founder E17 VL sequence

<400> SEQUENCE: 48

```
gacattgtgc taacacagtc tcctgcttcc ttagctgtat ctctggggca gagagctacc      60
atctcatgca gggctagcca gtccgtgtct acaagctccc acgcctacat gcactggtat     120
cagcagaaac ccggacagcc acccaagctc ctgatcaagt atgctagcaa tctggagtct     180
ggggtgcctg ccaggttcag cggaagtggc tctgggacag acttcaccct caacatcgat     240
cctgtggagg aggaggacac tgccacatac tattgccagc acagttggga gattccttgg     300
accttcggcc agggcaccaa gctggaaatc aa                                    332
```

<210> SEQ ID NO 49
<211> LENGTH: 110
<212> TYPE: PRT
<213> ORGANISM: Artificial Sequence
<220> FEATURE:
<223> OTHER INFORMATION: Founder E17 VL sequence

<400> SEQUENCE: 49

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser His Ala Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile Asp
65                  70                  75                  80

Pro Val Glu Glu Glu Asp Thr Ala Thr Tyr Tyr Cys Gln His Ser Trp
                85                  90                  95
```

Glu Ile Pro Trp Thr Phe Gly Gln Gly Thr Lys Leu Glu Ile
                100                 105                 110

<210> SEQ ID NO 50
<211> LENGTH: 333
<212> TYPE: DNA
<213> ORGANISM: Artificial Sequence
<220> FEATURE:
<223> OTHER INFORMATION: Founder F11 VH sequence

<400> SEQUENCE: 50
caggttcagc tgcagcagtc tggagctgag ctggcgaggc ctggggcttc agtgaagctg      60
tcctgcaagg cttctggtta cacctttacc agctatggta taagctgggt gaagcagaga     120
actggacagg gccttgagtg gattggagag atcagcgctt acaatggtaa cacatactac     180
aatgagaagt tcaagggcaa ggccacactg actgcagaca atcctccag cacagcgtac      240 atggagctcc gcagcctgac atctgaggac tctgcggtct atttctgtgc gagagttagc     300
agctggccat actggtactt cgatctctgg ggc                                   333

<210> SEQ ID NO 51
<211> LENGTH: 111
<212> TYPE: PRT
<213> ORGANISM: Artificial Sequence
<220> FEATURE:
<223> OTHER INFORMATION: Founder F11 VH sequence

<400> SEQUENCE: 51

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Ser Ala Tyr Asn Gly Asn Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Val Ser Ser Trp Pro Tyr Trp Tyr Phe Asp Leu Trp Gly
            100                 105                 110

<210> SEQ ID NO 52
<211> LENGTH: 303
<212> TYPE: DNA
<213> ORGANISM: Artificial Sequence
<220> FEATURE:
<223> OTHER INFORMATION: Founder F11 VL sequence

<400> SEQUENCE: 52
acgcagccgc cctccgcgtc cgggtctcct ggacagtcag tcaccatctc ctgcactgga     60
accagcagtg acgttggtgc gtatgactat gtctcctggt accaacagca cccaggcaaa    120 gccccaaac tcatgattta tgaggtcagt aagcggccct caggggtccc tgatcgcttc     180
tctggctcca ttgacaagtc tggcaacacg gcctcctga ccgtctctgg ctccaggct     240 gaggatagct catatgccgg cagagttgat gtgttcggcg agggaccaa gctgaccgtc     300 cta                                                                   303

<210> SEQ ID NO 53
<211> LENGTH: 101
<212> TYPE: PRT
<213> ORGANISM: Artificial Sequence
<220> FEATURE:
<223> OTHER INFORMATION: Founder F11 VL sequence

<400> SEQUENCE: 53

```
Thr Gln Pro Pro Ser Ala Ser Gly Ser Pro Gly Gln Ser Val Thr Ile
1               5                   10                  15

Ser Cys Thr Gly Thr Ser Ser Asp Val Gly Ala Tyr Asp Tyr Val Ser
            20                  25                  30

Trp Tyr Gln Gln His Pro Gly Lys Ala Pro Lys Leu Met Ile Tyr Glu
        35                  40                  45

Val Ser Lys Arg Pro Ser Gly Val Pro Asp Arg Phe Ser Gly Ser Ile
    50                  55                  60

Asp Lys Ser Gly Asn Thr Ala Ser Leu Thr Val Ser Gly Leu Gln Ala
65                  70                  75                  80

Glu Asp Ser Ser Tyr Ala Gly Arg Val Asp Val Phe Gly Gly Gly Thr
                85                  90                  95

Lys Leu Thr Val Leu
            100
```

<210> SEQ ID NO 54
<211> LENGTH: 354
<212> TYPE: DNA
<213> ORGANISM: Artificial Sequence
<220> FEATURE:
<223> OTHER INFORMATION: Founder P6.2 VH sequence

<400> SEQUENCE: 54

```
caggtccagc tgcagcagtc tggagctgag ctggtaaggc ctgggacttc agtgaaggtg      60
tcctgcaagg cttctggata cgccttcact aattacttga tagagtgggt aaagcagagg     120
cctggacagg ccttgagtg gattggagtg attaatcctg gaagtggttt tacaaaatac      180
aatgagaagt tcaagggcaa ggcaacactg actgcagaca atcctccag cactgcctac      240 atgcacctca gcagcctgac atctgatgac tctgcggtct atttctgtgc aagagaagat     300
gtttactcct ggtttgctta ctggggccaa gggactctgg tcactgtctc tgca            354
```

<210> SEQ ID NO 55
<211> LENGTH: 118
<212> TYPE: PRT
<213> ORGANISM: Artificial Sequence
<220> FEATURE:
<223> OTHER INFORMATION: Founder P6.2 VH sequence

<400> SEQUENCE: 55

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Phe Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met His Leu Ser Ser Leu Thr Ser Asp Asp Ser Ala Val Tyr Phe Cys
                85                  90                  95
```

Ala Arg Glu Asp Val Tyr Ser Trp Phe Ala Tyr Trp Gly Gln Gly Thr
            100                 105                 110

Leu Val Thr Val Ser Ala
        115

<210> SEQ ID NO 56
<211> LENGTH: 333
<212> TYPE: DNA
<213> ORGANISM: Artificial Sequence
<220> FEATURE:
<223> OTHER INFORMATION: Founder P6.2 VL sequence

<400> SEQUENCE: 56
gacattgtgc tgacccaatc tccagcttct ttggctgtgt ctctagggca gagggccacc     60
atatcctgca gagccagtga aagtgttgat agttatggca atagtttat gcactggtac     120 cagcagaaac aggacagcc acccaaactc ctcatctatc gtacatccaa cctagaatct    180
gggatccctg ccaggttcag tgcagtggg tctaggacag acttcaccct caccattaat    240
cctgtggagg ctgatgatgt tgcaacctat ttctgtcagc aaagttatga ggatccattc    300
acgttcggct cggggacaaa gttggaaata aaa                                 333

<210> SEQ ID NO 57
<211> LENGTH: 111
<212> TYPE: PRT
<213> ORGANISM: Artificial Sequence
<220> FEATURE:
<223> OTHER INFORMATION: Founder P6.2 VL sequence

<400> SEQUENCE: 57

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Thr Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Phe Cys Gln Gln Ser Tyr
                85                  90                  95

Glu Asp Pro Phe Thr Phe Gly Ser Gly Thr Lys Leu Glu Ile Lys
            100                 105                 110

<210> SEQ ID NO 58
<211> LENGTH: 448
<212> TYPE: PRT
<213> ORGANISM: Artificial Sequence
<220> FEATURE:
<223> OTHER INFORMATION: Monoclonal anti-IgE antibody clone E14 VH chain

<400> SEQUENCE: 58

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

```
Gly Trp Ile Asn Thr Tyr Thr Gly Glu Pro Thr Tyr Ala Asp Asp Phe
 50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Gly Ala Ala Ser His Thr Met Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 59
<211> LENGTH: 218
<212> TYPE: PRT
```

<213> ORGANISM: Artificial Sequence
<220> FEATURE:
<223> OTHER INFORMATION: Monoclonal anti-IgE antibody clone E14 VL chain

<400> SEQUENCE: 59

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Ala His Ser Tyr Met His Trp Tyr Gln Gln Lys Pro Gly Gln Pro Pro
        35                  40                  45

Lys Leu Leu Ile Tyr Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 60
<211> LENGTH: 448
<212> TYPE: PRT
<213> ORGANISM: Artificial Sequence
<220> FEATURE:
<223> OTHER INFORMATION: Monoclonal anti-IgE antibody clone E17 VH chain

<400> SEQUENCE: 60

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Ala Ala Ser His Thr Met Asp Tyr Trp Gly Gln Gly Thr
            100                 105                 110
```

```
Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 61
<211> LENGTH: 218
<212> TYPE: PRT
<213> ORGANISM: Artificial Sequence
<220> FEATURE:
<223> OTHER INFORMATION: Monoclonal anti-IgE antibody clone E17 VL chain

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30
```

```
Ser His Ala Tyr Met His Trp Tyr Gln Gln Lys Pro Gly Gln Pro Pro
             35                  40                  45

Lys Leu Leu Ile Tyr Tyr Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Trp
                 85                  90                  95

Glu Ile Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 62
<211> LENGTH: 448
<212> TYPE: PRT
<213> ORGANISM: Artificial Sequence
<220> FEATURE:
<223> OTHER INFORMATION: Monoclonal anti-IgE antibody clone E23 VH chain

<400> SEQUENCE: 62

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
             20                  25                  30

Gly Met Asn Trp Val Arg Gln Ala Pro Gly Gln Gly Leu Glu Trp Met
             35                  40                  45

Gly Trp Ile Asn Thr Tyr Thr Gly Glu Pro Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Gly Ala Ala Ser His Thr Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 63
<211> LENGTH: 218
<212> TYPE: PRT
<213> ORGANISM: Artificial Sequence
<220> FEATURE:
<223> OTHER INFORMATION: Monoclonal anti-IgE antibody clone E23 VL chain

<400> SEQUENCE: 63

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Tyr Ala Ser Asn Leu Lys Ala Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95
```

```
Glu Ile Pro Trp Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
            210                 215

<210> SEQ ID NO 64
<211> LENGTH: 449
<212> TYPE: PRT
<213> ORGANISM: Artificial Sequence
<220> FEATURE:
<223> OTHER INFORMATION: Monoclonal anti-IgE antibody clone S91 VH chain

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ser Trp Pro Tyr Trp Tyr Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 65
<211> LENGTH: 215
<212> TYPE: PRT
<213> ORGANISM: Artificial Sequence
<220> FEATURE:
<223> OTHER INFORMATION: Monoclonal anti-IgE antibody clone S91 VL chain

<400> SEQUENCE: 65

Gln Ser Ala Val Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asp Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Arg
                85                  90                  95

Val Asp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
```

```
                145                 150                 155                 160
Gly Val Glu Thr Thr Thr Pro Ser Lys Gln Ser Asn Asn Lys Tyr Ala
                    165                 170                 175
Ala Ser Ser Tyr Leu Ser Leu Thr Pro Glu Gln Trp Lys Ser His Arg
                    180                 185                 190
Ser Tyr Ser Cys Gln Val Thr His Glu Gly Ser Thr Val Glu Lys Thr
                    195                 200                 205
Val Ala Pro Thr Glu Cys Ser
                    210                 215

<210> SEQ ID NO 66
<211> LENGTH: 453
<212> TYPE: PRT
<213> ORGANISM: Artificial Sequence
<220> FEATURE:
<223> OTHER INFORMATION: Monoclonal anti-IgE antibody clone H6.2_15 VH
      chain

<400> SEQUENCE: 66

Gln Val Gln Leu Gly Gln Ser Gly Gly Gly Val Val Gln Pro Gly Arg
1               5                   10                  15
Ser Leu Arg Leu Ser Cys Ala Ala Ser Gly Phe Thr Phe Ser Asn Tyr
                20                  25                  30
Leu Ile Glu Trp Val Arg Gln Ala Pro Gly Lys Gly Leu Glu Trp Val
            35                  40                  45
Ala Val Ile Asn Pro Gly Ser Gly Phe Thr Lys Tyr Asn Glu Lys Phe
        50                  55                  60
Lys Gln Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Asp Val Tyr Ser Trp Phe Ala Tyr Trp Gly Gln Gly Thr
                100                 105                 110
Leu Val Thr Val Ser Ala Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Val Glu Pro Lys
                210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
```

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
450

<210> SEQ ID NO 67
<211> LENGTH: 214
<212> TYPE: PRT
<213> ORGANISM: Artificial Sequence
<220> FEATURE:
<223> OTHER INFORMATION: Monoclonal anti-IgE antibody clone H6.2_15 VL
      chain

<400> SEQUENCE: 67

Gln Ser Ala Leu Thr Gln Pro Ala Ser Val Ser Gly Ser Pro Gly Gln
1               5                   10                  15

Ser Ile Thr Ile Ser Cys Thr Arg Ala Ser Glu Ser Val Asp Ser Tyr
            20                  25                  30

Gly Asn Ser Phe Met His Gln His Pro Gly Lys Ala Pro Lys Leu
        35                  40                  45

Met Ile Tyr Glu Val Arg Thr Ser Asn Leu Glu Ser Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Gln Gln Ser Tyr
                85                  90                  95

Glu Asp Pro Phe Thr Phe Gly Ser Gly Thr Lys Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Lys Val Ala Trp Lys Ala Asp Gly Ser Pro Val Asn Thr Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

```
Tyr Ser Cys Gln Val Thr His Glu Gly Ser Thr Val Glu Lys Thr Val
        195                 200                 205

Ala Pro Ala Glu Cys Ser
        210

<210> SEQ ID NO 68
<211> LENGTH: 120
<212> TYPE: PRT
<213> ORGANISM: Artificial Sequence
<220> FEATURE:
<223> OTHER INFORMATION: Monoclonal anti-IgE antibody VH chain

<400> SEQUENCE: 68

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Ala Ala Ser His Thr Met Asp Tyr Trp Gly Gln Gly Thr
            100                 105                 110

Thr Val Thr Val Ser Ser Ala Ser
        115                 120

<210> SEQ ID NO 69
<211> LENGTH: 122
<212> TYPE: PRT
<213> ORGANISM: Artificial Sequence
<220> FEATURE:
<223> OTHER INFORMATION: Monoclonal anti-IgE antibody VH chain

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ser Ser Trp Pro Tyr Trp Tyr Phe Asp Leu Trp Gly Arg
            100                 105                 110

Gly Thr Leu Val Thr Val Ser Ser Ala Ser
        115                 120

<210> SEQ ID NO 70
<211> LENGTH: 125
<212> TYPE: PRT
```

<213> ORGANISM: Artificial Sequence
<220> FEATURE:
<223> OTHER INFORMATION: Monoclonal anti-IgE antibody VH chain

<400> SEQUENCE: 70

```
Gln Val Gln Leu Gly Gln Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Leu Ile Glu Trp Val Arg Gln Ala Pro Gly Lys Gly Leu Glu Trp Val
            35                  40                  45

Ala Val Ile Asn Pro Gly Ser Gly Phe Thr Lys Tyr Asn Glu Lys Phe
        50                  55                  60

Lys Gln Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Val Tyr Ser Trp Phe Ala Tyr Trp Gly Gln Gly Thr
            100                 105                 110

Leu Val Thr Val Ser Ala Val Thr Val Ser Ser Ala Ser
        115                 120                 125
```

<210> SEQ ID NO 71
<211> LENGTH: 7
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (4)..(4)
<223> OTHER INFORMATION: Xaa is Val or Gly

<400> SEQUENCE: 71

```
Val Gln Leu Xaa Gln Ser Gly
1               5
```

<210> SEQ ID NO 72
<211> LENGTH: 16
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (3)..(3)
<223> OTHER INFORMATION: Xaa is Ala or Arg
<220> FEATURE:
<221> NAME/KEY: MISC_FEATURE
<222> LOCATION: (5)..(5)
<223> OTHER INFORMATION: Xaa is Leu or Val
<220> FEATURE:
<221> NAME/KEY: MISC_FEATURE
<222> LOCATION: (6)..(6)
<223> OTHER INFORMATION: Xaa is Lys or Arg
<220> FEATURE:
<221> NAME/KEY: MISC_FEATURE
<222> LOCATION: (7)..(7)
<223> OTHER INFORMATION: Xaa is Leu or Val
<220> FEATURE:
<221> NAME/KEY: MISC_FEATURE
<222> LOCATION: (10)..(10)
<223> OTHER INFORMATION: Xaa is Ala or Lys
<220> FEATURE:
<221> NAME/KEY: MISC_FEATURE
<222> LOCATION: (14)..(14)
<223> OTHER INFORMATION: Xaa is Phe or Tyr

```
<400> SEQUENCE: 72

Pro Gly Xaa Ser Xaa Xaa Xaa Ser Cys Xaa Ala Ser Gly Xaa Thr Phe
1               5                   10                  15

<210> SEQ ID NO 73
<211> LENGTH: 12
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (8)..(8)
<223> OTHER INFORMATION: Xaa is Lys or Gln

<400> SEQUENCE: 73

Trp Val Arg Gln Ala Pro Gly Xaa Gly Leu Glu Trp
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (3)..(3)
<223> OTHER INFORMATION: Xaa is Arg or Gln
<220> FEATURE:
<221> NAME/KEY: MISC_FEATURE
<222> LOCATION: (6)..(6)
<223> OTHER INFORMATION: Xaa is Leu or Thr

<400> SEQUENCE: 74

Trp Gly Xaa Gly Thr Xaa Val Thr Val Ser Ser Ala
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (3)..(3)
<223> OTHER INFORMATION: Xaa is Thr, Lys, or Arg
<220> FEATURE:
<221> NAME/KEY: MISC_FEATURE
<222> LOCATION: (4)..(4)
<223> OTHER INFORMATION: Xaa is Ala or Ser
<220> FEATURE:
<221> NAME/KEY: MISC_FEATURE
<222> LOCATION: (5)..(5)
<223> OTHER INFORMATION: Xaa is Glu or Asp

<400> SEQUENCE: 75

Ser Leu Xaa Xaa Xaa Asp Thr Ala Val Tyr Tyr Cys Ala Arg
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Monoclonal anti-IgE antibody VH chain
<220> FEATURE:
<221> NAME/KEY: MISC_FEATURE
<222> LOCATION: (2)..(2)
<223> OTHER INFORMATION: Xaa is Phe or Val
```

```
<220> FEATURE:
<221> NAME/KEY: MISC_FEATURE
<222> LOCATION: (3)..(3)
<223> OTHER INFORMATION: Xaa is Thr or Val
<220> FEATURE:
<221> NAME/KEY: MISC_FEATURE
<222> LOCATION: (4)..(4)
<223> OTHER INFORMATION: Xaa is Ile, Phe, or Met
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (6)..(6)
<223> OTHER INFORMATION: Xaa is Leu, Arg, or Thr
<220> FEATURE:
<221> NAME/KEY: MISC_FEATURE
<222> LOCATION: (8)..(8)
<223> OTHER INFORMATION: Xaa is Asn or Thr
<220> FEATURE:
<221> NAME/KEY: MISC_FEATURE
<222> LOCATION: (10)..(10)
<223> OTHER INFORMATION: Xaa is Lys, Thr, or Val
<220> FEATURE:
<221> NAME/KEY: MISC_FEATURE
<222> LOCATION: (11)..(11)
<223> OTHER INFORMATION: Xaa is Asn or Ser

<400> SEQUENCE: 76

Arg Xaa Xaa Xaa Xaa Xaa Asp Xaa Ser Xaa Xaa Thr
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (6)..(6)
<223> OTHER INFORMATION: Xaa is Gly or Lys

<400> SEQUENCE: 77

Arg Phe Ser Gly Ser Xaa Ser Gly
1               5

<210> SEQ ID NO 78
<211> LENGTH: 15
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (3)..(3)
<223> OTHER INFORMATION: Xaa is Ile or Val
<220> FEATURE:
<221> NAME/KEY: MISC_FEATURE
<222> LOCATION: (5)..(5)
<223> OTHER INFORMATION: Xaa is Gly or Ser
<220> FEATURE:
<221> NAME/KEY: MISC_FEATURE
<222> LOCATION: (11)..(11)
<223> OTHER INFORMATION: Xaa is Glu or Val
<220> FEATURE:
<221> NAME/KEY: MISC_FEATURE
<222> LOCATION: (13)..(13)
<223> OTHER INFORMATION: Xaa is Asp or Val

<400> SEQUENCE: 78

Leu Thr Xaa Ser Xaa Leu Gln Ala Glu Asp Xaa Ala Xaa Tyr Tyr
1               5                   10                  15
```

```
<210> SEQ ID NO 79
<211> LENGTH: 7
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (3)..(3)
<223> OTHER INFORMATION: Xaa is Gly, Ser, or Gln

<400> SEQUENCE: 79

Phe Gly Xaa Gly Thr Lys Leu
1               5

<210> SEQ ID NO 80
<211> LENGTH: 15
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (6)..(6)
<223> OTHER INFORMATION: Xaa is Phe or Thr
<220> FEATURE:
<221> NAME/KEY: MISC_FEATURE
<222> LOCATION: (7)..(7)
<223> OTHER INFORMATION: Xaa is Ile or Leu
<220> FEATURE:
<221> NAME/KEY: MISC_FEATURE
<222> LOCATION: (12)..(12)
<223> OTHER INFORMATION: Xaa is Asp or Ser
<220> FEATURE:
<221> NAME/KEY: MISC_FEATURE
<222> LOCATION: (14)..(14)
<223> OTHER INFORMATION: Xaa is Glu or Gln

<400> SEQUENCE: 80

Ala Ala Pro Ser Val Xaa Xaa Phe Pro Pro Ser Xaa Glu Xaa Leu
1               5                   10                  15

<210> SEQ ID NO 81
<211> LENGTH: 12
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is Ser or Thr
<220> FEATURE:
<221> NAME/KEY: MISC_FEATURE
<222> LOCATION: (3)..(3)
<223> OTHER INFORMATION: Xaa is Leu or Val
<220> FEATURE:
<221> NAME/KEY: MISC_FEATURE
<222> LOCATION: (7)..(7)
<223> OTHER INFORMATION: Xaa is Ile or Leu
<220> FEATURE:
<221> NAME/KEY: MISC_FEATURE
<222> LOCATION: (8)..(8)
<223> OTHER INFORMATION: Xaa is Asn or Ser
<220> FEATURE:
<221> NAME/KEY: MISC_FEATURE
<222> LOCATION: (9)..(9)
<223> OTHER INFORMATION: Xaa is Asp or Asn

<400> SEQUENCE: 81

Ala Xaa Xaa Val Cys Leu Xaa Xaa Xaa Phe Tyr Pro
1               5                   10
```

<210> SEQ ID NO 82
<211> LENGTH: 12
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is Lys or Arg
<220> FEATURE:
<221> NAME/KEY: MISC_FEATURE
<222> LOCATION: (3)..(3)
<223> OTHER INFORMATION: Xaa is Ser or Val
<220> FEATURE:
<221> NAME/KEY: MISC_FEATURE
<222> LOCATION: (5)..(5)
<223> OTHER INFORMATION: Xaa is Ala or Ser
<220> FEATURE:
<221> NAME/KEY: MISC_FEATURE
<222> LOCATION: (7)..(7)
<223> OTHER INFORMATION: Xaa is Glu or Gln
<220> FEATURE:
<221> NAME/KEY: MISC_FEATURE
<222> LOCATION: (11)..(11)
<223> OTHER INFORMATION: Xaa is Glu or Gln

<400> SEQUENCE: 82

His Xaa Xaa Tyr Xaa Cys Xaa Val Thr His Xaa Gly
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is Ala, Asp, or Pro
<220> FEATURE:
<221> NAME/KEY: MISC_FEATURE
<222> LOCATION: (4)..(4)
<223> OTHER INFORMATION: Xaa is Ala, Leu, or Val
<220> FEATURE:
<221> NAME/KEY: MISC_FEATURE
<222> LOCATION: (5)..(5)
<223> OTHER INFORMATION: Xaa is Ala or Ser
<220> FEATURE:
<221> NAME/KEY: MISC_FEATURE
<222> LOCATION: (6)..(6)
<223> OTHER INFORMATION: Xaa is Gly or Val
<220> FEATURE:
<221> NAME/KEY: MISC_FEATURE
<222> LOCATION: (8)..(8)
<223> OTHER INFORMATION: Xaa is Leu or Pro
<220> FEATURE:
<221> NAME/KEY: MISC_FEATURE
<222> LOCATION: (10)..(10)
<223> OTHER INFORMATION: Xaa is Glu or Gln
<220> FEATURE:
<221> NAME/KEY: MISC_FEATURE
<222> LOCATION: (11)..(11)
<223> OTHER INFORMATION: Xaa is Arg or Ser
<220> FEATURE:
<221> NAME/KEY: MISC_FEATURE
<222> LOCATION: (12)..(12)
<223> OTHER INFORMATION: Xaa is Ala, Ile, or Val
<220> FEATURE:
<221> NAME/KEY: MISC_FEATURE
<222> LOCATION: (15)..(15)
<223> OTHER INFORMATION: Xaa is Asn or Ser

<400> SEQUENCE: 83

```
Pro Xaa Ser Xaa Xaa Xaa Ser Xaa Gly Xaa Xaa Xaa Thr Ile Xaa Cys
1               5                   10                  15

<210> SEQ ID NO 84
<211> LENGTH: 13
<212> TYPE: PRT
<213> ORGANISM: Artificial Sequence
<220> FEATURE:
<223> OTHER INFORMATION: Monoclonal anti-IgE antibody VL chain
<220> FEATURE:
<221> NAME/KEY: MISC_FEATURE
<222> LOCATION: (2)..(2)
<223> OTHER INFORMATION: Xaa is His or Gln
<220> FEATURE:
<221> NAME/KEY: MISC_FEATURE
<222> LOCATION: (3)..(3)
<223> OTHER INFORMATION: Xaa is His or Lys
<220> FEATURE:
<221> NAME/KEY: MISC_FEATURE
<222> LOCATION: (6)..(6)
<223> OTHER INFORMATION: Xaa is Lys or Gln
<220> FEATURE:
<221> NAME/KEY: MISC_FEATURE
<222> LOCATION: (7)..(7)
<223> OTHER INFORMATION: Xaa is Ala or Pro
<220> FEATURE:
<221> NAME/KEY: MISC_FEATURE
<222> LOCATION: (11)..(11)
<223> OTHER INFORMATION: Xaa is Leu or Met

<400> SEQUENCE: 84

Gln Xaa Xaa Pro Gly Xaa Xaa Pro Lys Leu Xaa Ile Tyr
1               5                   10
```